(12) United States Patent
Kakkis et al.

(10) Patent No.: US 11,202,822 B2
(45) Date of Patent: *Dec. 21, 2021

(54) METHODS FOR TREATING HYPOPHOSPHATEMIC DISORDERS

(71) Applicants: Ultragenyx Pharmaceutical Inc., Novato, CA (US); Kyowa Kirin Co., Ltd., Tokyo (JP)

(72) Inventors: Emil D. Kakkis, Novato, CA (US); Javier San Martin, Novato, CA (US); Tomohiro Sudo, Tokyo (JP)

(73) Assignees: Ultragenyx Pharmaceutical Inc., Novato, CA (US); Kyowa Kirin Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/831,179

(22) Filed: Mar. 26, 2020

(65) Prior Publication Data

US 2020/0330575 A1 Oct. 22, 2020

Related U.S. Application Data

(63) Continuation of application No. 14/725,320, filed on May 29, 2015, now Pat. No. 10,639,360.

(60) Provisional application No. 62/009,474, filed on Jun. 9, 2014.

(51) Int. Cl.
| | | |
|---|---|---|
| *A61K 39/395* | (2006.01) | |
| *A61K 39/00* | (2006.01) | |
| *C07K 16/22* | (2006.01) | |

(52) U.S. Cl.
CPC ...... *A61K 39/001132* (2018.08); *C07K 16/22* (2013.01); *A61K 2039/505* (2013.01); *A61K 2039/54* (2013.01); *A61K 2039/545* (2013.01); *C07K 2317/21* (2013.01); *C07K 2317/565* (2013.01); *C07K 2317/76* (2013.01); *C07K 2317/90* (2013.01)

(58) Field of Classification Search
None
See application file for complete search history.

(56) References Cited

U.S. PATENT DOCUMENTS

| | | |
|---|---|---|
| 7,223,563 B2 | 5/2007 | Econs et al. |
| 7,314,618 B2 | 1/2008 | Econs et al. |
| 7,745,406 B2 | 6/2010 | Econs et al. |
| 7,883,705 B2 | 2/2011 | Yamazaki et al. |
| 7,923,012 B2 | 4/2011 | Yamazaki et al. |
| 7,947,810 B2 | 5/2011 | Econs et al. |
| 7,981,419 B2 | 7/2011 | Yamashita et al. |
| 8,586,317 B2 | 11/2013 | Econs et al. |
| 8,889,426 B2 | 11/2014 | Mohammadi et al. |
| 8,889,621 B2 | 11/2014 | Mohammadi et al. |
| 9,272,017 B2 | 3/2016 | Mohammadi et al. |
| 9,290,599 B2 | 3/2016 | Hogan et al. |
| 10,639,360 B2 | 5/2020 | Kakkis et al. |
| 2009/0148461 A1 | 6/2009 | Yamazaki et al. |
| 2011/0182913 A1 | 7/2011 | Yamazaki et al. |
| 2012/0064544 A1 | 3/2012 | Econs et al. |
| 2016/0159895 A1 | 6/2016 | Yamazaki et al. |

FOREIGN PATENT DOCUMENTS

| | | |
|---|---|---|
| AU | 2005202100 A1 | 6/2005 |
| CN | 1446227 A1 | 10/2003 |
| CN | 102702355 A | 10/2012 |
| JP | 2004-504063 A | 2/2004 |
| WO | WO-02/08271 A1 | 1/2002 |
| WO | WO 2015/191312 A1 | 12/2005 |
| WO | WO-2008/099969 A1 | 8/2008 |
| WO | WO 2012/050673 A1 | 4/2012 |

OTHER PUBLICATIONS

International Search Report and Written Opinion for International Application No. PCT/US2015/033226, dated Nov. 13, 2015, 12 pages.
Extended European Search Report for European Application No. 15806501.1, dated Dec. 19, 2017, 7 pages.
Aono, Y. et al., "Anti-FGF-23 Neutralizing Antibodies Ameliorate Muscle Weakness and Decreased Spontaneous Movement of Hyp Mice," Journal of Bone and Mineral Research, vol. 26, No. 4, Apr. 2011, pp. 803-810.
Aono, Y. et al., "Therapeutic Effects of Anti-FGF23 Antibodies in Hypophosphatemic Rickets/Osteomalacia," Journal of Bone and Mineral Research, 24(11):1879-1888 (2009).
Carpenter, T. et al., "Randomized trial of the anti-FGF23 antibody KRN23 in X-linked hypophosphatemia," The Journal of Clinical Investigation, 24(4):1587-1597 (2014).
Carpenter, T. et al., "Efficacy and Safety of a Human Monoclonal Anti-FGF23 Antibody (KRN23) in a Cumulative 4-Month Dose Escalation (KRN23-INT-001) and 12-Month Long-Term Extension Study (KRN23-INT-002) in Adult Subjects with X-Linked Hypophosphatemia (XLH)," 2014 ASBMR: Plenary Oral Session No. 1082 Time: 10:15 AM—10:30 AM; Sep. 14, 2014, Brown Convention Center. Houston, Texas, 34 pages.
Capenter, T. O. et al., "A Clinician's Guide to X-Linked Hypophosphatemia," J Bone Miner Res. Jul. 2011 ; 26(7):1381-1388. doi:10.1002/jbmr.340.

(Continued)

*Primary Examiner* — Christine J Saoud

(74) *Attorney, Agent, or Firm* — Cooley LLP

(57) ABSTRACT

The present invention provides compositions and methods for treating a hypophosphatemic disorder, such as X-linked hypophosphatemia (XLH). The method entails administering to a subject a pharmaceutical composition containing an anti-FGF23 ligand, wherein the dosing regimen of the pharmaceutical is designed to reach effective and efficient control of FGF23 activity.

9 Claims, 25 Drawing Sheets

Specification includes a Sequence Listing.

(56) References Cited

OTHER PUBLICATIONS

Carpenter, T., et al., "A randomized, double-blind, placebo-controlled, ascending, single-dose study of a human monoclonal anti-FGF23 antibody (KRN23) in X-linked hypophosphatemia," Bone Abstracts (2014) 3 PP90, DOI:10.1530/boneabs.3.PP90, Retreived from the Internet: <URL: http://www.boneabstracts.org/ba/0003/ba0003PP90.htm>, Retrieved on Feb. 22, 2017, 2 pages.
Clinicaltrials.gov, Trial Record NCT02163577, "Study of KRN23, a Recombinant Fully Human Monoclonal Antibody Against FGF23, in Pediatric Subjects With X-linked Hypophosphatemia (XLH)," Sponsored by Ultragenyx Pharmaceutical Inc., First Received Jun. 9, 2014, accessed Feb. 22, 2017, 4 pages.
Database GenBank [Online], Apr. 30, 2011, XP002776304, Database Accession No. AED38397.1, 1 page.
Database GenBank [Online], Apr. 30, 2011, XP002776305, Database Accession No. AED38398.1, 1 page.
Fukumoto, S., "FGF23-FGF Receptor/Klotho Pathway as a New Drug Target for Disorders of Bone and Mineral Metabolism," Calcif Tissue Int (2016) 98:334-340.
Fukumoto, S., "Anti-fibroblast Growth Factor 23 Antibody Therapy," Curr. Opin. Nephrol. Hypertens, 23(4):346-351 (Jul. 2014).
Fukumoto, S., "Novel Treatment for FGF23-Related Hypophosphatemic Diseases," Clinical Calcium, 25(1):37-44 (2015).
Imel, E. A. et al., "The First Multi-Dose Trial of a Human Anti-FGF23 (Fibroblast Growth Factor 23) Antibody (KRN23) in Adults with X-Linked Hypophosphatemia (XLH)," 2014 ENDO/ICE: Oral Session No. OR43-1, Time: 9:30 AM-11:00 AM; Tuesday, Jun. 24, 2014, McCormick Place West, Chicago, IL, 29 pages.
Imel, E. A. et al., "OR431 The First Multi-Dose Trial of a Human Anti-FGF23 (Fibroblast Growth Factor 23) Antibody (KRN23) in Adults with X-Linked Hypophosphatemia (XLH)," Abstracts—Orals, Poster Preview Presentations, and Posters Session: OR43—FGF23 & Phosphate Disorders; Osteoporosis risk factors Clinical, Chicago, IL, Jun. 24, 2014, 1 pages.
Imura et al., "Secreted Klotho protein in sera and CSF: implication for post-translational cleavage in release of Klotho protein from cell membrane." FEBS Letters (2004); 565.1: 143-147.
Yasuhara, M. "Fundamentals of Clinical Pharmacokinetics", Proceedings of the 16th Training Course in Clinical Pharmacology, Pharmacokinetics for Primers. Jul. 2010. 41(4): 155-8. (Machine Translation included).
Kolek et al., "1α, 25-Dihydroxyvitamin D3 upregulates FGF23 gene expression in bone: the final link in a renal-gastrointestinal-skeletal axis that controls phosphate transport." American Journal of Physiology-Gastrointestinal and Liver Physiology (2005); 289.6: G1036-G1042.
Kurosu et al., "Suppression of aging in mice by the hormone Klotho." Science (2005); 309.5742: 1829-1833.
Larsson et al., "Transgenic mice expressing fibroblast growth factor 23 under the control of the α1 (I) collagen promoter exhibit growth retardation, osteomalacia, and disturbed phosphate homeostasis." Endocrinology (2004); 145.7: 3087-3094.
Liu et al., "Novel regulators of Fgf23 expression and mineralization in Hyp bone." Molecular Endocrinology (2009); 23.9: 1505-1518.
Matsumara et al., "Identification of the HumanKlothoGene and Its Two Transcripts Encoding Membrane and SecretedKlothoProtein." Biochemical and Biophysical Research Communications (1998); 242.3: 626-630. (Abstract).
Riminucci et al., "FGF-23 in fibrous dysplasia of bone and its relationship to renal phosphate wasting." The Journal of Clinical Investigation (2003); 112.5: 683-692.
Ruppe, M. D., et al., "Effect of Four Monthly Doses of a Human Monoclonal Anti-FGF23 (Fibroblast Growth Factor 23) Antibody (KRN23) on Quality of Life in X-Linked Hypophosphatemia (XLH)," ICE/ENDO 2014, Abstracts—Orals, Poster Preview Presentations, and Posters Session: MON 01930225—Diseases of Bone and Mineral Metabolism Clinical, Chicago, IL, Jun. 23, 2014, 1 page.
Shimada et al., "FGF-23 transgenic mice demonstrate hypophosphatemic rickets with reduced expression of sodium phosphate cotransporter type IIa." Biochemical and Biophysical Research Communications (2004); 314.2: 409-414. (Abstract).
Shimada et al., "FGF-23 is a potent regulator of vitamin D metabolism and phosphate homeostasis." Journal of Bone and Mineral Research (2004); 19.3: 429-435. (Abstract).
Shimada, T., "Anti-FGF23 antibody, a new therapeutic approach for hypophosphatemic rickets/osteomalacia," Clinical Calcium, 23(10):77-83 (2013).
Shimada, T. et al., "FGF23 as a Novel Therapeutic Target," Chap. 10 In: Endocrine FGFs and Klothos, Makoto Kuro-o (eds)., 2012, Landes Bioscience and Springer Science+Business Media, pp. 158-170.
Shiraki-Iida et al., "Structure of the mouse klotho gene and its two transcripts encoding membrane and secreted protein." FEBS Letters (1998); 424.1: 6-10.
Ultragenyx Pharmaceutical Inc., "Ultragenyx Announces Initiation of a Phase 2 Study of $KRN_{23}$ for Pediatric X-Linked Hypophosphatemia in the US and EU," Jul. 1, 2014, 4 pages.
Yamazaki, Y. et al., "Anti-FGF23 Neutralizing Antibodies Show the Physiological Role and Structural Features of FGF23," Journal of Bone and Mineral Research, 23(9):1509-1518 (Apr. 2008).
Yamashita et al., "Identification of a novel fibroblast growth factor, FGF-23, preferentially expressed in the ventrolateral thalamic nucleus of the brain." Biochemical and biophysical research communications (2000); 277.2: 494-498.
Zhang, X. et al., "Pharmacokinetics (PK) and Pharmacodynamics (PD) Following Four Monthly Doses of a Human Monoclonal Anti-FGF23 (Fibroblast Growth Factor 23) Antibody (KRN23) in Adults with X-Linked Hypophosphatemia (XLH)," ICE/ENDO 2014, Abstracts—Orals, Poster Preview Presentations, and Posters Session: MON 01930225—Diseases of Bone and Mineral Metabolism Clinical, Chicago, IL, Jun. 23, 2014, 2 pages.
Alon, U. et al., "Calcimimetics as an Adjuvant Treatment for Familial Hypophosphatemic Rickets," Clinical Journal of the American Society of Nephrology 3: 658-664, 2008.
Carpenter, T. et al., "A Randomized, Open-label Phase 2 Study of KRN23, a Fully Human Anti-FGF23 Monoclonal Antibody, in 52 Children with X-linked Hypophosphatemia (XLH): 40-Week Results," ASBMR: Plenary Oral Session No. 1154, Time: 9:45 AM—10:00 AM, Georgia World Congress Center, Room A412, Atlanta, Georgia, 17 pages.
Endo, I. et al., "Clinical Usefulness of Measurement of Fibroblast Growth Factor 23 (FGF23) in Hypophosphatemic Patients Proposal of Diagnostic Criteria Using FGF23 Management," Bone 42: 1235-1239, 2008.
Geller, J. et al., "Cinacalcet in the Management of Tumor-Induced Osteomalacia," Journal of Bone and Mineral Research, vol. 22, No. 6, pp. 931-937, Jun. 2007.
Imel, E. et al., "Treatment of X-Linked Hypophosphatemia with Calcitriol and Phosphate Increases Circulating Fibroblast Growth Factor 23 Concentrations," Journal of Clinical Endocrinology & Metabolism 95(4): 1846-1850, Apr. 2010.
Keizer, R. et al., "Clinical Pharmacokinetics of Therapeutic Monoclonal Antibodies," Clinical Pharmacokinetics 49(8): 493-507, 2010.
Liu, S. et al., "Fibroblast Growth Factor 23 is a Counter-Regulatory Phosphaturic Hormone for Vitamin D," Journal of the American Society of Nephrology 17: 1305-1315, 2006.
Perwad, F. et al., "Dietary and Serum Phosphorus Regulate Fibroblast Growth Factor 23 Expression and 1,25-Dihydroxyvitamin D Metabolism in Mice," Endocrinology 146(12): 5358-5364, 2005.
Erbitux Product Label, ImClone Systems Incorporated and Bristol-Myers Squibb Company, 18 pages, 2004.
Lucentis Product Label, Genentech, Inc., 14 pages, 2014.
Remicade Product Label, Janssen Biotech, Inc., 58 pages, 2013.
Rituxan Product Label, Genentech, Inc., 40 pages, 2012.
Vectibix Product Label, Amgen Inc., 14 pages, 2009.
"Ultragenyx Reports Positive Interim Data from Pediatric and Adult Phase 2 Studies of KRN23 in X-Linked Hypophosphatemia," Press Release, Sep. 19, 2016, 5 pages.
Onuchic, L. et al., "Potential effects of alendronate on fibroblast growth factor 23 levels and effective control of hypercalciuria in an adult with Jansen's metaphyseal chondrodysplasia", The Journal of Clinical Endocrinology and Metabolism 97(4):1098-103. (Jan. 2012).

(56) References Cited

OTHER PUBLICATIONS

Pavik, I. et al., "Patients with autosomal dominant polycystic kidney disease have elevated fibroblast growth factor 23 levels and a renal leak of phosphate", Kidney Int.; 79(2):234-40. (Jan. 2011). Epub Oct. 13, 2010.

Domrongkitchaiporn, S. et al., "Oral phosphate supplementation corrects hypophosphatemia and normalizes plasma FGF23 and 25-hydroxyvitamin D3 levels in women with chronic metabolic acidosis", Exp Clin Endocrinol Diabetes;118(2):105-12. (Feb. 2010). Epub May 15, 2009.

Day, A. L. et al., "Burosumab in tumor-induced osteomalacia: A case report;" Joint Bone Spine.;87(1):81-83. (Jan. 2020). doi: 10.1016/j.jbspin.2019.07.012. Epub Aug. 3, 2019. PMID: 31382017.

Imanishi, Y. et al. "Interim Analysis of a Phase 2 Open-Label Trial Assessing Burosumab Efficacy and Safety in Patients With Tumor-Induced Osteomalacia", Journal of Bone and Mineral Research, US. 36(2): 262-70. doi:10.1002/jbmr.4184, ISSN 0884-0431. (Sep. 23, 2020).

Ito, N., "Effects of burosumab, an anti-FGF23 antibody, in patients with tumor-induced osteomalacia: Results from an ongoing phase 2 study", Embase, Elsevier Science Publishers, Amsterdam, NL, Database accession No. EMB-631809895.2 pgs. (Nov. 1, 2018).

Jan De Beur, S, et al. "Burosumab improves the biochemical, skeletal, and clinical symptoms of tumor-induced osteomalacia (TIO) syndrome", Embase, Elsevier Science Publishers, Amsterdam, NL, Database accession No. EMB-633781858.2 pgs. (Apr. 4, 2019).

Jan De Beur, S, et al. "Burosumab improved serum phosphorus, osteomalacia, mobility, and fatigue in the 48-week, phase 2 study in adults with tumor-induced osteomalacia syndrome", Embase, Elsevier Science Publishers, Amsterdam, NL; Database accession No. EMB-631808042. 2 pgs. (Nov. 1, 2018).

Kinoshita, Y. et al., "X-Linked Hypophosphatemia and FGF23-Related Hypophosphatemic Diseases: Prospect for New Treatment"; Endocr Rev.;39(3):274-291. (Jun. 1, 2018) doi: 10.1210/er.2017-00220. PMID: 29381780.

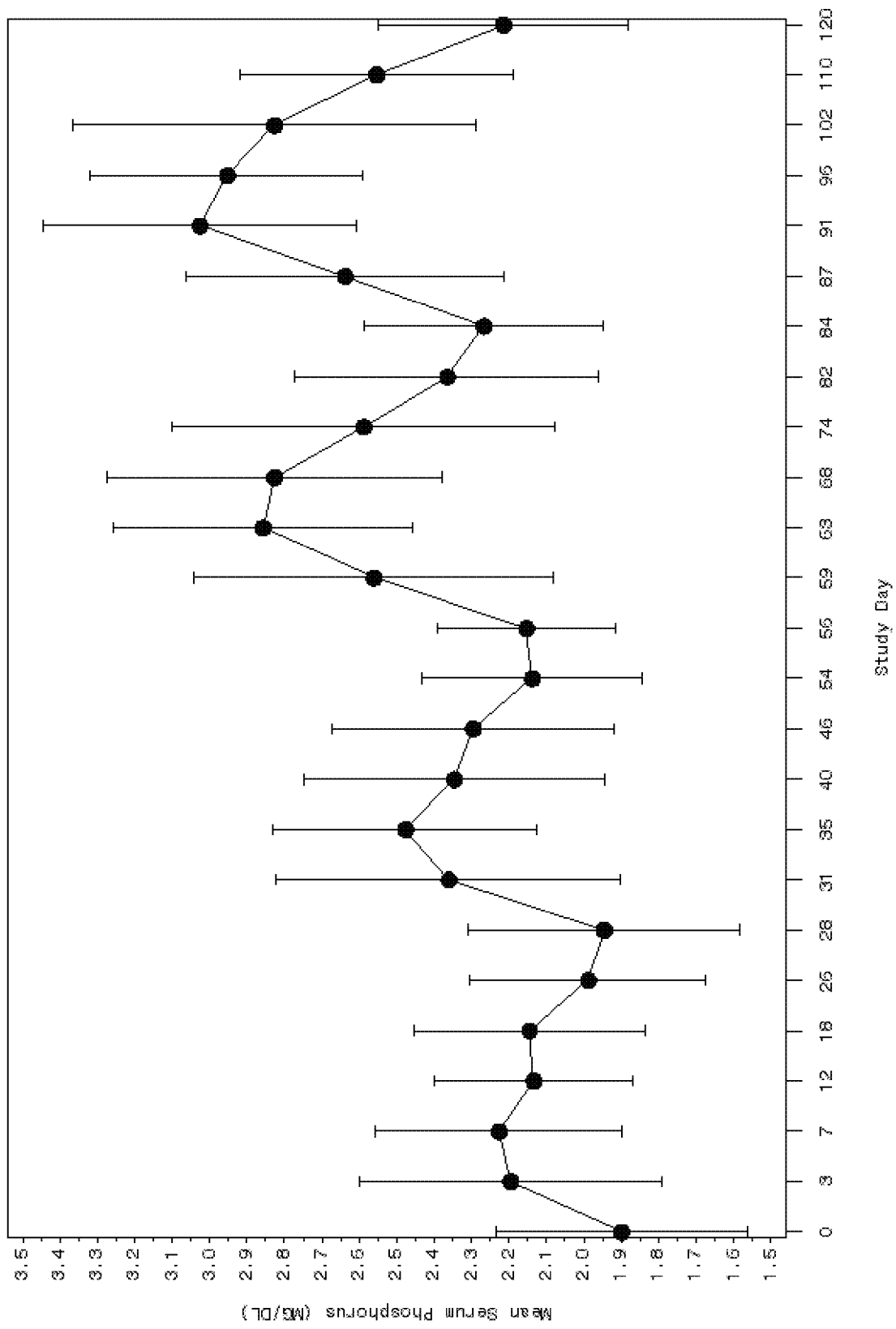
FIG. 1 Mean (± SD) Serum Phosphorus Values by Study Day – All Subjects Treated with KRN23 (Efficacy Analysis Set)

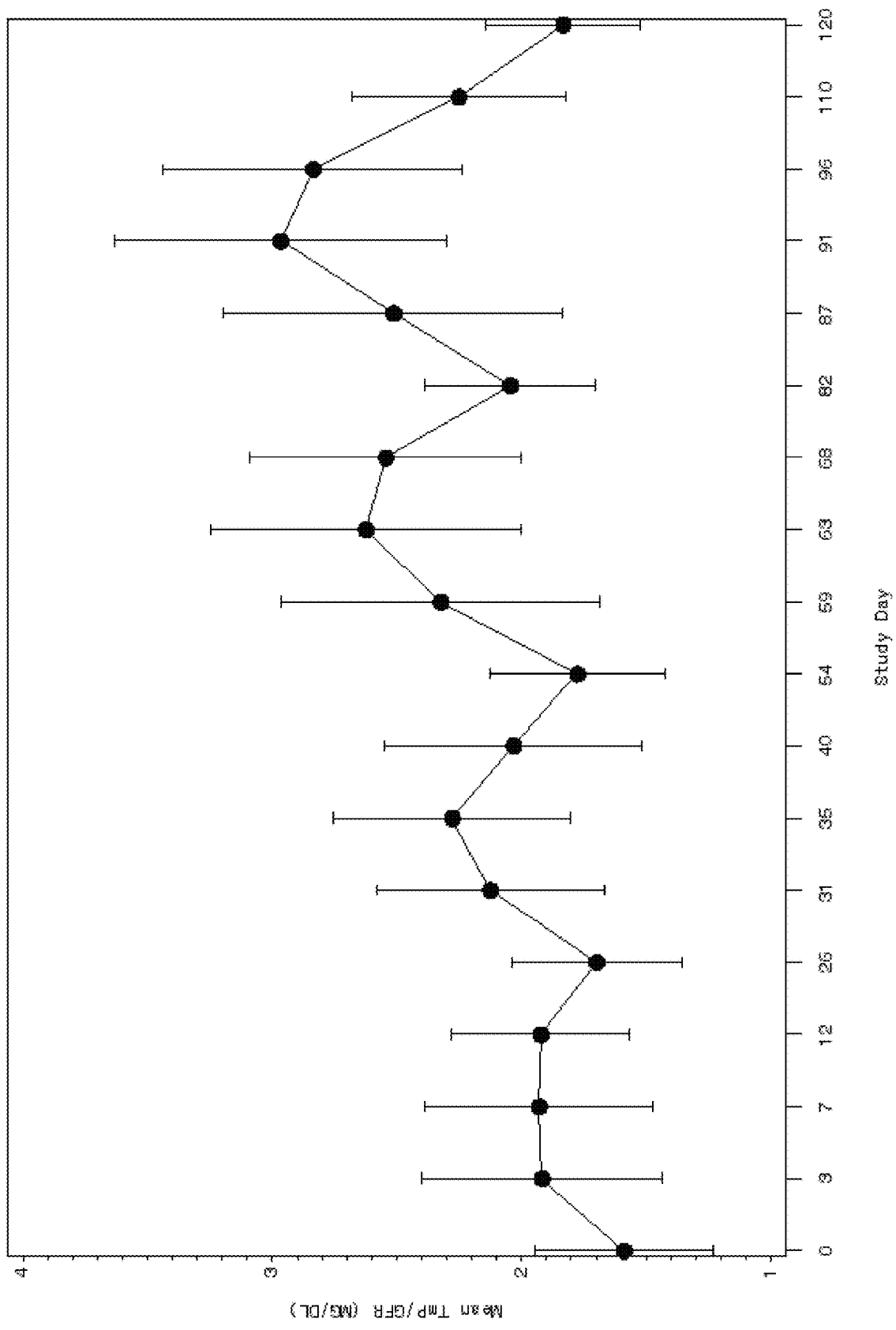
FIG. 2 Mean (± SD) TmP/GFR Levels (mg/dL) by Study Day – All Subjects Treated with KRN23 (Efficacy Analysis Set)

FIG. 3A and 3B Scatter Plot of $AUC_{last}$ (Left Panel) and $AUC_n$ (Right Panel) for Serum Phosphorus versus $AUC_{last}$ (3A, Left Panel) and $AUC_n$ (3B, Right Panel) for TmP/GFR for All Subjects (Efficacy Analysis Set)

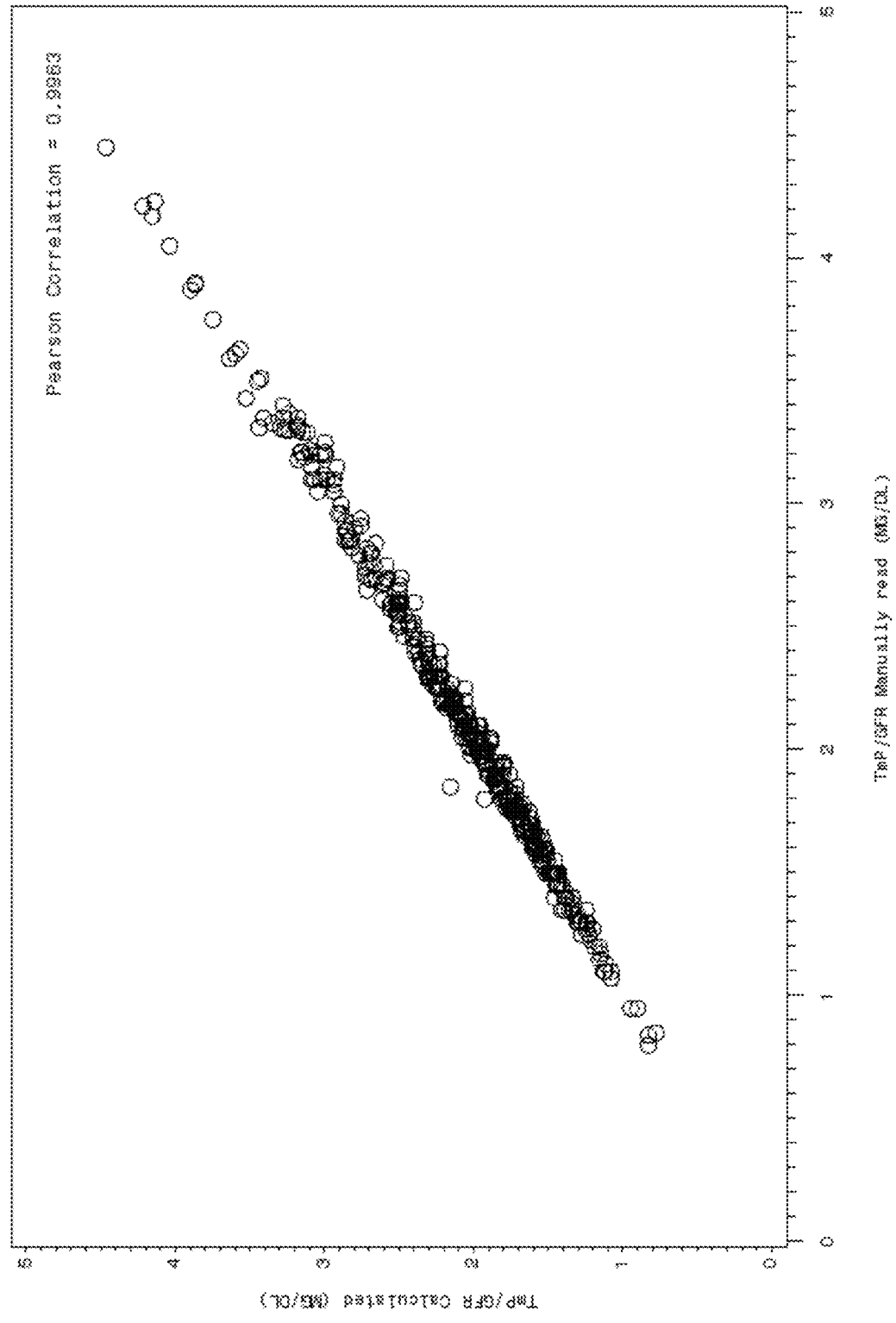
FIG. 4 Scatter Plot of TmP/GFR Calculated versus TmP/GFR Manually Read from Nomogram - All Subjects Treated with KRN23 (Efficacy Analysis Set)

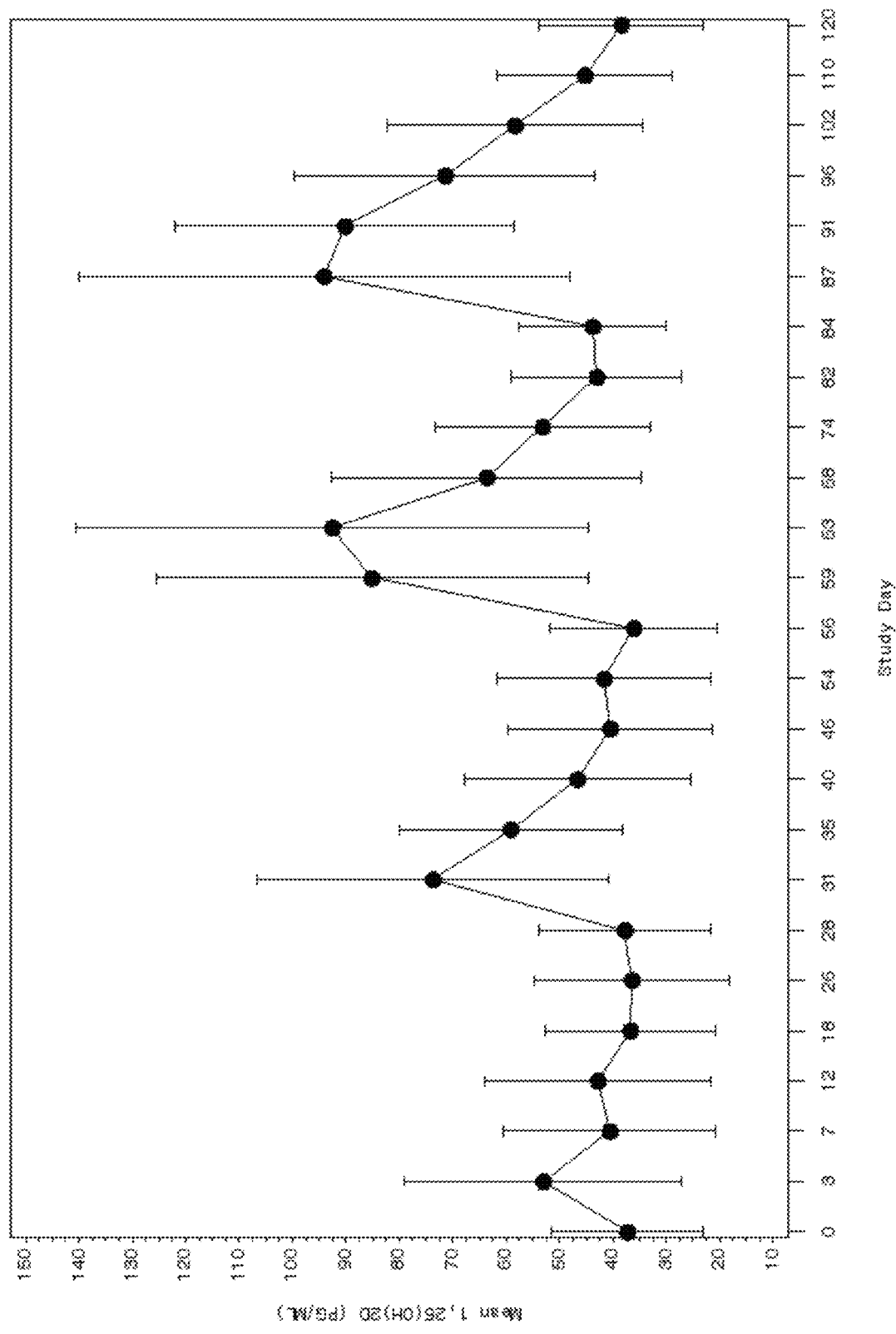
FIG. 5 Mean (± SD) 1,25(OH)₂D Levels (pg/mL) Over Time for the 4 Dosing Intervals - All Subjects Treated with KRN23 (Efficacy Analysis Set)

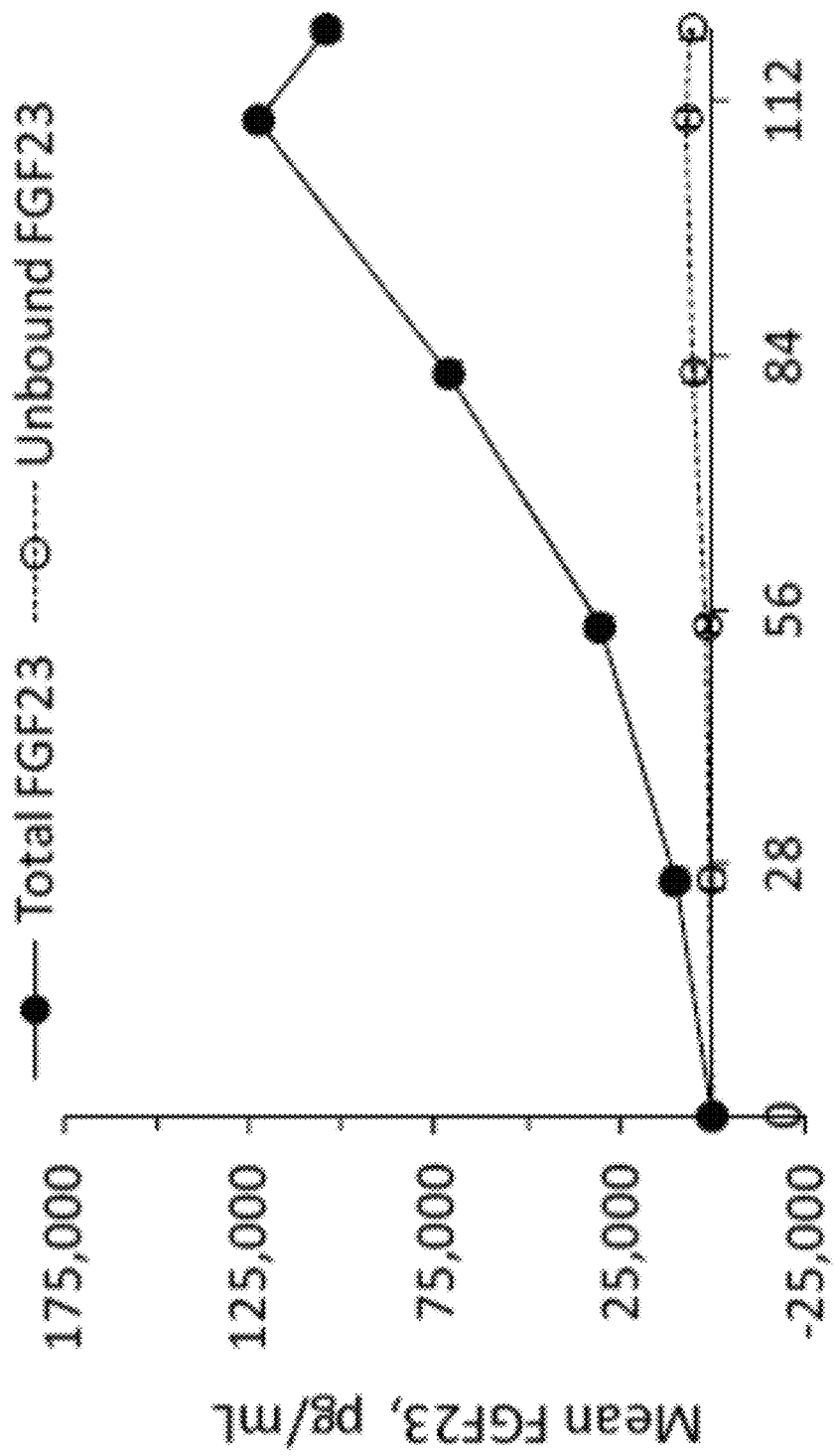
FIG. 6 Mean (± SD) Total FGF23 and Unbound FGF23 Values Over Time (Efficacy Analysis Set)

FIG. 7A and 7B  Mean (± SD) KRN23 Concentration Over Time (During the 4 Dosing Intervals) (Pharmacokinetic Analysis Set)

LogLinear

Linear:Linear

FIG. 8A and 8B  Scatter Plots of AUC for Serum Phosphorus Change from Baseline versus Serum KRN23 AUC (Pharmacokinetic Analysis Set)

FIG. 9A and 9B  Scatter Plots of AUC for TMP/GFR Change from Baseline versus Serum KRN23 AUC (Pharmacokinetic Analysis Set)

FIG. 10A and 10B  Scatter Plots of AUC for Serum 1,25-Dihydroxyvitamin D Change from Baseline versus Serum KRN23 AUC (Pharmacokinetic Analysis Set)

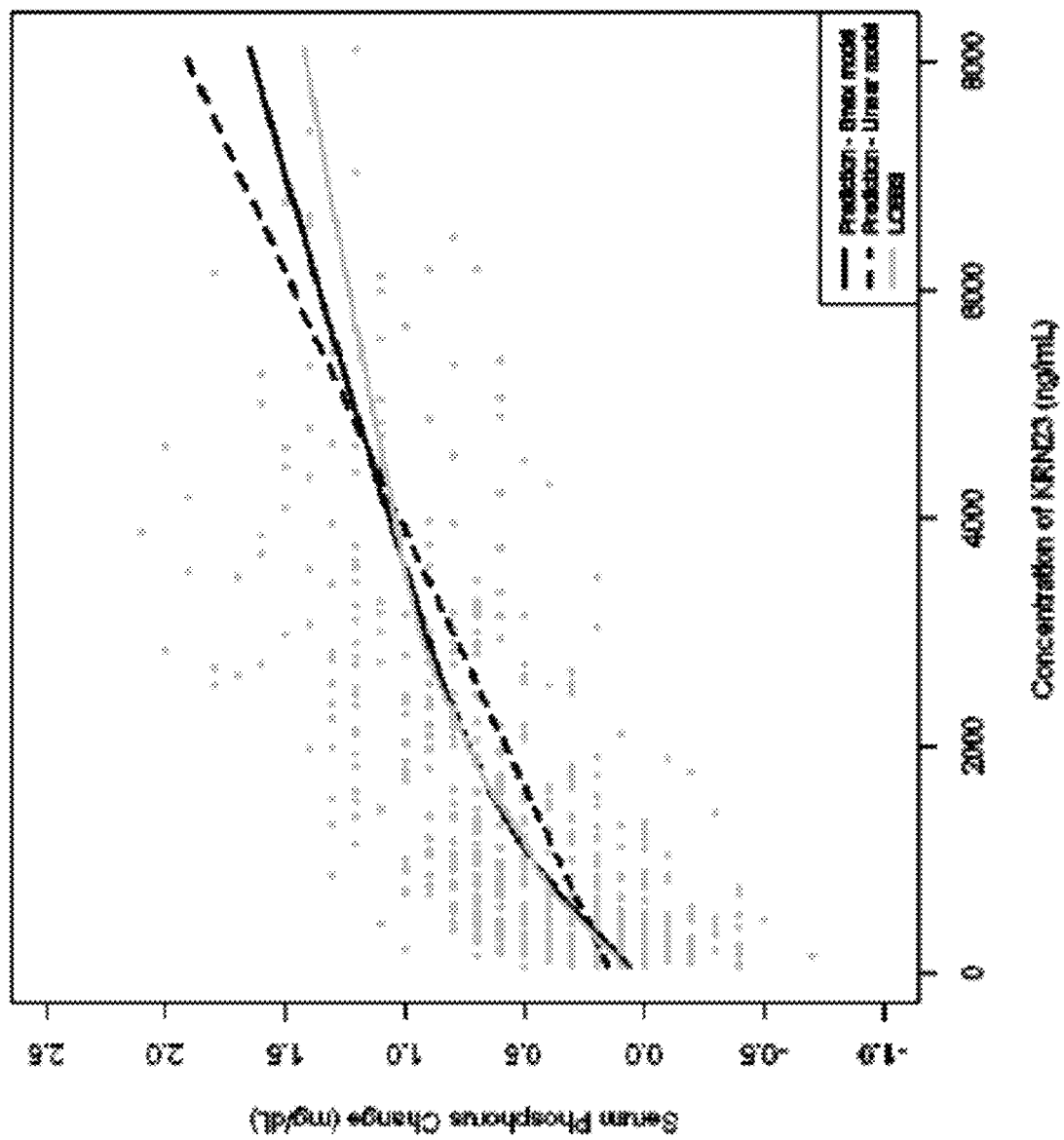
FIG. 11 Relationship Between KRN23 Concentration and Change From Baseline in Serum Phosphorus in Adult Subjects with XLH Treated with KRN23 from the Population PK-PD Model Predictions (Pharmacokinetic Analysis Set)

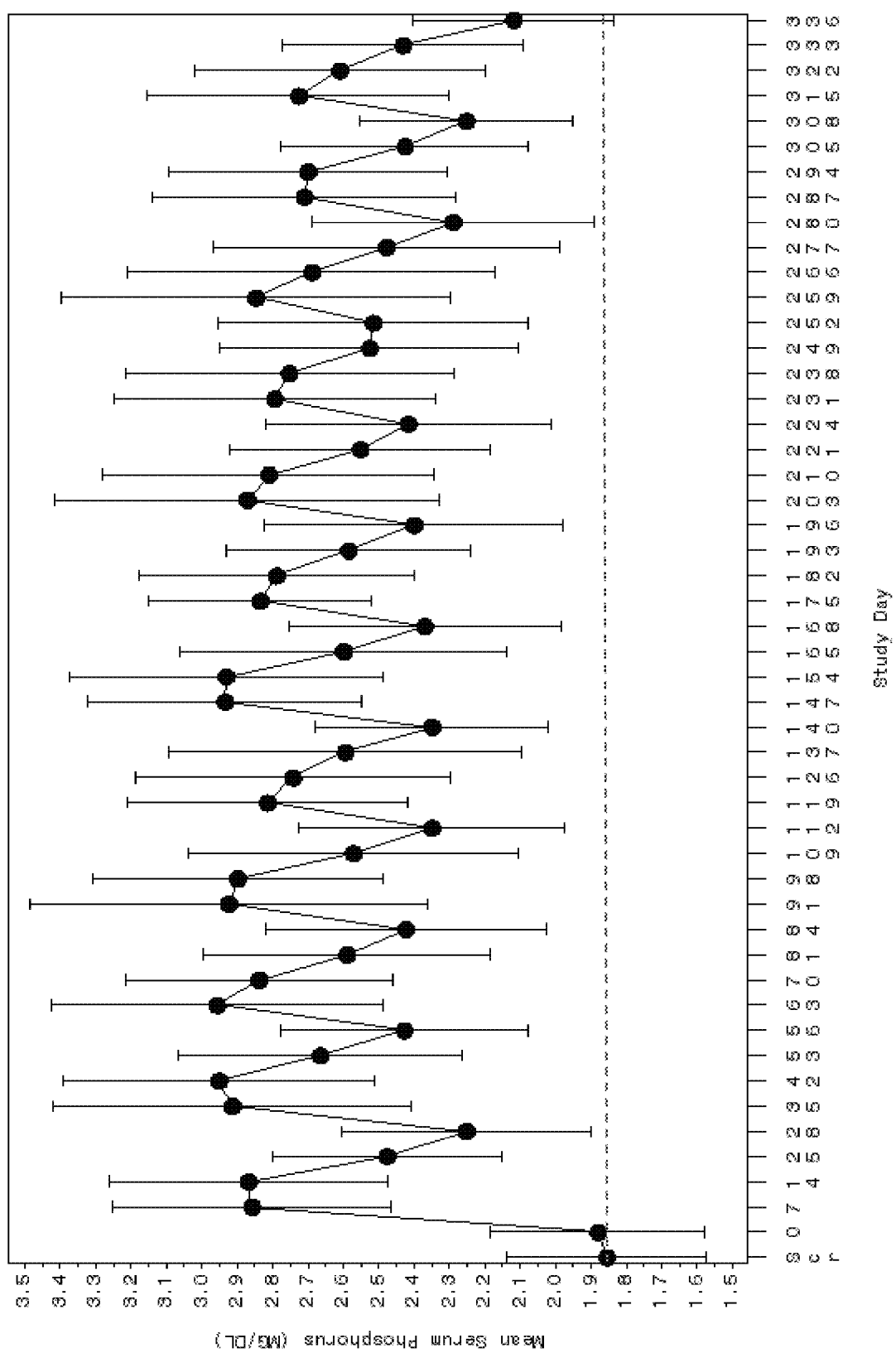
FIG. 12 Mean (±SD) Serum Phosphorus Values Over Time – All Subjects Treated with KRN23 (Efficacy Analysis Set)

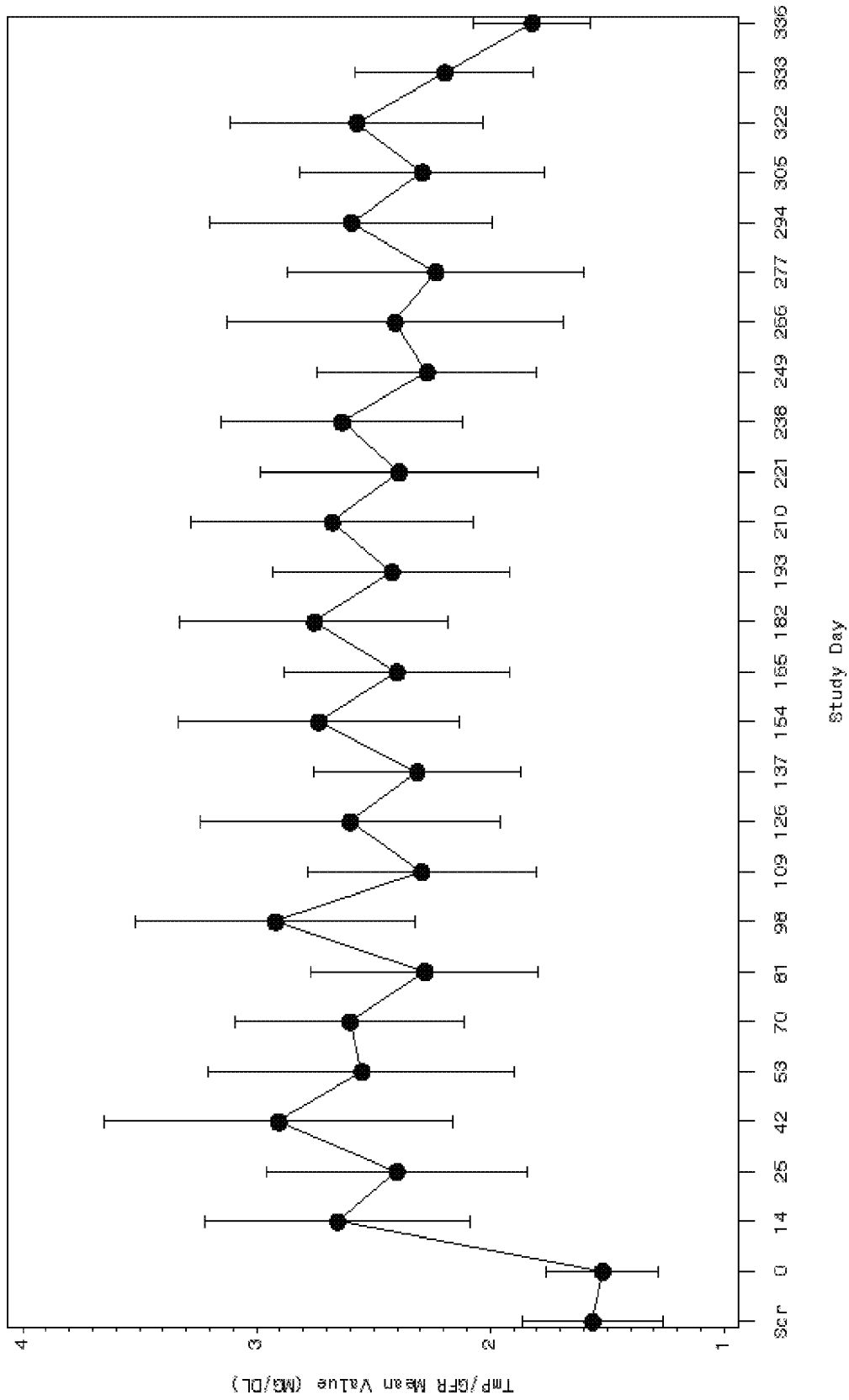
FIG. 13 Mean (± SD) TmP/GFR Levels Over Time - All Subjects Treated with KRN23 (Efficacy Analysis Set)

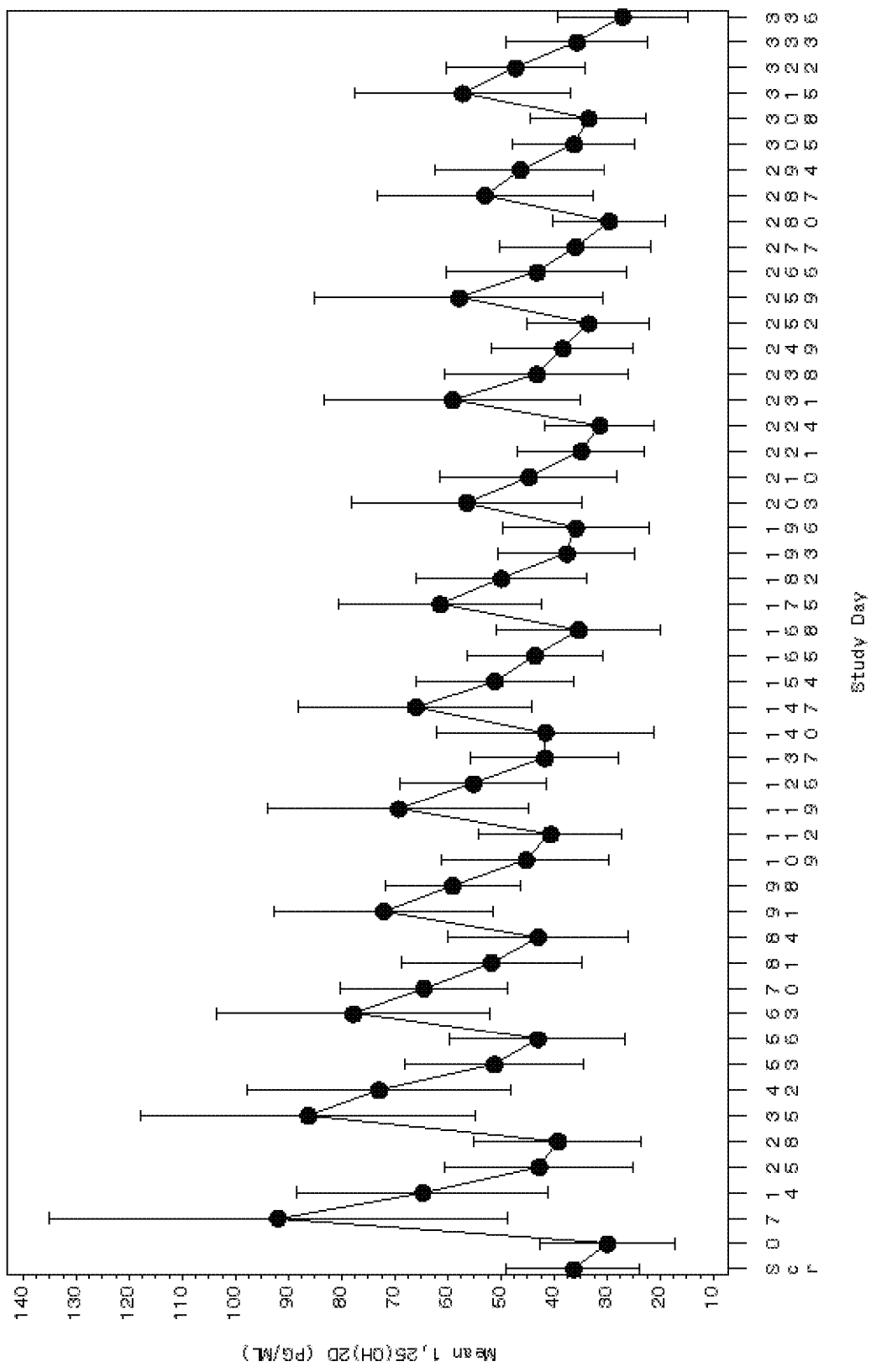
FIG. 14  Mean (± SD) 1,25(OH)₂D Levels Over Time - All Subjects Treated with KRN23 (Efficacy Analysis Set)

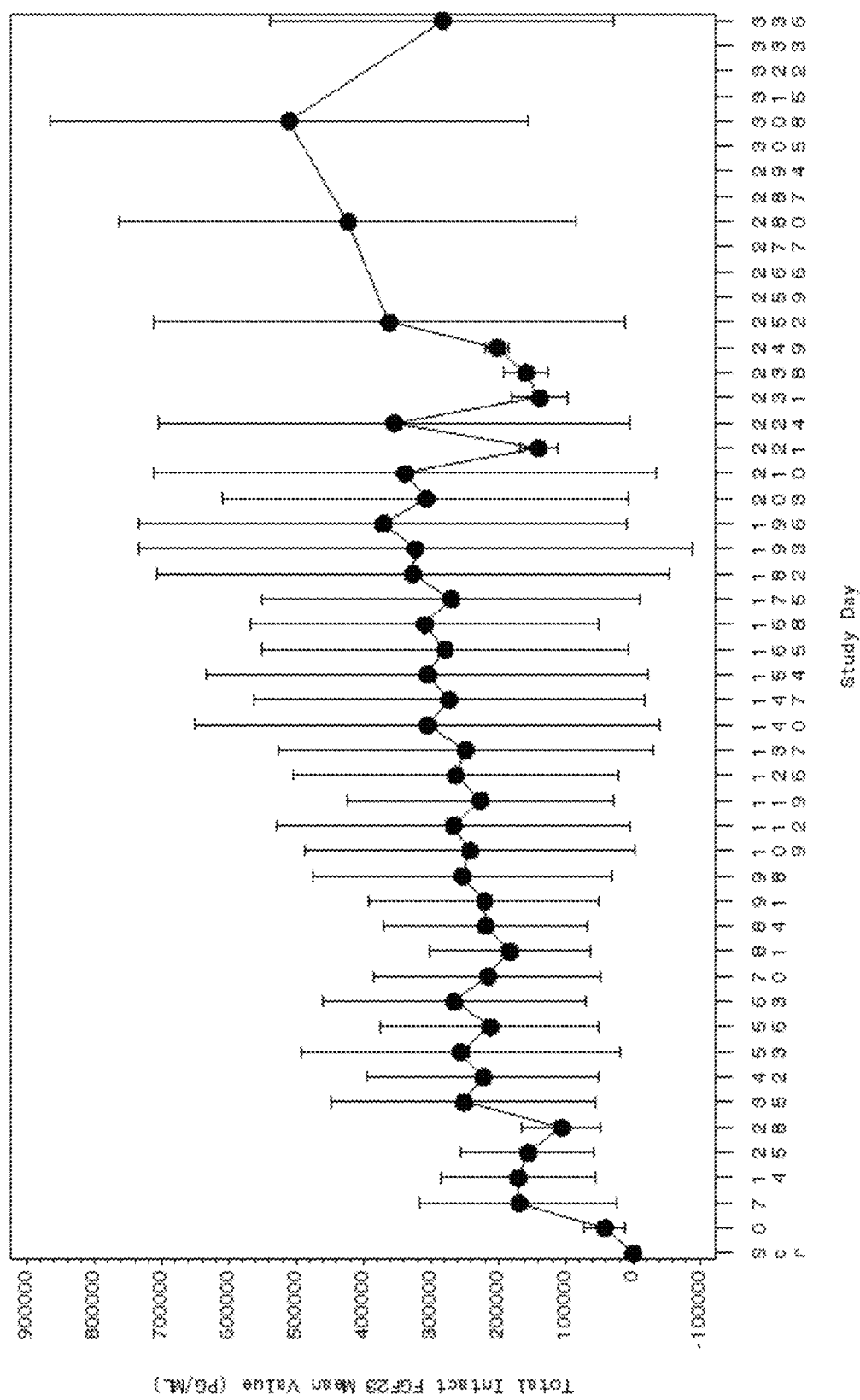
FIG. 15 Mean (± SD) Total Intact FGF23 Values Over Time (Efficacy Analysis Set)

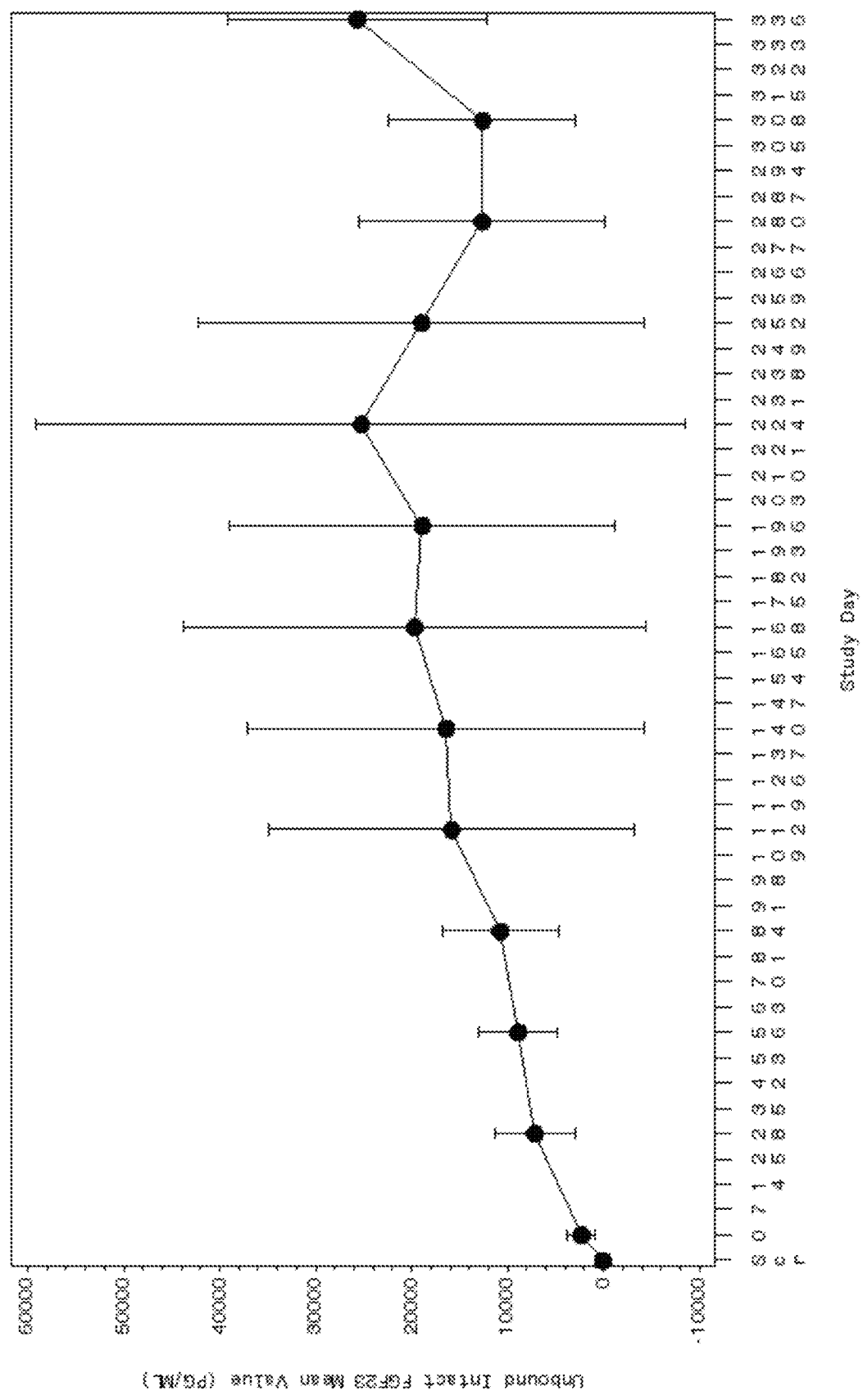
FIG. 16  Mean (±SD) Total Unbound Intact FGF23 (Bottom Panel) Values Over Time (Efficacy Analysis Set)

METHODS FOR TREATING HYPOPHOSPHATEMIC DISORDERS

CROSS-REFERENCE TO RELATED APPLICATIONS

This application is a Continuation Application of U.S. application Ser. No. 14/725,320, filed May 29, 2015, which claims priority to U.S. Provisional Application Ser. No. 62/009,474, filed Jun. 9, 2014, which is herein incorporated by reference in its entirety for all purposes.

FIELD OF THE INVENTION

The present invention relates to compositions comprising an active ingredient regulating bone formation, and methods of using the compositions.

DESCRIPTION OF TEXT FILE SUBMITTED ELECTRONICALLY

The contents of the text file submitted electronically herewith are incorporated herein by reference in their entirety: A computer readable format copy of the Sequence Listing (filename: ULPI_022_02US_SeqList_ST25.txt, date created: Mar. 26, 2020, file size: 28,459 bytes).

BACKGROUND OF THE INVENTION

Fibroblast growth factor-23 (FGF23 or FGF-23) is a hormone that regulates phosphate level through an action on the reabsorption of phosphate from the kidneys. FGF23 was cloned initially from mice using PCR methods based on sequences derived from database searches using sequence homology with FGF15. Human FGF23 was cloned by using sequence homology with mouse FGF23 (Yamashita, T. et al., Biochem. Biophy. Res. Commun., 277: 494-498, 2000).

Recent studies have shed new light on the understanding of phosphate metabolism. Phosphate has important functions in the body and several mechanisms have evolved to regulate phosphate balance including vitamin D, parathyroid hormone and phosphatonins such as FGF23. Disorders of phosphate homeostasis leading to hypo- and hyperphosphataemia are common and have clinical and biochemical consequences.

Despite the previous findings, there remains a need for more effective methods for treating disorders related to abnormal phosphate metabolism, such as disorders related to abnormal FGF23 signaling, and methods for evaluating the efficacy of the treatment. The present invention meets this need and provides compositions and methods for the effective treatment of such disorders.

SUMMARY OF THE INVENTION

The present invention is based in part on the discovery that dosing regimen of anti-FGF23 ligands can be determined based on an understanding of the relationship between phosphate levels and regulated levels of FGF23 within a dosing cycle during chronic administration. Accordingly, the present invention provides methods for determining the dosing regimen of anti-FGF23 ligands. The present invention also provides methods for treating conditions or disorders associated with FGF23. Anti-FGF23 ligands can be used for treating various disorders. In some other embodiments, the disorders are associated with abnormal FGF23 signaling in a subject in need of such treatment. In some other embodiments, the disorders are associated with abnormal FGF23 activity in a subject in need of such treatment. In some other embodiments, the disorders are associated with abnormally high FGF23 activity in a subject in need of such treatment. In some other embodiments, the disorder is selected from the group consisting of, autosomal dominant hypophosphatemic rickets/osteomalachia (ADHR), X-linked hypophosphatemia (XLH), autosomal recessive hypophosphatemic rickets (ARHR), fibrous dysplasia (FD), McCune-Albright syndrome complicated by fibrous dysplasia (MAS/FD), Jansen's metaphyseal chondrodysplasia (Jansen's Syndrome), autosomal dominant polycystic kidney disease (ADPKD), tumor-induced osteomalacia (TIO), chronic metabolic acidosis and ectopic calcification. In some embodiments, the disorder is XLH. In some embodiments, the methods comprise administering an anti-FGF23 ligand to a subject in need of such treatment. In some embodiments, an effective amount of an anti-FGF23 ligand is administered to the subject.

According to one aspect of the present invention, the dosing regimen of the anti-FGF23 ligand can be determined based on one or more PD parameters of the anti-FGF23 ligand in the subject.

The PD parameters of the anti-FGF23 ligand include but are not limited to, serum phosphorus (e.g., AUC serum phosphorus, such as AUC serum phosphorus within a dose interval, or peak and trough serum phosphorus), Tmp/GFR, serum 1,25-dihydroxy vitamin D, and serum 25-hydroxy vitamin D.

In some embodiments, the anti-FGF23 ligand is selected from the group consisting of anti-FGF23 antibodies, FGF23 antisense oligonucleotides, small molecule inhibitors of FGF23, FGF23 antagonists, and combinations thereof. In some embodiments, the anti-FGF23 ligand is an anti-FGF23 antibody.

In some embodiments, the anti-FGF23 ligand comprises one or more CDR sequences selected from SEQ ID NO: 1, SEQ ID NO: 2, SEQ ID NO. 3, SEQ ID NO: 4, SEQ ID NO: 5, and SEQ ID NO. 6.

In some embodiments, the dosing regimen of the anti-FGF23 ligand provides an adequate increase or predetermined production of phosphate over a dosing cycle. In some embodiments, the dosing regimen provides a stable increase of phosphate within a predetermined range of phosphate. In some embodiments, the dosing regimen provides a stable increase in serum phosphorus of about 0.5 to about 1.5 mg/dL above the baseline level of phosphate.

In some embodiments, the dosing regimen of the anti-FGF23 ligand provides sufficient binding agent for an increased bound FGF23 level during chronic anti-FGF23 ligand therapy.

In some embodiments, the dosing regimen comprises a dosing frequency that provides a sustained effect on the NaPi transporter, i.e., without a decline of NaPi transporter activity during a dosing cycle.

In some embodiments, the dosing regimen comprises administering an anti-FGF23 ligand more frequently than a monthly dosing regimen, such as administering an anti-FGF23 ligand every two weeks (i.e., Q2W).

In some embodiments, the dosing regimen provides an increase in bone remodeling.

In yet some other embodiments, the present invention provides methods of treating and/or preventing a disorder by administering about every two weeks an effective amount of an anti-FGF23 ligand to a subject in need of such a treatment. In some embodiments, the administration provides statistically significant therapeutic effect for treating the disorder. In some embodiments, the subject has a disorder selected from the group consisting of, autosomal dominant hypophosphatemic rickets/osteomalacia (ADHR), X-linked hypophosphatemia (XLH), autosomal recessive hypophosphatemic rickets (ARHR), fibrous dysplasia (FD), McCune-Albright syndrome complicated by fibrous dysplasia (MAS/FD), Jansen's metaphyseal chondrodysplasia (Jansen's Syndrome), autosomal dominant polycystic kidney disease (ADPKD), tumor-induced osteomalacia (TIO), chronic metabolic acidosis, and ectopic calcification. In some embodiments, the disorder is ectopic calcification.

According to another aspect of the invention, it provides methods of treating conditions or disorders associated with FGF23. In some embodiments, the methods comprise administering one or more anti-FGF23 ligands according to a dosing regimen determined based on one or more PD parameters of the anti-FGF23 ligands.

According to yet another aspect of the invention, it also provides methods of increasing bone remodeling. In some embodiments, the methods comprise administering to a subject in need of such treatment an effective amount of an anti-FGF23 ligand. In some embodiments, the anti-FGF23 ligand causes an increase of a marker. In some embodiments, the marker is selected from the group consisting of serum Type 1 Pro-collagen/N-terminal (P1NP), carboxy-terminal collagen crosslink (CTX), Osteocalcin, BALP, serum CTx and urine NTX/creatine ratio. In some embodiments, the subject has a disorder selected from the group consisting of, autosomal dominant hypophosphatemic rickets/osteomalachia (ADHR), X-linked hypophosphatemia (XLH), autosomal recessive hypophosphatemic rickets (ARHR), fibrous dysplasia (FD), McCune-Albright syndrome complicated by fibrous dysplasia (MAS/FD), Jansen's metaphyseal chondrodysplasia (Jansen's Syndrome), autosomal dominant polycystic kidney disease (ADPKD), tumor-induced osteomalacia (TIO), chronic metabolic acidosis, and ectopic calcification. In some embodiments, the subject has XLH. In some other embodiments, the method increases bone remodeling associated with one or more conditions caused by abnormal FGF23, e.g., high FGF23 activity and/or level.

BRIEF DESCRIPTION OF THE DRAWINGS

FIG. 1 depicts mean (±SD) serum phosphorus values by study day for all subjects treated with KRN23 in the efficacy analysis during the first Phase I/II clinical trial.

FIG. 2 depicts mean (±SD) TmP/GFR levels by study day for all subjects treated with KRN23 in the efficacy analysis during the first Phase I/II clinical trial.

FIG. 4 depicts scatter plot of TmP/GFR calculated versus TmP/GFR manually read from Nomogram for all subjects treated with KRN23 in the efficacy analysis during the first Phase I/II clinical trial.

FIG. 5 depicts mean (±SD) 1,25(OH)$_2$D Levels (pg/mL) over time for the 4 dosing intervals for all subjects treated with KRN23 in the efficacy analysis during the first Phase I/II clinical trial.

FIG. 6 depicts mean (±SD) total FGF23 and unbound FGF23 values over time in the efficacy analysis during the first Phase I/II clinical trial.

FIG. 11 depicts relationship between KRN23 concentration and change from baseline in serum phosphorus in adult subjects with XLH treated with KRN23 from the population PK-PD model predictions in pharmacokinetic analysis during the first Phase I/II clinical trial.

FIG. 12 depicts mean (±SD) serum phosphorus values over time—all subjects treated with KRN23 for efficacy analysis during the second Phase I/II clinical trial.

FIG. 13 depicts mean (±SD) TmP/GFR levels over time of all subjects treated with KRN23 for efficacy analysis during the second Phase I/II clinical trial.

FIG. 14 depicts mean (±SD) 1,25(OH)$_2$D levels over time of all subjects treated with KRN23 for efficacy analysis during the second Phase I/II clinical trial.

FIG. 15 depicts mean (±SD) total intact FGF23 values over time for efficacy analysis during the second Phase I/II clinical trial.

FIG. 16 depicts mean (±SD) total unbound intact FGF23 values over time for efficacy analysis during the second Phase I/II clinical trial.

DETAILED DESCRIPTION

Definitions

Figure 3A:
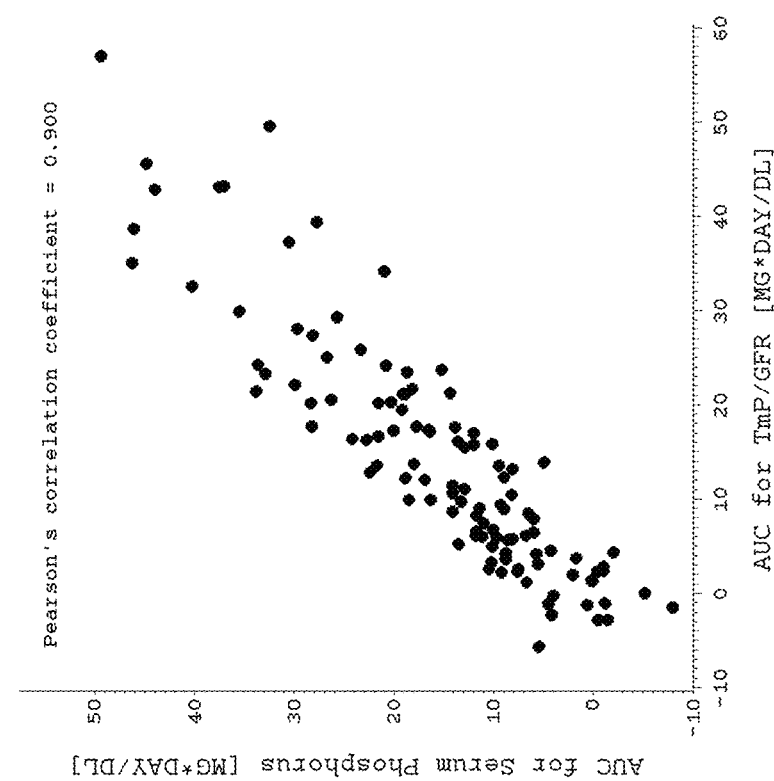
FIGS. 3A and 3B depicts scatter plots of $AUC_{last}$ (FIG. 3A) and $AUC_n$ (FIG. 3B) for serum phosphorus versus $AUC_{last}$ (FIG. 3A) and $AUC_n$ (FIG. 3B) for TmP/GFR in patients treated with KRN23 in the efficacy analysis during the first Phase I/II clinical trial.

The verb "comprise" as is used in this description and in the claims and its conjugations are used in its non-limiting sense to mean that items following the word are included, but items not specifically mentioned are not excluded.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

The invention provides isolated, chimeric, recombinant or synthetic polynucleotide sequences. As used herein, the terms "polynucleotide", "polynucleotide sequence", "nucleic acid sequence", "nucleic acid fragment", and "isolated nucleic acid fragment" are used interchangeably herein and encompass DNA, RNA, cDNA, whether single stranded or double stranded, as well as chemical modifications thereof. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. In some embodiments, the isolated, chimeric, recombinant or synthetic polynucleotide sequences are derived from gene markers of the present invention.

The invention also provides proteins or polypeptides. In some embodiments the proteins or polypeptides are isolated, purified, chimeric, recombinant or synthetic. As used herein, the term "polypeptide" or "protein" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included are, for example, polypeptides containing one or more analogs of an amino acid (including, for example, unnatural amino acids, etc.), as well as other modifications known in the art. Polypeptides can occur as single chains or associated chains. Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). In some embodiments, the sequences of the proteins or polypeptides are derived from gene markers of the present invention.

Single letter amino acid abbreviations used herein have their standard meaning in the art, and all peptide sequences described herein are written according to convention, with the N-terminal end to the left and the C-terminal end to the right.

As used herein, the term "a component in the FGF23 signaling pathway", refers to FGF23, or other components that can modulate the activity of FGF23, directly or indirectly, or components that can be modulated by FGF23, directly or indirectly. Such components include, but are not limited to those described by Sapir-Koren and Livshits (Bone mineralization and regulation of phosphate homeostasis, IBMS BoneKEy, 8:286-300, (2011)), Quarles (FGF23, PHEX, and MEPE regulation of phosphate homeostasis and skeletal mineralization, American Journal of Physiology—Endocrinology and Metabolism Published 1 Jul. 2003, Vol. 285, no. E1-E9), and Martin and Quarles (Evidence for Fgf23 Involvement in a Bone—Kidney Axis Regulating Bone Mineralization and Systemic Phosphate and Vitamin D Homeostasis, Endocrine FGFs and Klothos, Springer Science and Business Media, LLC, landers Bioscience), each of which is herein incorporated by reference in its entirety for all purposes.

As used herein, the term "fibroblast growth factor receptor" or "FGFR" refers to a receptor specific for FGF which is necessary for transducing the signal exerted by FGF to the cell interior, typically comprising an extracellular ligand-binding domain, a single transmembrane helix, and a cytoplasmic domain having tyrosine kinase activity. The FGFR extracellular domain consists of three immunoglobulin-like (Ig-like) domains (D1, D2 and D3), a heparin binding domain and an acidic box.

The term "antigen," as used herein, refers to a molecule capable of being recognized by an antibody. An antigen can be, for example, a peptide or a modified form thereof. An antigen can comprise one or more epitopes.

The term "epitope," as used herein, is a portion of an antigen that is specifically recognized by an antibody. An epitope, for example, can comprise or consist of a portion of a peptide (e.g., a peptide of the invention). An epitope can be a linear epitope, sequential epitope, or a conformational epitope.

As used herein, the term "anti-FGF23 ligand" refers to molecules that inhibit the activity of FGF23 directly or indirectly. The inhibition can happen at the DNA level, transcriptional level, post-transcriptional level, translational level, and/or post-translational level. Such molecules include, but are not limited to, anti-FGF23 antibodies, FGF23 antisense oligonucleotides, small molecule inhibitors of FGF23, FGF23 antagonists as well as any molecule that interacts with one or more components of FGF23 signaling pathway, thereby indirectly inhibiting FGF23.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed $\alpha$, $\delta$, $\epsilon$, $\mu$, and respectively. The subunit structures and three-dimensional configurations of different classes of immunoglobulins are well known. In some embodiments, IgG and/or IgM are used. It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')2 fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies (see, for example, U.S. Pat. No. 4,816,567). Single chain antibodies fall within the scope of the present invention.

By the term "single chain variable fragment (scFv)" is meant a fusion of the variable regions of the heavy and light chains of immunoglobulin, linked together with a short (usually serine, glycine) linker. Single chain antibodies can be single chain composite polypeptides having antigen binding capabilities and comprising amino acid sequences homologous or analogous to the variable regions of an immunoglobulin light and heavy chain (linked VH-VL or single chain Fv (scFv)). Both VH and VL may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the VH and VL chains are known, may be accomplished in accordance with the methods described, for example, in U.S. Pat. Nos. 4,946,778, 5,091,513 and 5,096,815, the entire contents of each of which are incorporated herein by reference.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_H L$ $C_H 2$, and $C_H 3$. The $V_H$ domain is at the amino-terminus of the polypeptide, and the $C_H$ domains are at the carboxyl-terminus, with the $C_H 3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

Three complementarity determining regions are present in the heavy chain variable region, which are a first complementarity determining region (CDR1), a second complementarity determining region (CDR2), and a third complementarity determining region (CDR3). The three complementarity determining regions in the heavy chain variable region are collectively referred to as the heavy chain complementarity determining region. Similarly, three complementarity determining regions are present in the light chain variable region, which are a first complementarity determining region (CDR1), a second complementarity determining region (CDR2), and a third complementarity determining region (CDR3). The three complementarity determining regions in the light chain variable region are collectively referred to as the light chain complementarity determining region. The sequences of these CDRs can be determined by using the methods described in Sequences of Proteins of Immunological Interest, US Dept. Health and Human Services (1991) and the like.

The term "immunologically functional fragment" (or simply "fragment") of an antigen binding protein, e.g., an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, Fab', F(ab')2, Fv, domain antibodies and single-chain antibodies, and can be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

An "Fc" or "Fc region" comprises one or two heavy chain fragments, and can comprise the $C_H 2$ and/or $C_H 3$ domains of an antibody. When two heavy chain fragments are present, the two heavy chain fragments are held together by two or more disulfide bonds and by hydrophobic interactions of the $C_H 3$ domains. An Fc region can be naturally occurring (e.g., a Fc region derived from an IgG1, IgG2, IgG3, IgG4, IgE, IgA, etc.) or can be an engineered sequence comprising one or more (e.g., 1, 2, 3, 4, 5, 6, 7, 8, 9, 10, 11, 12, 13, 14, 15, 16, 17, 18, 19, 20, etc.) mutations, deletions or insertions introduced into a naturally occurring heavy chain fragment or fragments that make up an Fc sequence.

An "Fab' fragment" contains one light chain and a portion of one heavy chain that contains the VH domain and the $C_H 1$ domain and also the region between the $C_H 1$ and $C_H 2$ domains, such that an interchain disulfide bond can be formed between the two heavy chains of two Fab' fragments to form an $F(ab')_2$ molecule.

An "$F(ab')_2$ fragment" contains two light chains and two heavy chains containing a portion of the constant region between the $C_H 1$ and $C_H 2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

As will be understood by those in the art, the immunological binding reagents encompassed by the term "antibody" extend to all antibodies and antigen binding fragments thereof, including whole antibodies, dimeric, trimeric and multimeric antibodies; bispecific antibodies; chimeric antibodies; recombinant and engineered antibodies, and fragments thereof. The term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa (lamda) bodies (scFv-CL fusions); Bispecific T-cell Engager (BiTE) (scFv-scFv tandems to attract T cells); dual variable domain (DVD)-Ig (bispecific format); small immunoprotein (SIP) (kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995).

Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo. In some embodiments, the antibody or antibody fragment comprises an antibody light chain variable region (VL) that comprises three CDR domains and an antibody heavy chain variable region (VH) that comprises three CDR domains. Said VL and VH generally form the antigen binding site.

As used herein, an "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the VH-VL dimer. Collectively, the six hypervariable regions (CDRs) confer antigen-binding specificity to the antibody. However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective. For example, camelid antibodies (Hamers-Casterman et al., 1993; Arbabi Ghahroudi et al., 1997) have an extensive antigen binding repertoire but are devoid of light chains. Also, results with single domain antibodies comprising VH domains alone (Ward et al., 1989; Davies and Riechmann, 1995) or VL domains alone (van den Beucken et al., 2001) show that these domains can bind to antigen with acceptably high affinities. Thus, three CDRs can effectively bind antigen.

It is also known that a single CDR, or two CDRs, can effectively bind antigen. As a first example, a single CDR can be inserted into a heterologous protein and confer antigen binding ability on the heterologous protein, as exemplified by showing that a VH CDR3 region inserted into a heterologous protein, such as GFP, confers antigen binding ability on the heterologous protein (Kiss et al., 2006; Nicaise et al., 2004). It is further known that two CDRs can effectively bind antigen, and even confer superior properties than possessed by the parent antibody. For example, it has been shown (Qiu et al., 2007) that two CDRs from a parent antibody (a VH CDR1 and a VL CDR3 region) retain the antigen recognition properties of the parent molecule but have a superior capacity to penetrate tumors. Joining these CDR domains with an appropriate linker sequence (e.g., from VH FR2) to orientate the CDRs in a manner resembling the native parent antibody produced even better antigen recognition. Therefore, it is known in the art that it is possible to construct antigen binding antibody mimetics comprising two CDR domains (e.g., one from a VH domain and one from a VL domain, for example, with one of the two CDR domains being a CDR3 domain) orientated by means of an appropriate framework region to maintain the conformation found in the parent antibody. Thus, although some antibodies of the invention might comprise six CDR regions (three from a light chain and three from a heavy chain), antibodies with fewer than six CDR regions and as few as one or two CDR regions are encompassed by the invention. In addition, antibodies with CDRs from only the heavy chain or light chain are also contemplated.

Light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds FGF23 can be readily identified by a person skilled in the art. For example, a heavy chain variable region of the invention can be combined with a single light chain variable region or a repertoire of light chain variable regions and the resulting antibodies tested for binding to FGF23. It would be expected that a reasonable number of such combinations of heavy chain variable regions of the invention with different light chain variable regions would retain the ability to bind FGF23.

Similar methods could be used to identify alternative heavy chain variable regions for use in combination with light chain variable regions of the invention. In certain embodiments, the antibody or antibody fragment comprises all or a portion of a heavy chain constant region, such as an IgG1, IgG2, IgG3, IgG4, IgA1, IgA2, IgE, IgM or IgD constant region. In some embodiments, the heavy chain constant region is an IgG1 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies.

"Functional fragment" is a portion of an antibody (partial fragment) and has one or more of the actions of the antibody to the antigen. In other words, it refers to a fragment which retains binding ability to the antigen, reactivity to the antigen, or recognition capability to the antigen. Examples include Fv, disulfide stabilized Fv (dsFv), single chain Fv (scFv), and polymers of these and the like. Stated more specifically, examples include peptides which contain Fab, Fab', F (ab')$_2$, scFv, diabody, dsFv, and CDR (D. J. King., Applications and Engineering of Monoclonal Antibodies., 1998 T. J. International Ltd).

The antibodies of the present invention also includes derivatives of the antibody, such as those derivatives in which radioisotopes, low molecular weight drugs, macromolecular drugs, proteins, and the like is bound chemically or through genetic engineering to the antibody against FGF23 of the present invention or functional fragments of the antibody. The derivatives of the antibody of the present invention can be produced by bonding radioisotopes, low molecular weight drugs, macromolecular drugs, proteins and the like to the amino terminal side or carboxy terminal side of the H chain (heavy chain) or L chain (light chain) of the antibody against FGF23 of the present invention or the functional fragment of the antibody, to a suitable substituted group or side chain in the antibody or functional fragment of the antibody, and further, to a sugar chain in the antibody or functional fragment of the antibody and the like by chemical methods (Koutai Kogaku Nyuumon, Osamu Kanamitsu, Chijin Shokan, 1994) and the like. In addition, the derivative of the antibody bonded with protein is produced by linking the DNA which encodes the antibody against FGF23 of the present invention and the functional fragment of the antibody and the DNA which encodes the protein to be bonded, inserting this DNA into an expression vector, and introducing and expressing the expression vector in a suitable host cell.

In the present invention, "human antibody" is defined as an antibody which is an expression product of an antibody gene derived from humans. Human antibody, as will be described later, can be obtained by introducing the human antibody gene locus and by administering antigen to transgenic animals having the ability to produce human antibody. Examples of these transgenic animals include mice. The method of creation of mice which can produce human antibody is described, for example, in International Publication Number WO 2002/43478.

A "variant" of a polypeptide comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) *SIAM I Applied Math.* 48:1073.

In calculating percent identity, the sequences being compared are aligned in a way that gives the largest match between the sequences. The computer program used to determine percent identity can be, for example, the GCG program package, which includes GAP (Devereux et al., (1984) *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:
Algorithm: Needleman et al., 1970, *J. Mol. Biol.* 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

The terms "treating" and "treatment" as used herein refer to an approach for obtaining beneficial or desired results including clinical results, and may include even minimal changes or improvements in one or more measurable markers of the disease or condition being treated. A treatment is usually effective to reduce at least one symptom of a condition, disease, disorder, injury or damage. Exemplary markers of clinical improvement will be apparent to persons skilled in the art. Examples include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life, etc.

"Prophylaxis," "prophylactic treatment," or "preventive treatment" refers to preventing or reducing the occurrence or severity of one or more symptoms and/or their underlying cause, for example, prevention of a disease or condition in a subject susceptible to developing a disease or condition (e.g., at a higher risk, as a result of genetic predisposition, environmental factors, predisposing diseases or disorders, or the like).

The term "disorder" or "disease" used interchangeably herein, refers to any alteration in the state of the body or one of its organs and/or tissues, interrupting or disturbing the performance of organ function and/or tissue function (e.g., causes organ dysfunction) and/or causing a symptom such as discomfort, dysfunction, distress, or even death to a subject afflicted with the disease.

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

The term "effective amount" refers to the amount of one or more compounds that renders a desired treatment outcome. An effective amount may be comprised within one or more doses, i.e., a single dose or multiple doses may be required to achieve the desired treatment endpoint.

The term "therapeutically effective amount" as used herein, refers to the level or amount of one or more agents needed to treat a condition, or reduce or prevent injury or damage, optionally without causing significant negative or adverse side effects.

A "prophylactically effective amount" refers to an amount of an agent sufficient to prevent or reduce severity of a future disease or condition when administered to a subject who is susceptible and/or who may develop a disease or condition.

According to the methods of the present invention, the term "subject," and variants thereof as used herein, includes any subject that has, is suspected of having, or is at risk for having a disease or condition. Suitable subjects (or patients) include mammals, such as laboratory animals (e.g., mouse, rat, rabbit, guinea pig), farm animals, and domestic animals or pets (e.g., cat, dog). Non-human primates and, preferably, human patients, are included. A subject "at risk" may or may not have detectable disease, and may or may not have displayed detectable disease prior to the diagnostic or treatment methods described herein. "At risk" denotes that a subject has one or more so-called risk factors, which are measurable parameters that correlate with development of a condition described herein, which are described herein. A subject having one or more of these risk factors has a higher probability of developing a condition described herein than a subject without these risk factor(s). One example of such a risk factor is an increase or decrease in a biomarker of the present invention as compared to a clinically normal sample.

In certain embodiments, when measuring parameters or other indicators of treatment, an "increased" or "decreased" amount or level may include a "statistically significant" amount. A result is typically referred to as statistically significant if it is unlikely to have occurred by chance. The significance level of a test or result relates traditionally to the amount of evidence required to accept that an event is unlikely to have arisen by chance. In certain cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med.* 130:1005-13, 1999). In some embodiments, an "increased" or "decreased" amount or level is about 1.1×, 1.2×, 1.3×, 1.4×, 1.5×, 2×, 2.5×, 3×, 3.5×, 4×, 4.5×, 5×, 6×, 7×, 8×, 9×, 10×, 15×, 20×, 25×, 30×, 40×, or 50× more or less the amount of a predetermined standard, or the amount of a determined time point relative to a previous or earlier timepoint.

The human subject treated by a composition of the present invention may show complete response or partial response. Complete Response (CR), as used herein, unless otherwise indicated, refers to disappearance of all measurable and non-measurable symptoms and no appearance of new symptoms in a patient under the treatment. Partial Response (PR), as used herein, unless otherwise indicated, refers to at least one measurable and non-measurable symptom is significantly reduced, or without appearance of new symptom in a patient under treatment.

"Phosphate" is distributed in the soft tissue of body in inorganic form or organic form. Non-osseous phosphates comprise less than 20% of the total body content. The remainder is stored in the bone matrix. Therefore, the skeleton is the major reservoir of phosphate. The normal range for serum phosphorus in adults is about 2.5 to about 4.5 mg/dL, and children is higher and varies with age, e.g., the normal range for serum phosphorus in 5-12 years old children is about 2.9 to about 5.7 mg/dL (Greenberg et al., The normal range of serum inorganic phosphorus and its utility as a discriminant in the diagnosis of congenital hypophosphatemia. J Clin Endocrinol Metab 1960; 20:364-379; Burritt et al., Pediatric reference intervals for 19 biologic variables in healthy children. Mayo Clin Proc 1990; 65:329-336, incorporated by reference in its entirety). When serum phosphate decreases, it is resorbed from bone through the activity of PTH and vitamin D. Kidney is the major organ regulating phosphate homeostasis. Filtered phosphate is reabsorbed within kidney and transported across the renal proximal tubular cell with the help of NaPi-2A and NaPi-2C.

"Parathyroid Hormone" (PTH) is a regulator of serum calcium concentration and serum phosphate concentration. Hypocalcemia stimulates the production of PTH, which can increase the expression of the proximal tubule 25(OH) vitamin D 1-α-Hydroxylase, an enzyme that synthesizes the active form of vitamin D, 1,25(OH)$_2$ vitamin D. 1,25(OH)$_2$ vitamin D increases calcium reabsorption in the renal distal convoluted tubule. The release of calcium from bones into the extracellular fluid is also stimulated by PTH through increased osteoclastic bone resorption. 1,25(OH)$_2$ vitamin D increases intestinal calcium and phosphate absorption, and increases phosphate mobilization from bone by increasing osteoclast activity. Both PTH and vitamin D production is influenced by Fibroblast growth factor (FGF) 23 in negative feedback loops.

"FGF23" is an endocrine regulator of phosphate homeostasis and was originally identified as the mutated gene in patients with the phosphate wasting disorder "autosomal dominant hypophosphatemic rickets" (ADHR) (Anonymous., "Autosomal Dominant Hypophosphataemic Rickets is Associated with Mutations in FGF23," Nat Genet 26(3): 345-348 (2000)). FGF23 inhibits reabsorption of phosphate in the renal proximal tubule by decreasing the abundance of the type II sodium-dependent phosphate transporters NaPi-2A and NaPi-2C in the apical brush border membrane (Baum et al., "Effect of Fibroblast Growth Factor-23 on Phosphate Transport in Proximal Tubules," Kidney Int 68(3):1148-1153 (2005); Perwad et al., "Fibroblast Growth Factor 23 Impairs Phosphorus and Vitamin D Metabolism In Vivo and Suppresses 25-hydroxyvitamin D-1alpha-hydroxylase Expression In Vitro," Am J Physiol Renal Physiol 293(5): F1577-1583 (2007); Larsson et al., "Transgenic mice expressing fibroblast growth factor 23 under the control of the alpha1(I) collagen promoter exhibit growth retardation, osteomalacia, and disturbed phosphate homeostasis," Endocrinology 145(7):3087-3094 (2004)). The phosphaturic activity of FGF23 is down-regulated by proteolytic cleavage at the 176RXXR179 (SEQ ID NO: 11) motif, where "XX" is defined as "HT", corresponding to positions 177 and 178, respectively, of the FGF23 amino acid sequence, producing an inactive N-terminal fragment (Y25 to R179) and a C-terminal fragment (S180 to I251) (Goetz et al., "Molecular Insights into the Klotho-dependent, Endocrine Mode of Action of Fibroblast Growth Factor 19 Subfamily Members," Mol Cell Biol 27(9):3417-3428 (2007)). FGF receptor (FGFR) 1 is the principal mediator of the phosphaturic action of FGF23 (Liu et al., "FGFR3 and FGFR4 do not Mediate Renal Effects of FGF23," J Am Soc Nephrol 19(12):2342-2350 (2008)); Gattineni et al., "FGF23 Decreases Renal NaPi-2a and NaPi-2c Expression and Induces Hypophosphatemia in vivo Predominantly via FGF Receptor 1," Am J Physiol 297(2): F282-F291 (2009)). In addition, Klotho, a protein first described as an aging suppressor (Kuro-o et al., "Mutation of the Mouse Klotho Gene Leads to a Syndrome Resembling Aging," Nature 390(6655):45-51 (1997)), is required as a coreceptor by FGF23 in its target tissue in order to exert its phosphaturic activity (Kurosu et al., "Regulation of Fibroblast Growth Factor-23 Signaling by Klotho," J Biol Chem 281(10):6120-6123 (2006)); Urakawa et al., "Klotho Converts Canonical FGF Receptor into a Specific Receptor for FGF23," Nature 444(7120):770-774 (2006); and Goetz R, et al. (Isolated C-terminal tail of FGF23 alleviates hypophosphatemia by inhibiting FGF23-FGFR-Klotho complex formation. Proc Natl Acad Sci USA. 2009). Klotho constitutively binds the cognate FGFRs of FGF23, and the binary FGFR-Klotho complexes exhibit enhanced binding affinity for FGF23 ((Kurosu et al., "Regulation of Fibroblast Growth Factor-23 Signaling by Klotho," J Biol Chem 281(10):6120-6123 (2006); Urakawa et al., "Klotho Converts Canonical FGF Receptor into a Specific Receptor for FGF23," Nature 444(7120):770-774 (2006)). In co-immunoprecipitation studies, it was demonstrated that the mature, full-length form of FGF23 (Y25 to I251) but not the inactive N-terminal fragment of proteolytic cleavage (Y25 to R179) binds to binary FGFR-Klotho complexes (Goetz et al., "Molecular Insights into the Klotho-dependent, Endocrine Mode of Action of Fibroblast Growth Factor 19 Subfamily Members," Mol Cell Biol 27(9):3417-3428 (2007)). High levels of FGF23 signaling in vitro occur when KL and FGFR1c are co-expressed, and this activity can be blocked by anti-FGF23 antibodies that disrupt FGFR-FGF23-KL associations (Urakawa I, et al. Klotho converts canonical FGF receptor into a specific receptor for FGF23. Nature 2006; 444:770-774; Aono Y, et al. Therapeutic Effects of Anti-FGF23 Antibodies in Hypophosphatemic Rickets/Osteomalacia. J Bone Miner Res. 2009).

FGF23 has the function of reducing phosphate reabsorption in proximal tubule, by reducing expression of the renal vitamin D1-α-hydroxylase and increasing expression of the catabolic 25(OH) D-24-hydroxylase, thus decreasing circulating 1,25(OH)$_2$D concentrations. Overexpression of FGF23 in vivo leads to hypophosphatemia, rickets/osteomalacia, similar to patients with ADHR, X-linked hypophosphatemia (XLH), and tumor-induced osteomalacia (TIO) (Larsson T, et al. Transgenic mice expressing fibroblast growth factor 23 under the control of the alpha1(I) collagen promoter exhibit growth retardation, osteomalacia, and disturbed phosphate homeostasis. Endocrinology 2004; 145: 3087-3094; Shimada T, et al. FGF-23 transgenic mice demonstrate hypophosphatemic rickets with reduced expression of sodium phosphate cotransporter type IIa. Biochem Biophys Res Commun 2004; 314:409-414). On the other hand, 1,25(OH)$_2$D stimulates FGF23 promoter activity in vitro and production in vivo (Kolek O I, et al. 1alpha, 25-Dihydroxyvitamin D3 upregulates FGF23 gene expression in bone: the final link in a renal-gastrointestinal-skeletal axis that controls phosphate transport. Am J Physiol Gastrointest Liver Physiol 2005; 289: G1036-G1042; Liu S, et al. Novel regulators of Fgf23 expression and mineralization in Hyp bone. Mol Endocrinol 2009; 23:1505-1508; Shimada T, et al. FGF-23 is a potent regulator of vitamin D metabolism and phosphate homeostasis. J Bone Miner Res 2004; 19:429-435), suggesting there is a negative feedback process between kidney and bone.

The "Klotho" protein is a 130-kDa single-pass transmembrane protein expressed predominantly in the kidney (Matsumara et al., "Identification of the human klotho gene and its two transcripts encoding membrane and secreted klotho protein," *Biochem Biophys Res Commun* 242(3):626-630 (1998), which is hereby incorporated by reference in its entirety). In addition to the membrane-bound isoform of Klotho, alternative splicing and proteolytic cleavage give rise to two soluble isoforms of Klotho found in the circulation (Imura et al., "Secreted Klotho protein in sera and CSF: implication for post-translational cleavage in release of Klotho protein from cell membrane," *FEBS Lett* 565(1-3): 143-147 (2004); Kurosu et al., "Suppression of aging in mice by the hormone Klotho," *Science* 309(5742):1829-1833 (2005); Matsumura et al., "Identification of the human klotho gene and its two transcripts encoding membrane and secreted klotho protein," *Biochem Biophys Res Commun* 242(3):626-630 (1998); Shiraki-Lida et al., "Structure of the mouse klotho gene and its two transcripts encoding membrane and secreted protein," *FEBS Lett* 424(1-2): 6-10 (1998), which are hereby incorporated by reference in their entirety). Observations suggest that the Klotho gene functions as an aging suppressor gene.

FGFR1, transcript variant 1 is a member of the fibroblast growth factor receptor (FGFR) family that is highly conserved between members and throughout evolution. A full-length representative protein consists of an extracellular region, composed of three immunoglobulin-like domains, a single hydrophobic membrane-spanning segment, and a cytoplasmic tyrosine kinase domain. The extracellular portion of the protein interacts with fibroblast growth factors, setting in motion a cascade of downstream signals, ultimately influencing mitogenesis and differentiation. This particular family member binds both acidic and basic fibroblast growth factors and is involved in limb induction. Mutations in this gene have been associated with Pfeiffer syndrome, Jackson-Weiss syndrome, Antley-Bixler syndrome, osteoglophonic dysplasia, and autosomal dominant Kallmann syndrome. See Itoh et al., "The Complete Amino Acid Sequence of the Shorter Form of Human Basic Fibroblast Growth Factor Receptor Deduced from its cDNA," Biochem Biophys Res Commun 169(2): 680-685 (1990); Dode et al., "Kallmann Syndrome: Fibroblast Growth Factor Signaling Insufficiency?" J Mol Med 82(11):725-34 (2004); Coumoul et al., "Roles of FGF Receptors in Mammalian Development and Congenital Diseases," Birth Defects Res C Embryo Today 69(4):286-304 (2003), which are hereby incorporated by reference in their entirety. Alternatively, spliced variants which encode different protein isoforms have been described; however, not all variants have been fully characterized.

"Human FGF23" has the sequence of SEQ ID NO: 12, and the mouse FGF23 has the sequence of SEQ ID NO: 13. FGF23 is inactivated through intracellular proteolysis at the subtilisin-like proprotein convertase (SPC) site R176HTR179/S180 (SEQ ID NO: 14). Some FGF23 mutants, such as R176Q, R179Q, and R179W, destroy this site and stabilize the full-length active form of the protein, which leads to ADHR symptoms. Human Klotho has the sequence of SEQ ID NO: 15.

In mammals, FGFs mediate their action via a set of four FGF receptors, FGFR1-4, that in turn are expressed in multiple spliced variants, e.g., FGFR1c, FGFR2c, FGFR3c and FGFR4. Each FGF receptor contains an intracellular tyrosine kinase domain that is activated upon ligand binding, leading to downstream signaling pathways involving MAPKs (Erk1/2), RAF1, AKT1 and STATs. (Kharitonenkov et al., (2008) BioDrugs 22:37-44). Several reports suggested that the "c"-reporter splice variants of FGFR1-3 exhibit specific affinity to β-Klotho and could act as endogenous receptor for FGF21 (Kurosu et al., (2007) J. Biol. Chem. 282:26687-26695); Ogawa et al., (2007) Proc. Natl. Acad. Sci. USA 104:7432-7437); Kharitonenkov et al., (2008) J. Cell Physiol. 215:1-7). In the liver, which abundantly expresses both β-Klotho and FGFR4, FGF21 does not induce phosphorylation of MAPK albeit the strong binding of FGF21 to the β-Klotho-FGFR4 complex. In 3T3-L1 cells and white adipose tissue, FGFR1 is by far the most abundant receptor, and it is therefore most likely that FGF21's main functional receptors in this tissue are the β-Klotho-FGFR1c complexes. Alternative splicing of FGFR gene produces multiple FGFR isoforms.

"Hyperphosphatemia" is an electrolyte disturbance in which there is an abnormally elevated level of phosphate in the blood. Often, calcium levels are lowered (hypocalcemia) due to precipitation of phosphate with the calcium in tissues. Average phosphorus levels should be between about 0.81 mmol/L to about 1.45 mmol/L. Signs and symptoms include, but are not limited to, ectopic calcification, secondary hyperparathyroidism, and renal osteodystrophy. Hyperphosphatemia may be caused by impaired renal phosphate excretion and/or massive extracellular fluid phosphate loads. Impaired renal phosphate excretion may be due to hypoparathyroidism (e.g., developmental, autoimmune, after surgery or radiation, or activating mutations of calcium-sensing receptor), parathyroid suppression (e.g., Parathyroid-independent hypercalcemia, vitamin D or vitamin A intoxication, sarcoidosis, other granulomatous diseases, immobilization, osteolytic metastases, milk-alkali syndrome, or severe hypermagnesemia or hypomagnesemia), pseudohypoparathyroidism, acromegaly, tumoral calcinosis, or heparin therapy. Massive extracellular fluid phosphate loads may be due to rapid administration of exogenous phosphate, extensive cellular injury or necrosis (e.g., crush injuries, rhabdomyolysis, hyperthermia, fulminant hepatitis, cytotoxic therapy, or severe hemolytic anemia), or trans-cellular phosphate shifts.

In contrast, hypophosphatemia refers to serum phosphate concentration below the normal range of 2.2 to 4.9 mg/dl (Dwyer et al., "Severe hypophosphatemia in postoperative patients," Nutr Clin Pract 7(6):279-283 (1992); Alon et al., "Calcimimetics as an adjuvant treatment for familial hypophosphatemic rickets," Clin J Am Soc Nephrol 3(3): 658-664 (2008), which are hereby incorporated by reference in their entirety).

Hypophosphatemia may be due to renal phosphate wasting (such as, autosomal dominant hypophosphatemic rickets (ADHR), X-linked hypophosphatemia (XLH), autosomal recessive hypophosphatemic rickets (ARHR), fibrous dysplasia (FD), McCune-Albright syndrome complicated by fibrous dysplasia (MAS/FD), Jansen's metaphyseal chondrodysplasia (Jansen's Syndrome), autosomal dominant polycystic kidney disease (ADPKD), tumor-induced osteomalacia (TIO), and chronic metabolic acidosis), other inherited or acquired renal phosphate wasting disorders, alcoholic and diabetic ketoacidosis, acute asthma, chronic obstructive pulmonary disease (COPD), drug treatment of COPD, sepsis, recovery from organ (in particular, kidney) transplantation, parenteral iron administration, salicylate intoxication, severe trauma, chronic treatment with sucralfate and/or antacids, mechanical ventilation, eating disorder (such as, anorexia nervosa and bulimia nervosa), or the refeeding syndrome.

"Renal phosphate wasting" refers to an inherited or acquired condition in which renal tubular reabsorption of phosphate is impaired. It occurs in approximately 50% of patients with McCune-Albright syndrome (MAS) and fibrous dysplasia of bone (FD). It is reported that serum levels of FGF23 were increased in FD/MAS patients compared with normal age-matched controls and significantly higher in FD/MAS patients with renal phosphate wasting compared with those without, and correlated with disease burden bone turnover markets commonly used to assess disease activity (Riminucci et al., FGF-23 in fibrous dysplasia of bone and its relationship to renal phosphate wasting, J. Clin. Invest. 112:683-692 (2003)).

Methods

According to the present invention, it provides methods of using anti-FGF23 ligands, especially methods of determining the dosing regimen of anti-FGF23 ligands, based on one or more PD parameters of the anti-FGF23 ligands in subjects receiving treatments. In some embodiments, one or more anti-FGF23 ligands are used for the treatment of conditions associated with FGF23, e.g., higher than normal level of FGF23. For example, in some embodiments, anti-FGF23 ligands are used to treat Autosomal dominant hypophosphatemic rickets/osteomalacia (ADHR), X-linked hypophosphatemia (XLH), autosomal recessive hypophosphatemic rickets (ARHR), fibrous dysplasia (FD), McCune-Albright syndrome complicated by fibrous dysplasia (MAS/FD), Jansen's metaphyseal chondrodysplasia (Jansen's Syndrome), autosomal dominant polycystic kidney disease (ADPKD), tumor-induced osteomalacia (TIO), chronic metabolic acidosis and ectopic calcification.

In some other embodiments, the anti-FGF23 ligands are used to treat disorders or conditions associated with hypophosphatemia or renal phosphate wasting.

According to the present invention, anti-FGF23 ligands can include any active ingredient or agent that can modulate, e.g., down regulate the activity of FGF23 and/or one or more components in the FGF23 signaling pathway thereby down regulate the activity of FGF23. In some embodiments, the active agent is a small molecule. In some embodiments, the active agent is a polypeptide, such as an antibody. In some embodiments, the active agent is a polynucleotide, such as siRNA. As used herein, the term activity refers to the activity of a given target at the genomic DNA level, transcriptional level, post-transcriptional level, translational level, post-translational level, including but not limited to, gene copy number, mRNA transcription rate, mRNA abundance, mRNA stability, protein translation rate, protein stability, protein modification, protein activity, protein complex activity, etc.

In some embodiments, the active agent modulates the activity of FGF23. In some embodiments, the active agent modulates gene copy number of a component in the FGF23 signaling pathway. In some embodiments, the active agent can increase or decrease the gene copy number by 0.5×, 1.0×, 1.5×, 2×, 3×, 4×, 5×, 6×, 7×, 8×, 9×, 10×, 100×, 1000×, 10000× or more when compared to the gene copy number before treatment.

In some embodiments, the active agent modulates the mRNA abundance of a component in the FGF23 signaling pathway. In some embodiments, the active agent can increase or decrease the mRNA abundance by 0.5×, 1.0×, 1.5×, 2×, 3×, 4×, 5×, 6×, 7×, 8×, 9×, 10×, 100×, 1000×, 10000× or more when compared to the mRNA abundance before treatment.

In some embodiments, the active agent modulates the protein level of a component in the FGF23 signaling pathway. In some embodiments, the active agent can increase or decrease the protein level by 0.5×, 1.0×, 1.5×, 2×, 3×, 4×, 5×, 6×, 7×, 8×, 9×, 10×, 100×, 1000×, 10000× or more when compared to the protein level before treatment.

In some embodiments, the active agent modulates the mRNA and/or protein activity or stability of a component in the FGF23 signaling pathway. In some embodiments, the active agent can increase or decrease the activity or stability when compared to the stability before treatment.

In some embodiments, the active agent modulates the enzymatic activity of a component in the FGF23 signaling pathway. In some embodiments, the active agent can increase or decrease the enzymatic activity when compared to the stability before treatment.

The activity of a component in the FGF23 signaling pathway can be determined by any suitable methods known to one skilled in the art. In some embodiments, a biological sample is taken from a subject and analyzed. In some embodiments, the biological sample is then assayed for activity of a component in the FGF23 signaling pathway, such as gene amplification number, RNA, mRNA, cDNA, cRNA, protein, etc.

In some embodiments, mRNA from a biological sample is directly used in determining the level of activity. In some embodiments, the level is determined by hybridization. In some embodiments, the RNA is transformed into cDNA (complementary DNA) copy using methods known in the art. In some particular embodiments, the cDNA is labeled with a fluorescent label or other detectable label. The cDNA is then hybridized to a substrate containing a plurality of probes of interest. A probe of interest typically hybridizes under stringent hybridization conditions to at least one DNA sequence of a gene signature. In certain embodiments, the plurality of probes are capable of hybridizing to the sequences derived from the gene biomarkers under the hybridization conditions. In some embodiments, the conditions comprise using 6×SSC (0.9 M NaCl, 0.09 M sodium citrate, pH 7.4) at 65° C. The probes may comprise nucleic acids. The term "nucleic acid" encompasses known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, peptide-nucleic acids (PNAs). Methods for detecting can include but are not limited to RT-PCR, northern blot analyses, gene expression analyses, microarray analyses, gene expression chip analyses, hybridization techniques (including FISH), expression beadchip arrays, and chromatography as well as any other techniques known in the art. Methods for detecting DNA can include but are not limited to PCR, real-time PCR, digital PCR, hybridization (including FISH), microarray analyses, SNP detection assays, SNP genotyping assays and chromatography as well as any other techniques known in the art.

In some embodiments, the protein expression level is used in determining the level of activity. The protein expression level of a component in the FGF23 signaling pathway can be determined by any suitable methods known to one skilled in the art. Any suitable methods of protein detection, quantization and comparison can be used, such as those described in Tschesche (Methods in Protein Biochemistry, ISBN Walter de Gruyter, 2011, ISBN 3110252368, 9783110252361), Goluch et al. (Chip-based detection of protein cancer markers, ProQuest, 2007, ISBN 0549463453, 9780549463450), Speicher (Proteome Analysis: Interpreting the Genome, Elsevier, 2004, ISBN 0080515304, 9780080515304), Albala et al. (Protein Arrays, Biochips and Proteomics, CRC Press, 2003, ISBN 0203911121, 9780203911129), Walker (The Protein Protocols Handbook, Springer, 2002, ISBN 0896039404, 9780896039407), Fung (Protein Arrays: Methods and Protocols, Springer, 2004, ISBN 1592597599, 9781592597598), and Bienvenut (Acceleration and Improvement of Protein Identification by Mass Spectrometry, Springer, 2005, ISBN 1402033184, 9781402033186), each of which is incorporated by reference in its entirety for all purposes. In some embodiments, the protein expression level of biomarkers are detected and measured by immunohistochemistry (IHC), western blot, protein immunostaining, protein immunoprecipitation, immunoeletrophoresis, immunoblotting, BCA assay, spectrophotometry, mass spectrometry or enzyme assay, or combinations thereof. For additional methods related to detection, quantitation and comparison of biomarker levels, see, e.g., Current Protocols in Molecular Biology, Ed. Ausubel, Frederick M. (2010); Current Protocols in Protein Science Last, Ed. Coligan, John E., et al. (2010); Current Protocols in Nucleic Acid Chemistry, Ed. Egli, Martin (2010); Current Protocols in Bioinformatics, Ed. Baxevanis, Andreas D. (2010); and Molecular Cloning: A Laboratory Manual, Third Edition, Sambrook, Joseph (2001), all of which are incorporated herein by reference in their entirety.

In some embodiments, an antibody directed to a component in the FGF23 signaling pathway can be used as an active agent. In some embodiments, an antibody directed to a component in the FGF23 signaling pathway that positively controls FGF23, or an antibody directed to a component in the FGF23 signaling pathway that is positively controlled by FGF23 can be used as an active agent.

In some embodiments, the active agent can directly decrease the FGF23 activity in a human subject. In some embodiments, the active agent can modulate the activity of one or more upstream or downstream components in the signaling pathway thereby decreasing the FGF23 activity in a human subject indirectly. In some embodiments, the active agent can decrease the activity of one or more upstream components that positively regulate FGF23, or increase the activity of one or more upstream components in the signaling pathway that negatively regulate FGF23. In some embodiments, the active agent can decrease the activity of one or more downstream components that are positively regulated by FGF23, or increase the activity of one or more downstream components in the signaling pathway that are negatively regulated by FGF23.

Without wishing to be bound by any particular theory, the agents of the present invention can act through one or more mechanisms. Such mechanisms include, but are not limited to: (1) inhibition of FGF23 activity; (2) inhibition of FGF23-Klotho-FGF receptor complex activity; (3) increasing phosphate reabsorption in proximal tubule; (4) increasing activity of the renal vitamin D1-α-hydroxylase; (5) decreasing the activity of catabolic 25(OH) D-24-hydroxylase; and/or (6) increasing 1,25(OH)$_2$D concentrations.

The active agents can be chemical compounds or compositions, biological molecules, or combinations thereof. In some embodiments, the active agents are small molecules. As used herein, the term "small molecule" refers to a molecule having a molecular weight of less than 500 MW, wherein the drug is a non-peptidyl or peptide agent. In some embodiments, the active agents are antibodies. In some embodiments, the active agents are antibodies. In some embodiments, the active agents are polynucleotides, such as siRNA.

In some embodiments, the active agents contain one or more antibodies that can reduce, inhibit or delay the activity of a component in the FGF23 signaling pathway that positively regulates FGF23, or is positively regulated by FGF23. In some embodiments, the component can be a member of the FGF23-Klotho-FGF receptor complex. In some embodiments, the component is FGF23. In some embodiments, the agent is a monoclonal antibody. In some embodiments, the antibody is an antibody described herein. In some embodiments, an anti-FGF23 ligand is an active agent comprising one or more anti-FGF23 CDRs, such as those of SEQ ID NOs. 1-6.

In some embodiments, the active agent is an antibody against human FGF23 or a functional fragment thereof, comprising a heavy chain variable region having any one of complementarity determining region (CDR) 1 shown by the amino acid sequence of SEQ ID NO: 1, CDR2 shown by the amino acid sequence of SEQ ID NO: 2 and CDR3 shown by the amino acid sequence of SEQ ID NO: 3, or a heavy chain variable region having at least two or all of the three heavy chain CDRs.

In some embodiments, the antibody against human FGF23 or a functional fragment thereof, comprises a light chain variable region having any one of CDR1 shown by the amino acid sequence of SEQ ID NO: 4, CDR2 shown by the amino acid sequence of SEQ ID NO: 5 and CDR3 shown by the amino acid sequence of SEQ ID NO: 6, or a light chain variable region having at least two or all of the three light chain CDRs.

In some embodiments, the FGF23 antibody contains CDRs with amino acid sequence of SEQ ID NO: 1, 2, 3, 4, 5, and/or 6. In some embodiments, the FGF23 antibody comprises the heavy chain variable region comprising SEQ ID NO: 16 and the light chain variable region comprising SEQ ID NO: 17. In some embodiments, the FGF23 antibody is KRN23 having the heavy chain of SEQ ID NO: 7 and the light chain of SEQ ID NO: 8. In some embodiments, the FGF23 antibody is C10 having the heavy chain of SEQ ID NO: 9 and the light chain of SEQ ID NO: 10.

The CDR sequence of the antibody of the present invention is not specifically limited. In some embodiments, the antibody of the present invention is an antibody comprising any one or more CDRs, more preferably three CDRs of the heavy chain, and even more preferably six CDRs of the CDR sequences represented by SEQ ID NOs: 1 through 6. The amino acid sequence other than the CDR is not specifically limited. In some other embodiments, anti-FGF23 antibodies include so called CDR transplantation antibodies, wherein the amino acid sequence other than the CDR is derived from other antibodies, and particularly antibodies in other species. Among these, a humanized antibody or human antibody, wherein the amino acid sequence other than the CDR is derived from human, is preferred. An addition, deletion, substitution and/or insertion of 1 amino acid residue or more can be introduced into the FR according to need. A publicly known method can be applied as the method for producing a humanized antibody or human antibody.

In some embodiments, the antibody against FGF23 is anyone of those described in U.S. Pat. Nos. 7,314,618, 7,223,563, 7,745,406, 7,947,810, 7,223,563, 7,745,406 or 7,947,810, or in U.S. Patent Application Publication Nos. 20120064544 or 20110182913, each of which is incorporated by reference in its entirety for all purposes.

In some embodiments, the active agents are siRNA. For example, antisense RNA, ribozyme, dsRNAi, RNA interference (RNAi) technologies can be used in the present invention to target RNA transcripts of one or more component in the FGF23 signaling pathway. Antisense RNA technology involves expressing in, or introducing into, a cell an RNA molecule (or RNA derivative) that is complementary to, or antisense to, sequences found in a particular mRNA in a cell. By associating with the mRNA, the antisense RNA can inhibit translation of the encoded gene product.

RNA interference (RNAi) is the process of sequence-specific, post-transcriptional gene silencing or transcriptional gene silencing in animals and plants, initiated by double-stranded RNA (dsRNA) that is homologous in sequence to the silenced gene. The RNAi technique is discussed, for example, in Elibashir, et al., Methods Enzymol. 26:199 (2002); McManus & Sharp, Nature Rev. Genetics 3:737 (2002); PCT application WO 01/75164; Martinez et al., Cell 110:563 (2002); Elbashir et al., supra; Lagos-Quintana et al., Curr. Biol. 12:735 (2002); Tuschl et al., Nature Biotechnol. 20:446 (2002); Tuschl, Chembiochem. 2:239 (2001); Harborth et al., J. Cell Sci. 114:4557 (2001); et al., EMBO J. 20:6877 (2001); Lagos-Quintana et al., Science 294:8538 (2001); Hutvagner et al., loc cit, 834; Elbashir et al., Nature 411:494 (2001).

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of a target gene, or an opposite strand replication intermediate, or the anti-genomic plus strand or non-mRNA plus strand sequences of the target gene.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

In yet other embodiments, anti-FGF23 ligands used in the present invention can be provided in pharmaceutical compositions comprising one or more of the active agents used in the present invention and a vehicle, such as an artificial membrane vesicle (including a liposome, lipid micelle and the like), microparticle or microcapsule.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anesthetics, preservatives and buffering agents can also be included in the injectable solution or suspension.

In some embodiments, the delivery systems suitable include time-release, delayed release, sustained release, or controlled release delivery systems. In some embodiments, a composition of the present invention can be delivered in a controlled release system, such as sustained-release matrices. Non-limiting examples of sustained-release matrices include polyesters, hydrogels (e.g., poly(2-hydroxyethyl-methacrylate) as described by Langer et al., 1981, J. Biomed. Mater. Res., 15:167-277 and Langer, 1982, Chem. Tech., 12:98-105), or poly(vinylalcohol)], polylactides (U.S. Pat. No. 3,773,919; EP 58,481), copolymers of L-glutamic acid and gamma ethyl-L-glutamate (Sidman et al., 1983, Biopolymers, 22:547-556), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid (EP 133,988). In some embodiments, the composition may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990). In some embodiments, the composition may be administered through subcutaneous injection.

In some embodiments, the release of the composition occurs in bursts. Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme.

In some embodiments, the release of the composition is gradual/continuous.

Examples of systems in which release of the inhibitor is gradual and continuous include, e.g., erosional systems in which the composition is contained in a form within a matrix and effusional systems in which the composition is released at a controlled rate, e.g., through a polymer. Such sustained release systems can be e.g., in the form of pellets, or capsules.

Other embodiments of the compositions administered according to the invention incorporate particulate forms, protective coatings, protease inhibitors or permeation enhancers for various routes of administration, such as parenteral, pulmonary, nasal and oral.

The pharmaceutical compositions of the present invention can be used alone or in combination with other pharmaceutical compositions. The pharmaceutical compositions of the present invention may be administered, together or separately, in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. In some embodiments, the a pharmaceutical composition of the present invention may be administered to a subject together with an addition pharmaceutical composition suitable for treating disorders associated with abnormal phosphorus status, FGF23 signaling, or bone formation.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

In some embodiments, administration of a composition of the present invention may be carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The inhibitor may be administered with a pharmaceutically-acceptable carrier.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

According to the present invention, the dosing regimen of an anti-FGF23 ligand can be determined based on one or more PD parameters of the anti-FGF23 ligand. In some embodiments, the dosing regimen of an anti-FGF23 ligand includes, without any limitation, the amount per dose, frequency of dosing, e.g., per day, week, or month, total amount per dosing cycle, dosing interval, dosing variation, pattern or modification per dosing cycle, maximum accumulated dosing, or warm up dosing, or any combination thereof. In some other embodiments, the dosing regimen of an anti-FGF23 ligand includes frequency of dosing, e.g., per month.

In yet some other embodiments, the dosing regimen includes a pre-determined or fixed amount per dose in combination with a frequency of such dose. For example, the dosing regimen of an anti-FGF23 antibody includes a fixed amount of anti-FGF23 antibody per dose in combination with the frequency of such dose of antibody being administered to a subject. In some embodiments, the fixed amount of anti-FGF23 antibody per dose includes without any limitation about 0.001 mg/kg of body weight, about 0.002 mg/kg of body weight, about 0.003 mg/kg of body weight, about 0.004 mg/kg of body weight, about 0.005 mg/kg of body weight, about 0.006 mg/kg of body weight, about 0.007 mg/kg of body weight, about 0.008 mg/kg of body weight, about 0.009 mg/kg of body weight, about 0.01 mg/kg of body weight, about 0.02 mg/kg of body weight, about 0.03 mg/kg of body weight, about 0.04 mg/kg of body weight, about 0.05 mg/kg of body weight, about 0.06 mg/kg of body weight, about 0.07 mg/kg of body weight, about 0.08 mg/kg of body weight, about 0.09 mg/kg of body weight, about 0.1 mg/kg of body weight, about 0.2 mg/kg of body weight, about 0.3 mg/kg of body weight, about 0.4 mg/kg of body weight, about 0.5 mg/kg of body weight, about 0.6 mg/kg of body weight, about 0.7 mg/kg of body weight, about 0.8 mg/kg of body weight, about 0.9 mg/kg of body weight, about 1 mg/kg of body weight, about 2 mg/kg of body weight, about 3 mg/kg of body weight, about 4 mg/kg of body weight, about 5 mg/kg of body weight, about 6 mg/kg of body weight, about 7 mg/kg of body weight, about 8 mg/kg of body weight, about 9 mg/kg of body weight, about 10 mg/kg of body weight, about 15 mg/kg of body weight, about 20 mg/kg of body weight, about 30 mg/kg of body weight, about 35 mg/kg of body weight, about 40 mg/kg of body weight, about 45 mg/kg of body weight, about 50 mg/kg of body weight, about 60 mg/kg of body weight, about 70 mg/kg of body weight, about 80 mg/kg of body weight, about 90 mg/kg of body weight, about 100 mg/kg of body weight, about 200 mg/kg of body weight, about 300 mg/kg of body weight, about 400 mg/kg of body weight, about 500 mg/kg of body weight or more.

In some other embodiments, the fixed amount of anti-FGF23 antibody per dose includes without any limitation about 0.05 mg/kg, 0.1 mg/kg, 0.3 mg/kg, 0.6 mg/kg, or 1.0 mg/kg or 2.0 mg/kg e. g., administered SC.

According to the present invention, the dosing regimen of an anti-FGF23 ligand can be determined based on one or more PD parameters of the anti-FGF23 ligand. In some embodiments, the dosing regimen of an anti-FGF23 ligand is determined based on one or more PD parameters of the anti-FGF23 ligand in a population of subjects treated with the anti-FGF23 ligand. In some other embodiments, the size of the population includes at least 20, 30, 40, 50, or more subjects. In some other embodiments, the size of the population provides statistical significance for the analysis of one or more PD parameters. In some other embodiments, the dosing regimen of an anti-FGF23 ligand is determined based on one or more PD parameters of the anti-FGF23 ligand in the single subject treated with the anti-FGF23 ligand. For example, one or more PD parameters can be measured in a subject treated with an anti-FGF23 ligand for a period of time, then the dosing regimen of the subject can be modified based on the subject's PD parameters measured. In other words, one or more PD parameters can be used to "tailor" the dosing regimen of a subject under treatment with an anti-FGF23 ligand.

In some other embodiments, the dosing regimen of an anti-FGF23 ligand is determined based on a pre-determined level or activity of one or more PD parameters. For example, such pre-determined level or activity can be obtained via treating a population of patients with an anti-FGF23 ligand and determining the desired or standard level or activity for one or more PD parameters.

In general, pharmacodynamics (PD) is the study of the biochemical and physiological effects of drugs on the body or on microorganisms or parasites within or on the body and the mechanisms of drug action and the relationship between drug concentration and effect. Pharmacodynamics is often summarized as the study of what a drug does to the body. The effect of an active agent of the present invention can be determined by monitoring the changes of one or more PD parameters associated with the treatment, so an effective dosage regimen of the active agent can be determined. In some embodiments, the dosing regimen is determined without any input from one or more PK parameters or without giving consideration of one or more PK parameters. In some other embodiments, the dosing regimen is modified even though one or more PK parameters indicate that the dosing regimen is already sufficient or adequate.

PD parameters that can be used in the present invention in order to determine the dosage regime of an active agent of the present invention include, but are not limited to, serum phosphorus, TmP/GFR (renal tubular maximum reabsorption rate of phosphate to glomerular filtration rate), maximum TmP/GFR, serum 1,25-dihydroxy vitamin D, and serum 25-hydroxy vitamin D. In some embodiments, serum phosphorus includes AUC serum phosphorus, e.g., $AUC_{last}$, $AUC_{inf}$ or $AUC_n$ within a dose interval or peak and trough serum phosphorus.

In some embodiments, the dosing regimen of an active agent of the present invention is determined based on one or more PD parameters to provide a sufficient binding agent for any changes in FGF23 levels during chronic anti-FGF23 ligand therapy. In some other embodiments, the dosing regimen of an active agent of the present invention is determined based on one or more PD parameters to provide an FGF23 level or activity within at least 60%, 70%, 80%, 85%, 90%, or 95%, 98%, 100%, 105%, 110%, 115%, or 120% of the normal FGF23 level or activity, e.g., of an adult or child. In some other embodiments, the dosing regimen of an active agent of the present invention is determined based on one or more PD parameters to maintain a steady level or activity of FGF23, e.g., that does not deviate away from the normal FGF23 level or activity for more than 2%, 3%, 4%, 5%, 6%, 7%, 8%, 9%, 10%, 15%, 20%, or 30% of the normal FGF23 level or activity.

In some embodiments, the dosing regimen is determined based on one or more PD parameters to achieve normalization or stabilization of one or more PD parameters. In some embodiments, the dosing regimen is determined to keep one or more PD parameters as much above the baseline level as possible, as long as possible, and/or as stable as possible, without raising any toxicity issue. For example, the dosing regimen is determined to keep serum phosphorus at a stable level above baseline, e.g., with minimum or acceptable variability. In yet some other embodiments, the dosing regimen is determined to keep one or more PD parameters around a predetermined level, e.g., predetermined standard level. For example, in one embodiment, the dosing regimen is determined to keep serum phosphorus at a predetermined standard level, e.g., a stable increase of about 0.5 to 1.5 mg/dL above baseline. In another embodiment, the dosing regimen is determined to keep serum phosphorus at a predetermined standard level, e.g., a stable increase of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3 mg/dL above baseline.

In some embodiments, the dosing regimen is determined to provide a sustained effect on NaPi transporter, e.g., without a substantial decline of NaPi transporter activity during a dosing cycle. In some embodiments, the dosing regimen is determined to provide a steady NaPi transporter level or activity, e.g., a NaPi transporter level or activity that does not deviate away from the normal NaPi transporter level or activity for more than, e.g., 1%, 2%, 3%, 4%, 5%, 6%, 7%, 8%, 9%, 10%, 15%, 20%, or 30% of the normal NaPi transporter level or activity. In some embodiments, the dosing regimen is determined to provide an increase in bone remodeling.

As used herein, when the level of a PD parameter goes towards the level of a predetermined standard level, it is called normalization. As used herein, when the level of a PD parameter reduces its variation from the level of a predetermined standard level, it is called stabilization.

As used herein, the term "predetermined standard level" refers to levels obtained from standardized data or data set representing the average, representative features or characteristics of one or more PD parameters providing effective dosing regimen for a particular anti-FGF23 ligand therapy in a specific population of subjects. Such features or characteristics include, but are not limited to, transcript abundance, transcript stability, transcription rate, translation rate, post-translation modification, protein abundance, protein stability, and/or protein enzymatic activity, etc. In some embodiments, the specific population of subjects are consisting of about 5, about 10, about 20, about 50, about 100, about 200, about 300, about 400, about 500, about 1000, about 5000, about 10K, or more individual subjects. The predetermined activity profile can be a standardized data set or a data set collected before, during, or after the specific population of subjects has been all exposed to a drug. In some embodiments, the specific population is consisting of subjects under effective dosing regimen of an anti-FGF23 ligand.

In some embodiments, the PD parameter is serum phosphorus. In some embodiments, the dosage regimen is determined based on Area Under the Curve (AUC) of serum phosphorus. In some embodiments, the AUC is $AUC_{last}$, $AUC_{inf}$, or $AUC_n$. In some embodiments, the PD parameter is the AUC of serum phosphorus within a dosage interval. In some embodiments, the PD parameter is the peak and trough serum phosphorus. In some embodiments, the dosage regimen is determined to maintain a serum phosphorus level during the treatment that is close to, or above a predetermined serum phosphorus level. In some embodiments, the dosage regimen is determined to provide an adequate, stable increase of phosphorus in the patient during a dosing cycle when compared to the baseline level in the patient. In some embodiments, the dosage regimen is determined to maintain a relatively stable serum phosphorus level above the baseline level in the patient. For example, in some embodiments, a stable increase in serum phosphorus of about 0.5 to about 1.5 mg/dL is likely to be sufficient.

In some embodiments, when the patient is an adult, the baseline serum phosphorus level is about 2.5 to about 4.5 mg/dL. In some embodiments, when the patient is a 5-12 year old child, the baseline serum phosphorus level is about 2.9 to about 5.7 mg/dL. In some embodiments, when the patient is an adult, the predetermined serum phosphorus level is about 0.5 mg to 1.5 mg/dL higher than the baseline, e.g., of about 2.5 to about 4.5 mg/dL. In some embodiments, when the patient is a 5-12 year old child, the predetermined serum phosphorus level is about 0.5 mg to 1.5 mg/dL higher than the baseline of about 2.9 to about 5.7 mg/dL. In some embodiments, depending on the age of the patient, the predetermined serum phosphorus level is about 2.5 mg/dL, about 2.6 mg/dL, about 2.7 mg/dL, about 2.8 mg/dL, about 2.9 mg/dL, about 3.0 mg/dL, about 3.1 mg/dL, about 3.2 mg/dL, about 3.3 mg/dL, about 3.4 mg/dL, about 3.5 mg/dL, about 3.6 mg/dL, about 3.7 mg/dL, about 3.8 mg/dL, about 3.9 mg/dL, about 4.0 mg/dL, about 4.1 mg/dL, about 4.2 mg/dL, about 4.3 mg/dL, about 4.4 mg/dL, about 4.5 mg/dL, about 4.6 mg/dL, about 4.7 mg/dL, about 4.8 mg/dL, about 4.9 mg/dL, about 5.0 mg/dL, about 5.1 mg/dL, about 5.2 mg/dL, about 5.3 mg/dL, about 5.4 mg/dL, about 5.5 mg/dL, about 5.6 mg/dL, about 5.7 mg/dL, about 5.8 mg/dL, about 5.9 mg/dL, about 6.0 mg/dL, about 6.1 mg/dL, about 6.2 mg/dL, about 6.3 mg/dL, about 6.4 mg/dL, about 6.5 mg/dL, about 6.6 mg/dL, about 6.7 mg/dL, about 6.8 mg/dL, about 6.9 mg/dL, about 7.0 mg/dL, about 7.1 mg/dL, about 7.2 mg/dL, about 7.3 mg/dL, about 7.4 mg/dL, about 7.5 mg/dL, about 7.6 mg/dL, about 7.7 mg/dL, about 7.8 mg/dL, about 7.9 mg/dL, or more. In some other embodiments, the dosing regimen of an active agent of the present invention is determined based on one or more PD parameters to provide a serum phosphorus level or activity within at least 60%, 70%, 80%, 85%, 90%, or 95%, 98%, 100%, 105%, 110%, 115%, 120%, or more of the normal serum phosphorus level or activity, e.g., of an adult or child. In some other embodiments, the dosing regimen of an active agent of the present invention is determined based on one or more PD parameters to maintain a steady level or activity of serum phosphorus, e.g., that does not deviate away from the normal serum phosphorus level or activity for more than 2%, 3%, 4%, 5%, 6%, 7%, 8%, 9%, 10%, 15%, 20%, 30%, or more of the normal serum phosphorus level or activity.

In some embodiments, the PD parameter is Tmp/GFR (the ratio of the renal tubular maximum reabsorption rate of phosphate to glomerular filtration rate, see Barth et al., Ann Clin Biochem 2000; 37: 79-81). In some embodiments, the PD parameter is the peak and trough Tmp/GFR. In some embodiments, the dosing regimen is determined to maintain a Tmp/GFR during the treatment that is close to, or above a predetermined Tmp/GFR. In some embodiments, the dosing regimen is determined to provide an adequate increase of Tmp/GFR in the patient during a dosing cycle when compared to the baseline level in the patient. In some embodiments, the dosing regimen is determined to maintain a relatively stable Tmp/GFR above the baseline level in the patient. In some embodiments, the predetermined Tmp/GFR is about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or more.

In some embodiments, the PD parameter is serum 1,25-dihydroxy vitamin D. In some embodiments, the PD parameter is the peak and trough serum 1,25-dihydroxy vitamin D. In some embodiments, the dosing regimen is determined with the goal to maintain a serum 1,25-dihydroxy vitamin D during the treatment that is close to, similar to, or above a predetermined serum 1,25-dihydroxy vitamin D. In some embodiments, the dosing regimen is determined to provide an adequate increase of serum 1,25-dihydroxy vitamin D in the patient during a dosing cycle when compared to the baseline level in the patient. In some embodiments, the dosing regimen is determined to maintain a relatively stable serum 1,25-dihydroxy vitamin D above the baseline level in the patient. In some embodiments, the predetermined serum 1,25-dihydroxy vitamin D is about 40 pg/ML, about 45 pg/ML, about 50 pg/ML, about 55 pg/ML, about 60 pg/ML, about 65 pg/ML, about 70 pg/ML, about 75 pg/ML, about 80 pg/ML, about 85 pg/ML, about 90 pg/ML, about 95 pg/ML, about 100 pg/ML, about 105 pg/ML, about 110 pg/ML, about 115 pg/ML, about 120 pg/ML, about 125 pg/ML, about 130 pg/ML, about 135 pg/ML, about 140 pg/ML, about 145 pg/ML, about 150 pg/ML, about 155 pg/ML, about 160 pg/ML, about 165 pg/ML, about 170 pg/ML, about 175 pg/ML, about 180 pg/ML, about 185 pg/ML, about 190 pg/ML, about 195 pg/ML, about 200 pg/ML, or more.

In some embodiments, the PD parameter is serum 25-hydroxy vitamin D. In some embodiments, the PD parameter is the peak and trough serum 25-hydroxy vitamin D. In some embodiments, the dosing regimen is determined with the goal to maintain a serum 25-hydroxy vitamin D during the treatment that is close to, similar to, or above a predetermined serum 25-hydroxy vitamin D. In some embodiments, the dosage regime is determined to provide an adequate increase of serum 25-hydroxy vitamin D in the patient during a dosing cycle when compared to the baseline level in the patient. In some embodiments, the dosage regime is determined to maintain a relatively stable serum 25-hydroxy vitamin D above the baseline level in the patient. In some embodiments, the predetermined serum 25-hydroxy vitamin D is about 25 nmol/L, about 26 nmol/L, about 27 nmol/L, about 28 nmol/L, about 29 nmol/L, about 30 nmol/L, about 31 nmol/L, about 32 nmol/L, about 33 nmol/L, about 34 nmol/L, about 35 nmol/L, about 36 nmol/L, about 37 nmol/L, about 38 nmol/L, about 39 nmol/L, about 40 nmol/L, about 41 nmol/L, about 42 nmol/L, about 43 nmol/L, about 44 nmol/L, about 45 nmol/L, about 46 nmol/L, about 47 nmol/L, about 48 nmol/L, about 49 nmol/L, about 50 nmol/L, about 51 nmol/L, about 42 nmol/L, about 53 nmol/L, about 54 nmol/L, about 55 nmol/L, about 56 nmol/L, about 57 nmol/L, about 58 nmol/L, about 59 nmol/L, about 60 nmol/L, about 61 nmol/L, about 62 nmol/L, about 63 nmol/L, about 64 nmol/L, about 65 nmol/L, about 66 nmol/L, about 67 nmol/L, about 68 nmol/L, about 69 nmol/L, about 70 nmol/L, about 71 nmol/L, about 72 nmol/L, about 73 nmol/L, about 74 nmol/L, about 45 nmol/L, about 76 nmol/L, about 77 nmol/L, about 78 nmol/L, about 79 nmol/L, about 80 nmol/L, or more.

In some embodiments, the dosing regimen comprises administering anti-FGF23 ligand more frequently than a dosing regimen determined based on one or more PK parameters. In some other embodiments, the dosing regimen comprises administering anti-FGF23 ligand, e.g., anti-FGF23 antibody more frequently than a monthly dosing regimen. For example, the dosing regimen comprises administrating an anti-FGF23 ligand, e.g., anti-FGF23 antibody about every 3 days, about every 5 days, about every week, about every 10 days, about every 2 weeks, about every 17 days, about every three weeks, about every 25 days or more.

According to another aspect of the present invention, it provides methods for treating FGF23 related disorders via administering one or more anti-FGF23 ligands according to a dosing regimen determined based on one or more PD parameters. In some embodiments, the FGF23 related disorders include any condition or disorder directly or indirectly related to FGF23 or one or more components of FGF23 signaling pathway. For example, in one embodiment the FGF23 related disorder is XLH or TIO. In some other embodiments, the dosing regimen includes using an anti-FGF23 antibody twice per month, e.g., at a fixed dose.

The present invention also provides methods of treating FGF23 related disorders, e.g., via increasing bone remodeling. In some embodiments, the disorders are bone disorders. In some embodiments, the methods comprise inducing bone remodeling in a patient in need of the treatment. In some embodiments, the bone remodeling is induced by an anti-FGF23 ligand, such as an anti-FGF23 antibody. In some embodiments, the administration provides statistically significant therapeutic effect for treating the disorder. In some embodiments, the anti-FGF23 ligand causes an increase of a marker in the patient compared to the baseline level of the marker. In some embodiments, a marker is selected from the group consisting of Serum Type 1 Pro-collagen/N-terminal (P1NP), carboxy-terminal collagen crosslink (CTX), Osteocalcin, BALP, serum CTx and urine NTX/creatine ratio.

In general, bone remodeling involves a series of highly regulated steps that depend on the interactions of the mesenchymal osteoblastic lineage and the hematopoietic osteoclastic lineage. The initial "activation" stage involves the interaction of osteoclast and osteoblast precursor cells which leads to the differentiation, migration, and fusion of the large multinucleated osteoclasts. Bone remodeling is systematically regulated by hormones, including PTH, 1,25-dihydroxy vitamin D, and calcitonin, and several other systemic hormones such as growth hormone, glucocorticoids, and estrogen. Local regulators of bone remodeling include, but are not limited to, cytokines (IL-1, TNF, LI-6, IL-11, ODF, IL-4, IL-13, IL-18, IFN, OPG, and IL-1ra), prostaglandins, osteoclast differentiation factor, colony-stimulating factors (e.g., M-CSF and GM-CSF), leukotrienes, nitric oxide, and growth factors (e.g., IGF, TGFβ, FGF, PDGF, and PTHrP).

The present invention also provides methods of treating and/or preventing a FGF23 related disorder by administering an effective amount of an anti-FGF23 ligand to a subject in need of such a treatment with a dosing regimen more frequent than a monthly dosing regimen, such as an every two weeks dosing regimen. In some embodiments, anti-FGF23 ligand is administered to a subject about every 1, 1.5, 2, 2.5, 3, or 3.5 weeks. In some embodiments, the subject has a disorder associated with abnormal FGF23 signaling, such as disorders selected from the group consisting of, autosomal dominant hypophosphatemic rickets/osteomalachia (ADHR), X-linked hypophosphatemia (XLH), autosomal recessive hypophosphatemic rickets (ARHR), fibrous dysplasia (FD), McCune-Albright syndrome complicated by fibrous dysplasia (MAS/FD), Jansen's metaphyseal chondrodysplasia (Jansen's Syndrome), autosomal dominant polycystic kidney disease (ADPKD), tumor-induced osteomalacia (TIO), chronic metabolic acidosis, and ectopic calcification. In some embodiments, the disorder is ectopic calcification.

The present invention also provides methods of controlling serum phosphate levels. In some embodiments, the methods comprise administrating an anti-FGF23 ligand to a subject in need of such a treatment. In some embodiments, the methods comprise administrating an anti-FGF23 ligand to a subject with a dosing regimen more frequent than a monthly dosing regimen, such as an every two weeks dosing regimen. In some embodiments, anti-FGF23 ligand is administered to a subject about every 1, 1.5, 2, 2.5, 3, or 3.5 weeks. In some embodiments, the methods stabilize or normalize the serum phosphate level in the subject. In some embodiments, the methods minimize the swing of the serum phosphate level, for example, to keep the serum phosphate level close to a predetermined level.

The following examples illustrate various aspects of the invention. The examples should, of course, be understood to be merely illustrative of only certain embodiments of the invention and not to constitute limitations upon the scope of the invention.

EXAMPLES

Example 1—First Phase I/II, Open-Label, Repeat-Dose, Dose-Escalation Study of KRN23 in Adult Subjects with X-Linked Hypophosphatemia Synopsis:

Investigators and Study Centers: A total of 32 subjects were enrolled at 6 sites in the United States and Canada Clinical Phase of Development: Phase 1/2.

Primary Objective: The primary objective of this study was to assess the safety and efficacy of repeat-doses of KRN23 subcutaneous (SC) administration in adult subjects with X-linked hypophosphatemia (XLH).

Secondary Objective: The secondary objectives of this study were to evaluate the effects of repeat-doses of KRN23 SC administration on pharmacodynamics (PD), pharmacokinetics (PK), immunogenicity, and quality of life (QoL).

Bone Substudy Objective: To evaluate the effects of repeat-doses of KRN23 SC administration compared to placebo on bone mineral density and bone quality.

Study Design and Methodology: This was a Phase I/II, open-label, dose-escalation and multicenter study of KRN23 in adult subjects with XLH. The study design consisted of 3 periods: Screening, On-treatment, and Follow-up. During the Screening period, all subjects underwent a Screening visit (the maximum duration of the Screening period was 30 days). Following the Screening visit (Visit 1), all eligible subjects were registered at Baseline (Day 0) into the On-treatment period and the starting dose of KRN23 0.05 mg/kg SC was administered. Subjects were treated with up to 4 doses (1 dose every 28 days) of KRN23 using stepwise dose-escalation from 0.05 mg/kg→0.1 mg/kg→0.3 mg/kg→0.6 mg/kg. Intra-subject dose-escalation was based on serum phosphorus levels guided by a dose-escalation algorithm and other safety observations (i.e., adverse event [AE] monitoring, safety laboratory parameters, immunogenicity, and physical examination findings). Upon completion of the treatment period, subjects underwent a final assessment at the clinic during the Follow-up period (maximum of 10 days).

A bone substudy was planned in a subset of subjects to evaluate the effects of single-blind KRN23 versus placebo on various bone parameters. Subjects underwent evaluation of additional eligibility criteria for participation in this substudy and additional clinical assessments, inclusive of peripheral quantitative computed tomography (pQCT) and dual-energy X-ray absorptiometry (DXA) scan at Baseline and at the end of the study (Day 120). A biopsy of the iliac crest was to be performed for subjects in this substudy who entered the extension study (second Phase I/II clinical trial). The Sponsor terminated the bone substudy due to slow accrual.

Diagnosis: Male and female subjects at least 18 years of age with a documented clinical diagnosis of XLH and intact fibroblast growth factor 23 (FGF23) level >30 pg/mL, renal tubular maximum reabsorption rate of phosphate to glomerular filtration rate (TmP/GFR)<2.0 mg/dL, eGFR≥60 mL/min (using Cockcroft-Gault formula), and corrected serum calcium level <10.8 mg/dL (if serum albumin was <4.0 g/dL).

Number of Subjects (planned and analyzed): Approximately 42 subjects were planned; 33 subjects were screened for enrollment (30 in the open-label portion of the study; 3 in the bone substudy); 1 of the 3 subjects screened in the bone substudy did not meet eligibility criteria and was discontinued from the study prior to treatment assignment.

TABLE 1

Subject Disposition

| | Open-label | Bone Substudy | | Total |
|---|---|---|---|---|
| | KRN23 N = 30 | KRN23 N = 1 | Placebo N = 1 | KRN23 N = 31 |
| Enrolled | 30 | 1 | 1 | 31 |
| Safety Analysis Set[a] | 27 (90.0) | 1 (100.0) | 1 (100.0) | 28 (90.3) |
| Efficacy Analysis Set[b] | 26 (86.7) | 1 (100.0) | 1 (100.0) | 27 (87.1) |
| Completion of Therapy | 25 (83.3) | 1 (100.0) | 1 (100.0) | 26 (83.9) |
| Primary Reason for Withdrawal | | | | |
| Subject Withdrawal of Consent[c] | 2 (6.7) | 0 | 0 | 2 (6.5) |
| Adverse Event 2 (6.7)d 0 0 2 (6.5) | 2 (6.7)[d] | 0 | 0 | 2 (6.5) |
| Subject Did Not Meet Inclusion/Exclusion Criteria[e] | 1 (3.3) | 0 | 0 | 1 (3.2) |

[a]All subjects who received at least one dose of KRN23 or placebo
[b]All subjects who received at least one dose of KRN23 or placebo and had completed at least one 28-day postdose evaluation.
[c]Subject 0207 and 0212 withdrew consent prior to the first dose of KRN23.
[d]Subject 0105 discontinued due to an adverse event that began prior to dosing and Subject 0206 discontinued due to a TEAE (injection site urticaria).
[e]This subject is a screen failure.

Test Product, Dose and Mode of Administration, Batch Number:

KRN23 for SC injection: KRN23 0.05, 0.1, 0.3 or 0.6 mg/kg administered SC to the abdomen.

Open-label portion: 10 mg/mL in a 5-mL single-use vial (Batch Number: YU008B).

Bone substudy: 10 mg/mL in a 5-mL single-use vial (Batch Number: YU008E).

Comparative Agent, Dose, and Mode of Administration, Batch Number:

Open-label portion: None

Bone substudy: KRN23 placebo for SC administration to the abdomen (Batch number: PYU120413A).

Duration of Treatment: The duration of treatment was up to 110 days. The total duration of the study was approximately 150 days for subjects who entered the extension study, and was planned to be 195 days for subjects who did not enter the extension study.

Endpoints:

Efficacy: The primary efficacy endpoint was the number and percentage of subjects with postdose serum phosphorus levels ≤2.5 mg/dL; >2.5 mg/dL but ≤3.5 mg/dL, >3.5 mg/dL but ≤4.5 mg/dL; and >4.5 mg/dL.

Pharmacodynamic: Secondary PD endpoints included the changes from Baseline in:

Serum phosphorus; the area under the concentration time curve (AUC) from Baseline; the time interval of serum phosphorus levels >2.5 mg/dL.

TmP/GFR and serum 1,25-dihydroxy vitamin D [1,25 $(OH)_2D$].

Serum 25-hydroxy vitamin D [25(OH) D], total calcium, ionized calcium, calcitonin, intact parathyroid hormone (iPTH); 2-hour urinary measures of tubular reabsorption of phosphate (TRP), calcium/creatinine ratio, fractional excretion of calcium (FECa); and 24-hour urinary measures of phosphorus, calcium, creatinine, and calcium/creatinine ratio.

Sex hormones: estradiol, testosterone, free testosterone and sex hormone binding globulin (SHBG).

Bone formation biomarkers (bone alkaline phosphatase [BALP], procollagen type 1 N-propeptide [P1NP], and osteocalcin) and bone resorption biomarkers (carboxy-terminal cross-linked telopeptide of type 1 collagen [CTx]) and osteocalcin and amino terminal cross-linked telopeptide of type 1 collagen (urinary NTx).

Pharmacokinetic:

Characterize the PK parameters for KRN23 following multiple-dose SC administration.

Characterize the population PK of KRN23 dose levels from cumulative dosing.

Quality of Life:

Changes from Baseline in patient-reported outcomes (PROs) based on the Study 36-item Short Form, Version 2 (SF-36v2) and Western Ontario and McMaster Osteoarthritis Index (WOMAC).

Safety: Safety included the number and percentage of subjects with adverse events, by severity and relationship to study drug, and the clinically significant changes from Baseline in clinical laboratory evaluations (hematology, chemistry, and urinalysis), vital signs, physical and neurological examinations, cardiac computed tomography (CT)/coronary calcium scoring and aortic calcium scoring, renal ultrasound, electrocardiogram (ECG); and anti-KRN23 antibody assessment. In addition, changes in bone parameters in the forearm and tibia, as measured by pQCT, and changes in bone mineral density and other bone parameters in the lumbar spine and proximal femur, as measured by DXA scan, were assessed in the bone substudy.

Statistical Methods: Absolute and change from Baseline for continuous data were summarized descriptively including the number of observations, mean, standard deviation, median, minimum and maximum. Categorical variable were summarized using frequency counts and percentages. All data summaries were presented for the following treatment groups: open-label treatment (KRN23), single-blind treatment in the bone substudy (KRN23 and placebo) and total KRN23. Pharmacodynamic parameters measured included serum phosphorus levels, TmP/GFR, and serum 1,25(OH)$_2$D along with other biochemical parameters. Area under the curve for the change from baseline in these pharmacodynamic parameters were calculated for the 120 days of treatment or up to last measured time point before withdrawal (AUC$_{last}$) and for each of 4 dosing intervals (AUC1, AUC2, AUC3 and AUC4), where AUCn was the AUC from baseline (i.e., before first dose) for the dosing interval "n". The number and percentage of subjects reporting treatment-emergent adverse events (TEAEs) were evaluated across treatment arms.

Pharmacokinetic and PK-PD Methods: Descriptive statistics were used for serum KRN23 concentration data and PK parameters. Serum KRN23 samples were analyzed using non-compartmental methods. PK parameters (area under the serum concentration time curve from zero to last measured concentration [AUClast], area under the serum concentration-time curve from zero to infinity [AUCinf], apparent volume of distribution [V/F], apparent clearance [CL/F], and terminal elimination half-life after 4th dosing interval [t½]) were estimated using subject serum concentrations for all accumulated doses from Days 1 to 120. In addition, during each dosing interval n, area under the serum concentration-time curve for n-th dosing interval [AUCn], maximum serum concentration [Cmax, n], predose serum concentration (Cmin, n), and time to peak plasma concentration [tmax, n] were estimated. Scatter plots were generated to explore the PK-PD correlation using AUCn and AUClast for PK and PD measures. Concentration (serum KRN23) and effect (serum phosphorus increase from baseline) relationship was described by an empirical Emax model.

Overall study design and plan: This Phase I/II, open-label, dose-escalation multicenter study planned to enroll approximately 42 male and female adult subjects with XLH. Of the 42 subjects, 18 were planned to be in bone substudy. Subjects participating in the open-label portion of the study received up to four doses of KRN23 (0.05, 0.1, 0.3, and 0.6 mg/kg) administered subcutaneously (SC) every 28-days over a 120-day period. All subjects received the starting dose of KRN23 0.05 mg/kg SC. Intra-subject step-wise dose escalation of KRN23 was based on serum phosphorus levels guided by a dose-escalation algorithm and safety evaluations (i.e. AE monitoring, safety laboratory parameters, immunogenicity, and physical examination findings). Subjects participating in the bone substudy were randomized to either single-blind KRN23 or Placebo and received up to four doses of KRN23 (0.05, 0.1, 0.3, and 0.6 mg/kg) administered SC every 28-days over a 120-day period.

Study Medications: Subjects received KRN23 via SC injection(s) to the abdomen (avoiding a 1-inch radius surrounding the umbilicus) on dosing days: Days 0, 28, 56 and 84, using stepwise dose-escalation from 0.05 mg/kg→0.1 mg/kg→0.3 mg/kg→0.6 mg/kg. Subjects returned on Days 3, 7, 12, 18 and 26 of each dosing cycle (4 dosing cycles) for scheduled clinical, laboratory, PK and PD assessments. All the visits were conducted in a fasted state (i.e., refrain from eating and drinking, other than water) for at least 8-hours prior to the study visit.

Disease Characteristics at baseline: For subjects in the efficacy analysis, Baseline disease characteristics including the levels of serum phosphorus, TmP/GFR, 1,25(OH)2D, and intact FGF23 for all subjects in the Efficacy Analysis Set are presented in the table below. Overall, mean serum phosphorus and TmP/GFR levels at Baseline were below the lower limit of the normal reference range. At Baseline, the overall mean 1,25(OH)$_2$D level was within the normal reference range for all subjects. Baseline FGF23 levels ranged from 52.8 to 4620 pg/mL.

TABLE 2

Baseline Disease Characteristics (Efficacy Analysis Set)

| Characteristic | Open-label Treatment KRN23 N = 26 | Bone Substudy KRN23 N = 1 | Bone Substudy Placebo N = 1 | Total KRN23 N = 27 |
|---|---|---|---|---|
| FGF23 (pg/mL) | | | | |
| n | 26 | 1 | 1 | 27 |
| Mean (SD) | 291.2 (886.24) | 52.8 (NA) | 86.6 (NA) | 282.4 (870.24) |
| Min, Max | (56.4, 4620.0) | (52.8, 52.8) | (86.6, 86.6) | (52.8, 4620.0) |
| Serum phosphorus (mg/dL) | | | | |
| n | 26 | 1 | 1 | 27 |
| Mean (SD) | 1.89 (0.34) | 2.0 (NA) | 1.6 (NA) | 1.89 (0.33) |
| Min, Max | (1.2, 2.8) | (2.0, 2.0) | (1.6, 1.6) | (1.2, 2.8) |
| TmP/GFR (mg/dL)[a] | | | | |
| n | 26 | 1 | 1 | 27 |
| Mean (SD) | 1.61 (0.37) | 1.45 (NA) | 1.25 (NA) | 1.60 (0.36) |
| Min, Max | (0.84, 2.26) | (1.45, 1.45) | (1.25, 1.25) | (0.84, 2.26) |
| Serum 1,25(OH)$_2$D (pg/mL) | | | | |
| n | 23 | 1 | 1 | 24 |
| Mean (SD) | 36.3 (14.52) | 42.0 (NA) | 67.0 (NA) | 36.6 (14.25) |
| Min, Max | (10, 62) | (42, 42) | (67, 67) | (10, 62) |
| Serum total calcium (mg/dL) | | | | |
| n | 26 | 1 | 1 | 27 |
| Mean (SD) | 9.10 (0.38) | 9.30 (NA) | 9.30 (NA) | 9.11 (0.38) |
| Min, Max | (8.5, 10.2) | (9.3, 9.3) | (9.30, 9.30) | (8.5, 10.2) |
| Serum iPTH (pg/mL) | | | | |
| n | 26 | 1 | 1 | 27 |
| Mean (SD) | 82.2 (32.74) | 74.0 (NA) | 77.0 (NA) | 81.9 (32.15) |
| Min, Max | (38, 143) | (74, 74) | (77, 77) | (38, 143) |
| BALP (µg/L) | | | | |
| n | 26 | 1 | 1 | 27 |
| Mean (SD) | 28.1 (12.96) | 34.4 (NA) | 20.7 (NA) | 28.3 (12.77) |
| Min, Max | (8.2, 52.4) | (34.4, 34.4) | (20.7, 20.7) | (8.2, 52.4) |
| 24-hr urine calcium (mg/24 hr) | | | | |
| n | 26 | 1 | 1 | 27 |
| Mean (SD) | 91.4 (65.66) | 30.0 (NA) | 54.0 (NA) | 89.1 (65.46) |
| Min, Max | (11, 253) | (30, 30) | (54, 54) | (11, 253) |
| 24-hr urine creatinine (g/24 hr) | | | | |
| n | 26 | 1 | 1 | 27 |
| Mean (SD) | 1.31 (0.62) | 1.23 (NA) | 1.04 (NA) | 1.31 (0.61) |
| Min, Max | (0.54, 3.01) | (1.23, 1.23) | (1.04, 1.04) | (0.54, 3.01) |
| 2-hr calcium/creatinine ratio, (mg/g creatinine) | | | | |
| n | 26 | 1 | 1 | 27 |
| Mean (SD) | 49.4 (38.59) | 7.0 (NA) | 36.0 (NA) | 47.8 (38.71) |
| Min, Max | (11, 192) | (7, 7) | (36, 36) | (7, 192) |

1,25(OH)$_2$D = 1,25-dihydroxyvitamin D;
BALP = bone alkaline phosphatase;
FGF23 = fibroblast growth factor 23;
hr = hour;
iPTH = intact parathyroid hormone;
Max = maximum;
Min = minimum;
NA = not applicable;
SD = standard deviation;
TmP/GFR = renal tubular maximum reabsorption rate of phosphate to glomerular filtration rate.
[a]Normal range: 2.5-4.3 for TmP/GFR?

Pharmacokinetic/Pharmacodynamic Sampling: Blood samples for the assessment of PK of KRN23 were collected from all subjects according to the sampling schedule shown in Table 3 below. Serum samples were analyzed for KRN23 concentrations using validated bioanalytical methods.

TABLE 3

Pharmacokinetic Sampling Schedule

| Dosing Cycle | Day relative to dose* | PK Sample Time |
|---|---|---|
| 1 | 0 | Pre-dose |
|  | 3 | At clinic visit |
|  | 7 | At clinic visit |
|  | 12 | At clinic visit |
|  | 18 | At clinic visit |
|  | 26 | At clinic visit |
| 2 | 28 or Day 0 for 2nd dosing cycle | Pre-dose |
|  | 3 | At clinic visit |
|  | 7 | At clinic visit |
|  | 12 | At clinic visit |
|  | 18 | At clinic visit |
|  | 26 | At clinic visit |

TABLE 3-continued

Pharmacokinetic Sampling Schedule

| Dosing Cycle | Day relative to dose* | PK Sample Time |
|---|---|---|
| 3 | 56 or Day 0 for 3rd dosing cycle | Pre-dose |
| | 3 | At clinic visit |
| | 7 | At clinic visit |
| | 12 | At clinic visit |
| | 18 | At clinic visit |
| | 26 | At clinic visit |
| 4 | 84 or Day 0 for 4th dosing cycle | Pre-dose |
| | 3 | At clinic visit |
| | 7 | At clinic visit |
| | 12 | At clinic visit |
| | 18 | At clinic visit |
| | 26 | At clinic visit |
| Follow up visit/ Early withdrawal | 120 or Day 36 for 4th dosing cycle/Early withdrawal | At clinic visit |

*±3 days window for each visit

Samples for the assessment of PD parameters were collected on dosing days (Days 0, 28, 56 and 84), on Days 3, 7, 12, 18 and 26 of each dosing cycle, and Day 120 (follow-up visit/early withdrawal). In addition, blood samples for measurements of bone biomarkers were collected at baseline (Day 0), at predose time in each dosing cycle (Days 28, 56 and 84) and at the follow-up visit (Day 120).

Drug Concentration Measurements: Serum samples were analyzed for KRN23 at Kyowa Hakko Kirin California, Inc. (KKC) formerly Kirin Pharma USA, Inc., using a validated sandwich Enzyme Linked Immunosorbant Assay (ELISA) method. The lower limit of quantification (LLOQ) for the KRN23 assay was 50 ng/mL. The standard curve had a range of 50-3000 ng/mL for KRN23. All blood and urine samples for PD parameters were analyzed at a central laboratory using available commercial assay kits and/or validated assay methods.

SUMMARY OF RESULTS

Exposure: A total of 28 subjects were treated with KRN23 (27 in the open-label portion of the study and 1 in the bone substudy) and 1 subject was treated with placebo in the bone substudy. The mean total dose of KRN23 administered was 0.05±0.00 mg/kg, 0.10±0.01 mg/kg, 0.28±0.06 mg/kg, and 0.48±0.16 mg/kg during dosing intervals 1, 2, 3, and 4, respectively. One subject in the placebo group in the bone substudy received all 4 doses of placebo.

Study Population: Among the 28 subjects treated with KRN23, the median age was 41.9 years (range: 19 to 66 years); the majority (67.9%; 19/28) were women, and nearly all (96.4%; 27/28) were white/Caucasian and 1 was Black/African American/African Caribbean. The median height of subjects treated with KRN23 was 149.7 cm (range: 121.9 to 170.2 cm) and median weight was 70.1 kg (range: 46.4 to 121.9 kg). The median body mass index of subjects treated with KRN23 was 30.7 kg/m2 (range 19.7 to 67.6 kg/m2). The overall, mean serum phosphorus and TmP/GFR levels at Baseline were below the lower limit of the normal reference range. At Baseline, the overall mean 1,25(OH)$_2$D level was within the normal reference range for subjects treated with KRN23. Baseline FGF23 levels ranged from 52.8 to 4620.0 pg/mL for subjects treated with KRN23.

Efficacy Results: The proportion of KRN23-treated subjects with serum phosphorus levels >2.5 to ≤3.5 mg/dL increased from 3.7% at Baseline (Day 0 in the first dosing interval) to 14.8%, 37.0%, 74.1%, and 70.4% on Day 7 (the time of maximum effect) in the first, second, third, and fourth dosing intervals, respectively. Serum phosphorus levels did not exceed 4.5 mg/dL in any subject at any time point.

Pharmacodynamic Analyses:

Actual sampling times were used for the calculation of the PK parameters. PK parameters for each dosing cycle were estimated based on observed PK profiles in that cycle and the PK parameters for all doses were estimated based on total dose received during the 4 dosing cycles. The following PK parameters were determined for KRN23 from the serum concentration-time data by non-compartmental analysis method:

| Parameter | Definition |
|---|---|
| $AUC_{last}$ | Area under the serum concentration-time curve from time 0 to the time of last measurable concentration over all the dosing cycles (Day 120 or early withdrawal) determined using the linear trapezoidal rule |
| $AUC_{inf}$ | Area under the serum concentration-time curve from time 0 to infinity over all the dosing cycles determined using the linear trapezoidal rule |
| $AUC_n$ | Area under the serum concentration-time curve during n-th dosing cycle |
| $AUC_{\%Extrap}$ | Percentage of AUC inf based on extrapolation |
| $C_{max,n}$ | Maximum observed serum concentration during n-th dosing cycle |
| $C_{min,n}$ | Predose observed serum concentration at the end of n-th dosing cycle |
| $t_{max,n}$ | Time of maximum observed serum concentration during n-th dosing cycle |
| $t_{1/2}$ | Terminal elimination half-life after 4th dosing cycle calculated as $\ln 2/\lambda z$ where $\lambda z$ is the rate constant associated with elimination phase |
| CL/F | Apparent serum clearance calculated as total Dose during 120 days of treatment/$AUC_{inf}$ |
| $V_z/F$ | Apparent volume of distribution based on terminal elimination phase calculated as CL/F/$\lambda z$ after 4th dosing cycle |

For purpose of AUC computations, missing serum levels were not imputed by interpolation between adjacent points. All serum concentrations below the lower limit of quantification of the assay were treated as zero.

The $AUC_1$, $AUC_2$, $AUC_3$ and $AUC_4$ were estimated in Dosing Cycle 1 (Day 0 to Day 28), Dosing Cycle 2 (Day 28 to Day 56), Dosing Cycle 3 (Day 56 to Day 84), and Dosing Cycle 4 (Day 84 to Day 120), respectively.

PK analyses for serum KRN23 concentrations were conducted using noncompartmental analysis method with Phoenix™ WinNonlin® (Version 6.3, Pharsight—A Certara™ Company, Mountain View, Calif.). Graphical displays were produced by SigmaPlot (Systat Software, Inc., Point Richmond, Calif.).

Pharmacodynamic Results:

Mean KRN23 dose increased with each successive dose from 0.05 mg/kg SC for the first dose (starting dose per protocol) to 0.48±0.16 mg/kg for the fourth dose.

Mean serum phosphorus achieved maximum levels by Day 7 after each dose then declined and did not reach pre-dose levels prior to subsequent doses. Increases in serum phosphorus were clinically meaningful in magnitude, particularly after the third and fourth doses.

Peak and trough (pre-dose) mean serum phosphorus levels as well as $AUC_n$ increased with successive doses. The mean maximum serum phosphorus levels increased from 2.21±0.33 mg/dL after the first dose to 3.03±0.42 mg/dL after the fourth dose.

TmP/GFR results followed the same pattern as that observed for serum phosphorus. The mean maximum TmP/GFR after the first dose was 1.93±0.45 mg/dL; this increased to 2.97±0.67 mg/dL after the fourth dose. The magnitude of increase in TmP/GFR was similar to those in serum phosphorus and was clinically meaningful.

Mean serum 1,25(OH)$_2$D levels increased to maximum levels between Days 3 and 7 after each dose and then returned to near the baseline level prior to the next dose. Otherwise, the patterns observed were the same as those seen with serum phosphorus and TmP/GFR.

There was no correlation between baseline levels of FGF23 and serum phosphorus. Similarly, increases in serum phosphorus were not correlated with baseline FGF23 levels.

No meaningful effect of KRN23 treatment was observed on the mean changes from Baseline for the other serum and urine PD parameters. Mean values for other serum and urine PD parameters were unchanged after KRN23 dosing compared to Baseline. Serum parameters included 25(OH)D, total calcium, ionized calcium, calcitonin, iPTH, estradiol, free testosterone, total testosterone, and SHBG. Urine markers included 2-hour measures of TRP, calcium/creatinine ratio, and FECa, and 24-hour measures of phosphorus, calcium, creatinine, and calcium/creatinine ratio.

Serum markers of bone formation (BALP, P1NP, and osteocalcin) and bone resorption (CTx and NTx/creatinine) tended to increase after KRN23 dosing.

Pharmacodynamic Analyses: Briefly, the area under the curve (AUC) for the change from baseline was calculated over the 120 days of treatment or up to last measured time point before withdrawal (AUC$_{last}$) and over each of 4 dosing cycles (AUC$_1$, AUC$_2$, AUC$_3$ and AUC$_4$) for each of the following PD parameters:

Calcium homeostasis: albumin, ionized calcium, corrected calcium

PD parameters: calcitonin, intact PTH, serum creatinine, serum phosphorus, serum total calcium Vitamin D: 1,25-dihydroxy Vitamin D (1,25(OH$_2$)D), 25-hydroxy Vitamin D (25 (OH)D)

Bone biomarkers: bone alkaline phosphatase, c-telopeptide (CTX), n-telopeptide (NTX), NTX/creatinine ratio, osteocalcin, procollagen 1 (P1NP)

Sex hormones: estradiol, testosterone, free testosterone and sex hormone binding globulin (SHBG)

24-hr urine: calcium, calcium/creatinine ratio, creatinine, phosphate 2-hr urine: creatinine, random calcium, calcium/creatinine ratio, fractional excretion of calcium (FECa), phosphorous, tubular reabsorption of phosphate (TRP), Tmp/GFR calculated For PD parameters, AUC$_1$, AUC$_2$, AUC$_3$ and AUC$_4$ were estimated in Dosing Cycle 1 (Day 0 to Day 28), Dosing Cycle 2 (Day 28 to Day 56), Dosing Cycle 3 (Day 56 to Day 84), and Dosing Cycle 4 (Day 84 to Day 120), respectively. Serum PD AUC$_{last}$ was estimated from Day 0 to Day 120 or early withdrawal. If predose samples were not taken for n-th dosing interval, the last sample from previous dosing interval was used as predose sample.

Pharmacokinetic and PK-PD Relationships:

The PK exposures (Cmax, n, Cmin, n, AUC$_n$ values) increased in a dose proportional manner with similar mean tmax values across the 4 dosing intervals. The terminal t½ estimated after the fourth dosing interval was 16.4±5.8 days.

Serum KRN23 and phosphorus concentrations reached maximum levels at approximately the same time point (approximately Day 7) after each dose and their concentrations increased and decreased in parallel, supporting a direct PK-PD relationship described by an empirical Emax model. The maximum effect of KRN23 on increase in serum phosphorus levels (Emax) was 1.788 mg/dL and the KRN23 concentration reaching 50% of Emax (EC50) was 2742 ng/mL.

The AUCn or AUClast for the change from Baseline in serum phosphorus, TmP/GFR and 1,25(OH)2D increased linearly with increasing KRN23 PK exposure (AUCn or AUClast).

No meaningful effect of KRN23 treatment was observed on AUCn or AUClast for change from Baseline for the other PD parameters (serum albumin, ionized calcium, corrected calcium, calcitonin, iPTH, creatinine, total calcium, 25(OH)D, estradiol, free testosterone, total testosterone, SHBG; and 2-hour urine TRP, calcium/creatinine ratio, and FECa; and 24-hour urine calcium, calcium/creatinine ratio, creatinine, and phosphate.

The AUC for bone formation markers (BALP, P1NP, and osteocalcin) and bone resorption markers (CTx and NTx/creatinine ratio) change from Baseline versus KRN23 AUC showed positive trends of increase following KRN23 treatment.

Quality of Life: Using 2 PRO instruments (SF-36v2 and WOMAC), KRN23 treatment resulted in meaningful improvements in the health status of subjects with XLH:

All 10 SF-36v2 measures showed improvements at the end of treatment compared with Baseline with statistically significant improvements observed for 3 measures (Role Limitations due to Physical Health [RP], Bodily Pain [BP], and Physical Component Summary [PCS]; p<0.05). When corrected for multiplicity, only the RP was statistically significant (pm<0.05).

All 3 WOMAC measures showed improvements at the end of treatment compared with Baseline with statistically significant improvements observed for 2 measures (Physical Functioning and Stiffness; p<0.05).

Compared with the general US population, the study population exhibited greater deficits in baseline BP, Physical Functioning (PF), RP, and PCS scores. At the end of the study, the deficits in RP were eliminated (p<0.05) and deficits in PF, BP and PCS had lessened. All other scores showed improvements toward better health (Social Functioning [SF], Role Limitations due to Emotional Problems [RE], Vitality [VT], Mental Health [MH], Mental Component Summary [MCS], and General Health [GH]).

Compared to patients with osteoarthritis, baseline burden of disease measures for the study population were similar for 8 scales (RP, RE, BP, PF, PCS, VT, MH, and MCS) and were significantly better for GH and SF. At the end of the study, all scores improved with statistically significant (p<0.05 and pm<0.05) improvements observed for RP for the study population compared with patients with osteoarthritis.

The changes in QoL scores correlated moderately (threshold of 0.3 for the correlation) with the following clinical measures:

The change from Baseline in BP, GH and Stiffness scores correlated moderately KRN23 PK exposure (AUClast);

The change from Baseline in BP and RE scores correlated moderately with serum phosphorus and TmP/GFR change from Baseline (AUClast);

The change from Baseline in Pain scores correlated moderately with 1,25(OH)2D change from Baseline (AUClast).

Safety Results:

KRN23 was well tolerated following SC administration of 4 escalating doses in this subject population.

There were no deaths or SAEs. One subject was withdrawn from the study because of a TEAE (injection site urticaria). This event was noted on Day 57 after the third dose of KRN23, was considered of moderate intensity, and probably related to study drug. The subject was treated with prednisone and diphenhydramine.

Nearly all subjects (25 subjects, 89.3% treated with KRN23 and the 1 subject treated with placebo) had at least 1 TEAE during the study. The most common (reported for at least 5 subjects) TEAEs for subjects treated with KRN23 were nasopharyngitis (8 subjects, 28.6%, each), arthralgia (7 subjects, 25.0%), and diarrhea, back pain, and restless legs syndrome (5 subjects, 17.9%, each).

Treatment-related TEAEs were reported for 10 subjects (35.7%) treated with KRN23; no treatment-related TEAEs were reported for the 1 subject in the placebo group. Diarrhea was the only treatment-related TEAE reported for more than 1 KRN23-treated subject (2 subjects, 7.1%). All TEAEs were considered to be mild or moderate in intensity, except for 2 KRN23-treated subjects (1 with severe myalgia and 1 with severe post-traumatic pain). No life-threatening or fatal TEAEs were reported.

There was no observable pattern of laboratory abnormalities during the study. Three subjects did have laboratory abnormalities considered by the Investigator to be TEAEs (decreased neutrophil count, iron deficiency anemia, increased blood creatine phosphokinase); however, these were not considered clinically significant, did not require treatment, and did not result in discontinuation of the subjects from the study.

No changes were observed in patterns of other safety parameters obtained (vital signs, physical and neurological examination findings, cardiac CT scans, renal ultrasounds, and electrocardiograms) that were suggestive of a treatment effect.

No subject developed anti-KRN23 antibodies after dosing. No positive anti-KRN23 antibody was detected for 1 subject who experienced injection site reaction (urticaria). No other subjects experienced any hypersensitivity reactions.

There was no evidence of increased serum calcium concentrations, urinary excretion of calcium, nephrocalcinosis, or coronary artery calcium scores following KRN23 treatment.

Conclusions: Overall, the sustained effects of KRN23 on serum phosphorus, TmP/GFR, and serum 1,25(OH)$_2$D levels during a dosing interval; improvement in QoL scores after 4 doses; direct PK-PD relationship for serum KRN23 concentration and increase in serum phosphorus levels; and the favorable safety profile in adult subjects with XLH in this study suggest a potential utility of KRN23 in patients with XLH.

Analysis of Efficacy, Pharmacodynamic, and Pharmacokinetic Parameters of KRN23 in Adult Subjects with X-Linked Hypophosphatemia Primary Efficacy—Serum Phosphorus Levels The subjects have maximum serum phosphorus levels of ≤2.5 mg/dL, >2.5 to ≤3.5 mg/dL, >3.5 to ≤4.5 mg/dL, or >4.5 mg/dL. At Baseline (Day 0 of the first dosing interval), nearly all (26 subjects, 96.3%) subjects treated with KRN23 had serum phosphorous levels below 2.5 mg/dL; 1 subject had levels >2.5 to ≤3.5 mg/dL:

TABLE 4

Proportion of Subject Treated with KRN23 with Serum Phosphorus Levels by Categories (Efficacy Analysis Population)

| Visit Day/ Relative Day | Number (%) of Subject Treated with KRN23, N = 27 Categories of Serum Phosphorus Levels (mg/dL) | | | |
|---|---|---|---|---|
| | <2.5 | >2.5 to <3.5 | >3.5 to <4.5 | >4.5 |
| Dosing Interval 1 | | | | |
| Visit 2 (Day 0)/0 | 26 (96.3) | 1 (3.7) | 0 | 0 |
| Visit 4 (Day 7)/7 | 23 (85.2) | 4 (14.8) | 0 | 0 |
| Visit 7 (Day 26)/26 | 26 (96.3) | 1 (3.7) | 0 | 0 |
| Dosing Interval 2 | | | | |
| Visit 8 (Day 28)/0 | 26 (96.3) | 1 (3.7) | 0 | 0 |
| Visit 10 (Day 35)/7 | 17 (63.0) | 10 (37.0) | 0 | 0 |
| Visit 13 (Day 54)/26 | 25 (92.6) | 2 (7.4) | 0 | 0 |
| Dosing Interval 3 | | | | |
| Visit 14 (Day 56)/0 | 23 (85.2) | 2 (7.4) | 0 | 0 |
| Visit 16 (Day 63)/7 | 7 (25.9) | 20 (74.1) | 0 | 0 |
| Visit 19 (Day 82)/26 | 19 (70.4) | 8 (29.6) | 0 | 0 |
| Dosing Interval 4 | | | | |
| Visit 20 (Day 0)/0 | 18 (66.7) | 6 (22.2) | 0 | 0 |
| Visit 22 (Day 91)/7 | 3 (11.1) | 19 (70.4) | 4 (14.8) | 0 |
| Visit 25 (Day 110)/26 | 14 (51.9) | 12 (44.4) | 0 | 0 |

During the first 120 days of the study, the mean total time with serum phosphorus level >2.5 mg/dL for subjects treated with KRN23 was 27.8±17.9 days. For 1 subject treated with placebo in the bone substudy, serum phosphorus levels remained essentially unchanged from Baseline (1.6 mg/dL) to the end of the study (Visit 26) (2.0 mg/dL) with postdose levels ranging from 1.5 to 2.1 mg/dL.

During each dosing interval, the maximum serum phosphorus level was achieved on Day 7:

TABLE 5

Mean (±SD) Serum Phosphorus Levels and AUC of Serum Phosphorus Change from Baseline for Subjects Treated with KRN23 (Efficacy Analysis Set)

| | Serum Phosphorus Levels | | | $AUC_n$ or $AUC_{last}$ of Serum Phosphorus |
|---|---|---|---|---|
| Dosing Interval[a] | Day 0 (Predose) Mean (SD), mg/dL | Time to Reach Maximum Level[b] | Maximum Level Mean (SD), mg/dL | Change from Baseline Mean (SD), (mg · day/dL) |
| 1 | 1.89 (0.33), n = 27 | Day 7 | 2.21 (0.33), n = 27 | 5.68 (5.04), n = 27 |
| 2 | 1.95 (0.36), n = 27 | Day 7 | 2.47 (0.35), n = 27 | 10.72 (6.53), n = 27 |

TABLE 5-continued

| | | | | |
|---|---|---|---|---|
| 3 | 2.13 (0.27), n = 25 | Day 7 | 2.86 (0.40), n = 27 | 19.56 (9.61), n = 27 |
| 4 | 2.27 (0.32), n = 24 | Day 7 | 3.03 (0.42), n = 26 | 28.20 (12.43), n = 26 |
| Total | NA | NA | NA | 63.59 (31.58), n = 27 |

$AUC_n$ = area under the concentration-time curve for the change from Baseline in serum phosphorus concentration during the nth dosing interval (n = 1, 2, 3, or 4); $AUC_{last}$ = AUC for the change for Baseline in serum phosphorus concentration from Day 0 to Day 120 (or early withdrawal);

NA = not applicable;

SD = standard deviation.

[a]Dosing Interval 1 = Visit 2 to Visit 8; Dosing Interval 2 = Visit 8 to Visit 14; Dosing Interval 3 = Visit 14 to Visit 20; Dosing Interval 4 = Visit 20 to Visit 26; Total = Visit 2 to Visit 26.

[b]Time to reach maximum mean serum phosphorus level relative to Day 0 of each dosing interval.

The proportions of KRN23-treated subjects with serum phosphorus levels >2.5 to ≤3.5 mg/dL on Day 7 increased from 14.8% in Dosing Interval 1 to 37.0%, 74.1%, and 70.4% in Dosing Intervals 2, 3, and 4, respectively.

On Day 91 (Day 7 of the fourth dosing internal), the majority (19 subjects, 70.4%) of subjects treated with KRN23 had serum phosphorus levels >2.5 to ≤3.5 mg/dL; 3 subjects (11.1%) had levels below 2.5 mg/dL and 4 (14.8%) had levels >3.5 to ≤4.5 mg/dL. By Day 110 (Day 26 of the fourth dosing interval), 12 (44.4%) subjects had serum phosphorus levels >2.5 to ≤3.5 mg/dL and 14 (51.9%) had levels below 2.5 mg/dL. Serum phosphorus levels did not exceed 4.5 mg/dL at any time point in any subject.

In summary, the mean maximum effect of KRN23 occurred on Day 7 after fourth dosing interval. A total of 23 subjects (85.2%) had serum phosphorus levels >2.5 mg/dL and ≤4.5 mg/dL.

Pharmacodynamic Results
Serum Phosphorus

Mean serum phosphorus levels are summarized in table 6 below and displayed graphically in FIG. 1.

Mean KRN23 doses were 0.05±0.0, 0.10±0.01, 0.28±0.06, and 0.48±0.16 mg/kg for dosing intervals 1, 2, 3, and 4, respectively. During each of the 4 dosing intervals, mean serum phosphorus concentrations increased to maximum concentrations by Day 7 and then declined prior to the next dosing; both pre-dose and postdose levels increased up as the number of doses increased during the 120-day treatment period. As the doses increased from the first to the fourth dosing interval, the maximum mean serum phosphorus concentration increased from 2.21±0.33 mg/dL to 3.03±0.42 mg/dL, the mean serum phosphorus concentration prior to each dosing increased from 1.89±0.33 to 2.27±0.32 mg/dL, and mean AUCn increased from 5.68±5.04 to 28.20±12.43 mg·day/dL.

Peak and trough fluctuations of serum phosphorus were low during each dosing interval. In the fourth dosing interval, mean serum phosphorus concentrations fluctuated between a peak (3.03±0.42 mg/dL) and trough (2.27±0.32 mg/dL) with a 0.76 mg/dL difference (33%). The intersubject variability was also low for serum phosphorus concentration. At the fourth dosing interval, between-subject variation of serum phosphorus levels was only 14% for both trough and peak concentrations (=SD/mean×100%; 0.42/3.03×100%).

TABLE 6

Mean (±SD) Serum Phosphorus Levels and AUC of Serum Phosphorus Change from Baseline for Subjects Treated with KRN23 (Efficacy Analysis Set)

| | Serum Phosphorus Levels | | | $AUC_n$ or $AUC_{last}$ of Serum Phosphorus |
|---|---|---|---|---|
| Dosing Interval[a] | Day 0 (Predose) Mean (SD), mg/dL | Time to Reach Maximum Level[b] | Maximum Level Mean (SD), mg/dL | Change from Baseline Mean (SD), (mg · day/dL) |
| 1 | 1.89 (0.33), n = 27 | Day 7 | 2.21 (0.33), n = 27 | 5.68 (5.04), n = 27 |
| 2 | 1.95 (0.36), n = 27 | Day 7 | 2.47 (0.35), n = 27 | 10.72 (6.53), n = 27 |
| 3 | 2.13 (0.27), n = 25 | Day 7 | 2.86 (0.40), n = 27 | 19.56 (9.61), n = 27 |
| 4 | 2.27 (0.32), n = 24 | Day 7 | 3.03 (0.42), n = 26 | 28.20 (12.43), n = 26 |
| Total | NA | NA | NA | 63.59 (31.58), 11 = 27 |

$AUC_n$ = area under the concentration-time curve for the change from Baseline in serum phosphorus concentration during the nth dosing interval (n = 1, 2, 3, or 4);

$AUC_{last}$ = AUC for the change for Baseline in serum phosphorus concentration from Day 0 to Day 120 (or early withdrawal);

NA = not applicable;

SD = standard deviation.

[a]Dosing Interval 1 = Visit 2 to Visit 8; Dosing Interval 2 = Visit 8 to Visit 14; Dosing Interval 3 = Visit 14 to Visit 20; Dosing Interval 4 = Visit 20 to Visit 26; Total = Visit 2 to Visit 26.

[b]Time to reach maximum mean serum phosphorus level relative to Day 0 of each dosing interval.

Renal Tubular Maximum Reabsorption Rate of Phosphate to Glomerular Filtration Rate Mean TmP/GFR values for subjects treated with multiple doses of KRN23 are summarized in the table 7 below and displayed graphically in FIG. 2.

TABLE 7

Mean (±SD) TmP/GFR Levels and AUC of TmP/GFR Change from Baseline in Subjects Treated with KRN23 (Efficacy Analysis Set)

| Dosing Interval[a] | TmP/GFR Levels | | | $AUC_n$ or $AUC_{last}$ of TmP/GFR Change |
|---|---|---|---|---|
| | Day 0 (Predose)[b] Mean (SD), mg/dL | Time to Reach Maximum Level[c] | Maximum Level Mean (SD), mg/dL | from Baseline Mean (SD), (mg · day/dL) |
| 1 | 1.60 (0.36), n = 27 | Day 7 | 1.93 (0.45), n = 25 | 5.23 (6.12), n = 27 |
| 2 | 1.68 (0.35), n = 27 | Day 7 | 2.29 (0.47), n = 27 | 8.79 (6.67), n = 27 |
| 3 | 1.79 (0.35), n = 27 | Day 7 | 2.63 (0.61), n = 27 | 17.66 (9.48), n = 27 |
| 4 | 2.05 (0.34), n = 27 | Day 7 | 2.97 (0.67), n = 26 | 28.55 (13.40), n = 26 |
| Total | NA | NA | NA | 68.42 (37.96), n = 27 |

$AUC_n$ = area under the concentration-time curve for the change from Baseline in TmP/GFR during the nth dosing interval (n = 1, 2, 3, or 4);
$AUC_{last}$ = AUC for the change for Baseline in TmP/GFR from Day 0 to Day 120 (or early withdrawal);
NA = not applicable;
SD = standard deviation;
TmP/GFR = renal tubular maximum reabsorption rate of phosphate to glomerular filtration rate.
[a]Dosing Interval 1 = Visit 2 to Visit 8; Dosing Interval 2 = Visit 8 to Visit 14; Dosing Interval 3 = Visit 14 to Visit 20; Dosing Interval 4 = Visit 20 to Visit 26; Total = (Visit 2 through Visit 26.
[b]Day 26 of the previous dosing interval for Dosing Intervals 2, 3, and 4.
[c]Time to reach maximum mean TmP/GFR relative to Day 0 of each dosing interval.

During each of the 4 dosing intervals, mean TmP/GFR increased to a maximum level by Day 7 and then declined prior to the next dosing; both the pre-dose and postdose levels increased as the number of doses increased during the 120-day treatment period. As the doses increased from the first to the fourth dosing interval, the maximum mean TmP/GFR increased from 1.93±0.45 mg/dL to 2.97±0.67 mg/dL, the mean TmP/GFR prior to each dosing increased from 1.60±0.36 to 2.05±0.34 mg/dL, and mean $AUC_n$ increased from 5.23±6.12 mg·day/dL to 28.55±13.40 mg·day/dL.

Figure 3B:
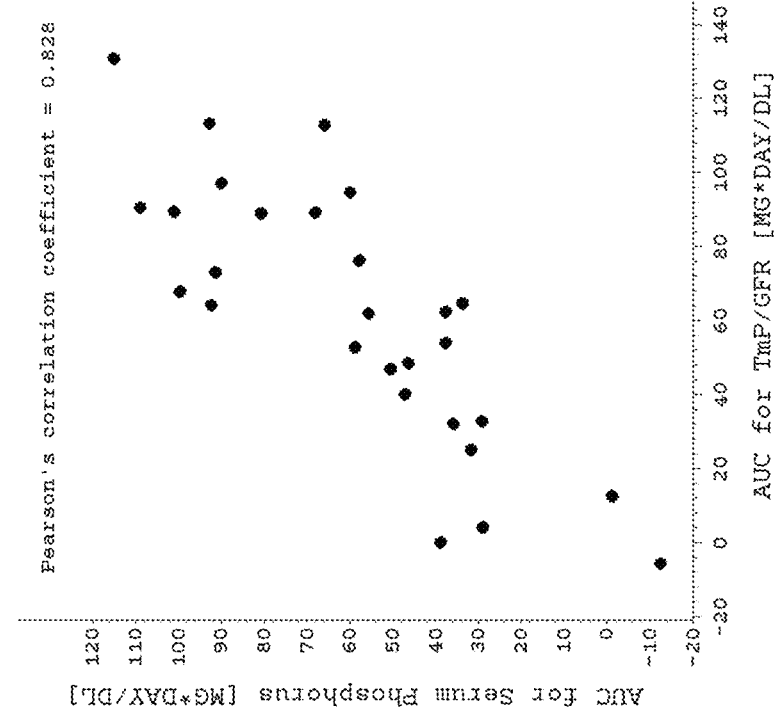

Scatter plots of $AUC_{last}$ and $AUC_n$ for serum phosphorus versus $AUC_{last}$ for TmP/GFR are presented in FIGS. 3A and 3B. Serum phosphorus and TmP/GFR were linearly correlated (Pearson correlation=0.828 and 0.900, respectively).

The $AUC_{last}$ for serum phosphorus change from Baseline (63.59±31.58 mg·day/dL) and $AUC_{last}$ for the TmP/GFR change from Baseline (68.42±37.96 mg·day/dL) were similar.

The mean calculated TmP/GFR values using a literature-reported equation versus mean TmP/GFR values manually read from the nomogram are shown in FIG. 4. The high correlation coefficient (Pearson correlation=0.9963) shows that the use of TmP/GFR calculated is comparable to TmP/GFR manually read from the nomogram. Therefore, calculated TmP/GFR values are presented in this report. For 1 subject treated with placebo in the bone substudy, TmP/GRF levels remained essentially unchanged from Baseline (1.3 mg/dL) to the end of the study (Visit 26) (1.6 mg/dL) with postdose levels ranging from 1.3 to 1.8 mg/dL.

1,25-dihydroxyvitamin D

Mean serum 1,25(OH)2D levels for subjects treated with KRN23 are displayed graphically in FIG. 5.

During each of the 4 dosing intervals, mean serum 1,25 (OH)2D levels increased to a maximum level by Day 3 or Day 7 and then returned to near the baseline level prior to the next dosing; both the pre-dose and postdose levels increased as the number of doses increased during the 120-day treatment period. As the doses increased from the first to the fourth dosing interval, the maximum mean serum 1,25(OH) 2D levels increased from 53.1±25.44 to 94.1±45.99 pg/mL, the mean serum 1,25(OH)2D levels prior to each dose increased from 36.6±14.25 to 43.8±13.72 pg/mL, and the mean $AUC_n$ increased from 144.81±209.12 to 1015.61±483.10 pg·day/mL, see Table 8:

TABLE 8

Mean (±SD) 1,25(OH)₂D Levels and AUC of 1,25(OH)₂D Change from Baseline in Subjects Treated with KRN23 (Efficacy Analysis Set)

| Dosing Interval[a] | 1,25(OH)$_2$D Levels | | | AUC$_n$ or AUC$_{last}$ |
|---|---|---|---|---|
| | Day 0 (Predose) Mean (SD), pg/mL | Time to reach Maximum Level[b] | Maximum Level Mean (SD), pg/mL | of 1,25(OH)$_2$D Change from Baseline Mean (SD), (pg · day/mL) |
| 1 | 36.6 (14.25), n = 24 | Day 3 | 53.1 (25.44), n = 27 | 144.81 (209.12), n = 24 |
| 2 | 37.1 (16.08), n = 24 | Day 3 | 73.8 (32.24), n = 27 | 448.25 (244.32), n = 24 |
| 3 | 35.6 (15.55), n = 26 | Day 7 | 91.9 (47.12), n = 27 | 843.15 (428.67), n = 24 |
| 4 | 43.8 (13.72), n = 23 | Day 3 | 94.1 (45.99), n = 26 | 1015.61 (483.10), n = 23 |
| Total | NA | NA | NA | 2441.98 (1130.66), n = 24 |

1,25(OH)$_2$D = 1,25-dihydroxyvitamin D;
AUC$_n$ = area under the concentration-time curve for the change from Baseline in serum phosphorus concentration during the nth dosing interval (n = 1, 2, 3, or 4);
AUC$_{last}$ = AUC for the change for Baseline in serum phosphorus concentration from Day 0 to Day 120 (or early withdrawal);
NA = not applicable;
SD = standard deviation.
[a]Dosing Interval 1 = Visit 2 to Visit 8; Dosing Interval 2 = Visit 8 to Visit 14; Dosing Interval 3 = Visit 14 to Visit 20; Dosing Interval 4 = Visit 20 to Visit 26; Total = Visit 2 to Visit 26.
[b]Time to reach maximum mean 1,25(OH)$_2$D level relative to Day 0 of each dosing interval.

For 1 subject treated with placebo in the bone substudy, 1,25(OH)2D levels remained essentially unchanged from Baseline (67 pg/mL) to the end of the study (Visit 26) (53.0 pg/mL) with postdose levels ranging from 46 to 70 pg/mL.

Other Pharmacodynamic Results

The mean values in serum intact FGF23 levels at baseline are summarized in table 9 below. A scatter plot of individual phosphorus concentration versus intact FGF23 levels at baseline produced and no correlation between these 2 baseline parameters was observed (data not shown).

TABLE 9

Summary of Total Intact FGF23 by Visit/Day
Efficacy Analysis Set

| | Total Intact FGF23 (pg/mL) | | | | Change (pg/mL) from Baseline | | | |
|---|---|---|---|---|---|---|---|---|
| | | Bone Substudy | | | | Bone Substudy | | |
| Visit (Day)/ Relative Day | Open Label Treatment KRN23 | KRN23 | Placebo | Total KRN23 | Open Label Treatment KRN23 | KRN23 | Placebo | Total KRN23 |
| Visit 2 (D0)/0 | | | | | | | | |
| N | 19 | 0 | 0 | 19 | | | | |
| Mean | 120.16 | | | 120.16 | | | | |
| Median | 92.40 | | | 92.40 | | | | |
| Std. Dev. | 93.921 | | | 93.921 | | | | |
| Range (Min-Max) | (35.3, 344.0) | | | (35.3, 344.0) | | | | |
| Visit 7 (D26)/26 | | | | | | | | |
| N | 26 | 1 | 0 | 27 | 19 | 0 | 0 | 19 |
| Mean | 10130.38 | 9440.00 | | 10104.81 | 9716.68 | | | 9716.68 |
| Median | 7950.00 | 9440.00 | | 8060.00 | 8041.90 | | | 8041.90 |
| Std. Dev. | 7212.678 | NA | | 7073.861 | 5518.061 | | | 5518.061 |
| Range (Min-Max) | (2380.0, 35900.0) | (9440.0, 9440.0) | | (2380.0, 35900.0) | (2287.6, 22081.0) | | | (2287.6, 22081.0) |
| Visit 13 (D54)/26 | | | | | | | | |
| N | 26 | 1 | 1 | 27 | 19 | 0 | 0 | 19 |
| Mean | 30757.31 | 23600.00 | 154.00 | 30492.22 | 28931.95 | | | 28931.95 |
| Median | 22150.00 | 23600.00 | 154.00 | 22200.00 | 21940.00 | | | 21940.00 |
| Std. Dev. | 24415.669 | NA | NA | 23981.124 | 18107.723 | | | 18107.723 |
| Range (Min-Max) | (5790.0, 121000.0) | (23600.0, 23600.0) | (154.0, 154.0) | (5790.0, 121000.0) | (5748.9, 70146.0) | | | (5748.9, 70146.0) |

TABLE 9-continued

Summary of Total Intact FGF23 by Visit/Day
Efficacy Analysis Set

| | Total Intact FGF23 (pg/mL) | | | | Change (pg/mL) from Baseline | | | |
|---|---|---|---|---|---|---|---|---|
| | | Bone Substudy | | | | Bone Substudy | | |
| Visit (Day)/ Relative Day | Open Label Treatment KRN23 | KRN23 | Placebo | Total KRN23 | Open Label Treatment KRN23 | KRN23 | Placebo | Total KRN23 |
| Visit 19 (D82)/26 | | | | | | | | |
| N | 26 | 1 | 1 | 27 | 19 | 0 | 0 | 19 |
| Mean | 70784.23 | 82100.00 | 40.00 | 71203.33 | 64200.37 | | | 64200.37 |
| Median | 63350.00 | 82100.00 | 40.00 | 68200.00 | 68131.90 | | | 68131.90 |
| Std. Dev. | 56631.443 | NA | NA | 55574.383 | 33563.920 | | | 33563.920 |
| Range (Min-Max) | (9990.0, 305000.0) | (82100.0, 82100.0) | (40.0, 40.0) | (9990.0, 305000.0) | (9930.9, 121890.0) | | | (9930.9, 121890.0) |
| Visit 25 (D110)/26 | | | | | | | | |
| N | 25 | 1 | 1 | 26 | 18 | 0 | 0 | 18 |
| Mean | 126924.00 | 10500.00 | 37.60 | 122446.15 | 124404.16 | | | 124404.16 |
| Median | 113000.00 | 10500.00 | 37.60 | 106500.00 | 116915.90 | | | 116915.90 |
| Std. Dev. | 77668.008 | NA | NA | 79450.333 | 61054.947 | | | 61054.947 |
| Range (Min-Max) | (22100.0, 391000.0) | (10500.0, 10500.0) | (37.6, 37.6) | (10500.0, 391000.0) | (22040.9, 247681.0) | | | (22040.9, 247681.0) |
| End of Study - Visit | | | | | | | | |
| N | 25 | 1 | 1 | 26 | 18 | 0 | 0 | 18 |
| Mean | 105234.40 | 78200.00 | 36.00 | 104194.62 | 112746.38 | | | 112746.38 |
| Median | 96400.00 | 78200.00 | 36.00 | 94800.00 | 106915.90 | | | 106915.90 |
| Std. Dev. | 66001.220 | NA | NA | 64884.702 | 69965.725 | | | 69965.725 |
| Range (Min-Max) | (3860.0, 259000.0) | (78200.0, 78200.0) | (36.0, 36.0) | (3860.0, 259000.0) | (3808.4, 258890.0) | | | (3808.4, 258890.0) |
| Early Withdrawal | | | | | | | | |
| N | 1 | 0 | 0 | 1 | 1 | 0 | 0 | 1 |
| Mean | 3190.00 | | | 3190.00 | 3132.20 | | | 3132.20 |
| Median | 3190.00 | | | 3190.00 | 3132.20 | | | 3132.20 |
| Std. Dev. | NA | | | NA | NA | | | NA |
| Range (Min-Max) | (3190.0, 3190.0) | | | (3190.0, 3190.0) | (3132.2, 3132.2) | | | (3132.2, 3132.2) |

Mean serum total and unbound FGF23 levels over time for subjects treated with KRN23 are summarized in Tables 10 and 11 below, respectively.

Pre-dose concentrations of total FGF23 increased with the number of KRN23 doses and reached maximum levels after the fourth dosing interval (Day 110, 26 days after the last dose). Thereafter, a decreasing trend was observed by the end of the study (Day 120, 36 days after the last dose) (FIG. 6). Total FGF23 was 120.2±93.9 pg/mL at Baseline and increased to 122446±79450 pg/mL on Day 110. Pre-dose concentration of unbound FGF23 followed a similar pattern as total FGF23 and appeared negligible compared to total FGF23 when plotted in the same scale (FIG. 6). Unbound FGF23 was 100±58 pg/mL at Baseline and increased to 7024±5035 pg/mL on Day 110. Although unbound FGF23 increased after KRN23 dosing, it was only a small fraction of the total FGF23 (5.74% on Day 110).

As expected for the 1 subject in the placebo group, unbound FGF23 stayed essentially from predose (62.7 pg/mL) to the end of the study (59.8 pg/mL) and ranged from 59.8 to 90.5 pg/mL.

A scatter plot of $AUC_{last}$ for serum phosphorus change from Baseline versus intact FGF23 at Baseline is produced and there was no correlation between the $AUC_{last}$ for serum phosphorus and baseline intact FGF23 (Pearson correlation=0.0943).

No trends were noted for mean values over time for subjects treated with KRN23 for the following PD parameters: 25(OH)D, total calcium), ionized calcium, calcitonin, and iPTH in serum, or for the other PD parameters in urine, including 2-hour urine TRP, 2-hour urine calcium/creatinine ratio, 2-hour urine FECa, 24-hour urine phosphorus, 24-hour urine calcium, 24-hour urine creatinine, 24-hour urine calcium/creatinine ratio.

Mean estradiol, testosterone, free testosterone, and SHBG over time were observed. No trends were noted for mean values over time in these parameters.

TABLE 10

Summary of Total Intact FGF23 by Visit/Day
Efficacy Analysis Set

| Visit (Day)/ Relative Day | Total Intact FGF23 (pg/mL) | | | | Change (pg/mL) from Baseline | | | |
|---|---|---|---|---|---|---|---|---|
| | | Bone Substudy | | | | Bone Substudy | | |
| | Open Label Treatment KRN23 | KRN23 | Placebo | Total KRN23 | Open Label Treatment KRN23 | KRN23 | Placebo | Total KRN23 |
| Visit 2 (D0)/0 | | | | | | | | |
| N | 19 | 0 | 0 | 19 | | | | |
| Mean | 120.16 | | | 120.16 | | | | |
| Median | 92.40 | | | 92.40 | | | | |
| Std. Dev. | 93.921 | | | 93.921 | | | | |
| Range (Min-Max) | (35.3, 344.0) | | | (35.3, 344.0) | | | | |
| Visit 7 (D26)/26 | | | | | | | | |
| N | 26 | 1 | 0 | 27 | 19 | 0 | 0 | 19 |
| Mean | 10130.38 | 9440.00 | | 10104.81 | 9716.68 | | | 9716.68 |
| Median | 7950.00 | 9440.00 | | 8060.00 | 8041.90 | | | 8041.90 |
| Std. Dev. | 7212.678 | NA | | 7073.861 | 5518.061 | | | 5518.061 |
| Range (Min-Max) | (2380.0, 35900.0) | (9440.0, 9440.0) | | (2380.0, 35900.0) | (2287.6, 22081.0) | | | (2287.6, 22081.0) |
| Visit 13 (D54)/26 | | | | | | | | |
| N | 26 | 1 | 1 | 27 | 19 | 0 | 0 | 19 |
| Mean | 30757.31 | 23600.00 | 154.00 | 30492.22 | 28931.95 | | | 28931.95 |
| Median | 22150.00 | 23600.00 | 154.00 | 22200.00 | 21940.00 | | | 21940.00 |
| Std. Dev. | 24415.669 | NA | NA | 23981.124 | 18107.723 | | | 18107.723 |
| Range (Min-Max) | (5790.0, 121000.0) | (23600.0, 23600.0) | (154.0, 154.0) | (5790.0, 121000.0) | (5748.9, 70146.0) | | | (5748.9, 70146.0) |
| Visit 19 (D82)/26 | | | | | | | | |
| N | 26 | 1 | 1 | 27 | 19 | 0 | 0 | 19 |
| Mean | 70784.23 | 82100.00 | 40.00 | 71203.33 | 64200.37 | | | 64200.37 |
| Median | 63350.00 | 82100.00 | 40.00 | 68200.00 | 68131.90 | | | 68131.90 |
| Std. Dev. | 56631.443 | NA | NA | 55574.383 | 33563.920 | | | 33563.920 |
| Range (Min-Max) | (9990.0, 305000.0) | (82100.0, 82100.0) | (40.0, 40.0) | (9990.0, 305000.0) | (9930.9, 121890.0) | | | (9930.9, 121890.0) |
| Visit 25 (D110)/26 | | | | | | | | |
| N | 25 | 1 | 1 | 26 | 18 | 0 | 0 | 18 |
| Mean | 126924.00 | 10500.00 | 37.60 | 122446.15 | 124404.16 | | | 124404.16 |
| Median | 113000.00 | 10500.00 | 37.60 | 106500.00 | 116915.90 | | | 116915.90 |
| Std. Dev. | 77668.008 | NA | NA | 79450.333 | 61054.947 | | | 61054.947 |
| Range (Min-Max) | (22100.0, 391000.0) | (10500.0, 10500.0) | (37.6, 37.6) | (10500.0, 391000.0) | (22040.9, 247681.0) | | | (22040.9, 247681.0) |
| End of Study - Visit 26 (D120) | | | | | | | | |
| N | 25 | 1 | 1 | 26 | 18 | 0 | 0 | 18 |
| Mean | 105234.40 | 78200.00 | 36.00 | 104194.62 | 112746.38 | | | 112746.38 |
| Median | 96400.00 | 78200.00 | 36.00 | 94800.00 | 106915.90 | | | 106915.90 |
| Std. Dev. | 66001.220 | NA | NA | 64884.702 | 69965.725 | | | 69965.725 |
| Range (Min-Max) | (3860.0, 259000.0) | (78200.0, 78200.0) | (36.0, 36.0) | (3860.0, 259000.0) | (3808.4, 258890.0) | | | (3808.4, 258890.0) |
| Early Withdrawal | | | | | | | | |
| N | 1 | 0 | 0 | 1 | 1 | 0 | 0 | 1 |
| Mean | 3190.00 | | | 3190.00 | 3132.20 | | | 3132.20 |
| Median | 3190.00 | | | 3190.00 | 3132.20 | | | 3132.20 |
| Std. Dev. | NA | | | NA | NA | | | NA |
| Range (Min-Max) | (3190.0, 3190.0) | | | (3190.0, 3190.0) | (3132.2, 3132.2) | | | (3132.2, 3132.2) |

TABLE 11

Summary of Unbound Intact FGF23 by Visit/Day
Efficacy Analysis Set

| | Unbound Intact FGF23 (pg/mL) | | | | Change (pg/mL) from Baseline | | | |
|---|---|---|---|---|---|---|---|---|
| | Bone Substudy | | | | Bone Substudy | | | |
| Visit/Day | Open Label Treatment KRN23 | KRN23 | Placebo | Total KRN23 | Open Label Treatment KRN23 | KRN23 | Placebo | Total KRN23 |
| Visit 2 (D0)/0 | | | | | | | | |
| N | 25 | 1 | 1 | 26 | | | | |
| Mean | 102.3 | 53.6 | 62.7 | 100.4 | | | | |
| Median | 82.1 | 53.6 | 62.7 | 81.9 | | | | |
| Std. Dev. | 58.06 | NA | NA | 57.68 | | | | |
| Range (Min-Max) | (46, 268) | (54, 54) | (63, 63) | (46, 268) | | | | |
| Visit 7 (D26)/26 | | | | | | | | |
| N | 26 | 1 | 1 | 27 | 25 | 1 | 1 | 26 |
| Mean | 589.1 | 935.0 | 77.8 | 601.9 | 359.2 | 881.4 | 15.1 | 379.3 |
| Median | 463.5 | 935.0 | 77.8 | 467.0 | 391.5 | 881.4 | 15.1 | 392.3 |
| Std. Dev. | 676.23 | NA | NA | 666.43 | 160.99 | NA | NA | 188.07 |
| Range (Min-Max) | (134, 3780) | (935, 935) | (78, 78) | (134, 3780) | (62, 724) | (881, 881) | (15, 15) | (62, 881) |
| Visit 13 (D54)/26 | | | | | | | | |
| N | 26 | 1 | 1 | 27 | 25 | 1 | 1 | 26 |
| Mean | 1347.5 | 11500.0 | 75.2 | 1723.5 | 1050.3 | 11446.4 | 12.5 | 1450.2 |
| Median | 1075.0 | 11500.0 | 75.2 | 1110.0 | 966.6 | 11446.4 | 12.5 | 1005.8 |
| Std. Dev. | 1171.18 | NA | NA | 2266.37 | 608.35 | NA | NA | 2124.18 |
| Range (Min-Max) | (345, 6220) | (11500, 11500) | (75, 75) | (345, 11500) | (284, 2624) | (11446, 11446) | (13, 13) | (284, 11446) |
| Visit 19 (D82)/26 | | | | | | | | |
| N | 26 | 1 | 1 | 27 | 25 | 1 | 1 | 26 |
| Mean | 4083.3 | 36200.0 | 72.6 | 5272.8 | 3136.4 | 36146.4 | 9.9 | 4406.0 |
| Median | 3235.0 | 36200.0 | 72.6 | 3290.0 | 3114.9 | 36146.4 | 9.9 | 3172.1 |
| Std. Dev. | 4577.20 | NA | NA | 7638.58 | 1554.23 | NA | NA | 6650.49 |
| Range (Min-Max) | (456, 25200) | (36200, 36200) | (73, 73) | (456, 36200) | (364, 6574) | (36146, 36146) | (10, 10) | (364, 36146) |
| Visit 25 (D110)/26 | | | | | | | | |
| N | 25 | 1 | 1 | 26 | 24 | 1 | 1 | 25 |
| Mean | 6812.8 | 12300.0 | 90.5 | 7023.8 | 5910.2 | 12246.4 | 27.8 | 6163.7 |
| Median | 5860.0 | 12300.0 | 90.5 | 5920.0 | 5518.4 | 12246.4 | 27.8 | 5786.6 |
| Std. Dev. | 5020.43 | NA | NA | 5035.33 | 3080.70 | NA | NA | 3271.26 |
| Range (Min-Max) | (1460, 26000) | (12300, 12300) | (91, 91) | (1460, 26000) | (1368, 12767) | (12246, 12246) | (28, 28) | (1368, 12767) |
| End of Study - Visit 26 (D120) | | | | | | | | |
| N | 25 | 1 | 1 | 26 | 24 | 1 | 1 | 2 |
| Mean | 5834.4 | 3470.0 | 59.8 | 5743.5 | 5361.9 | 3416.4 | -2.9 | 5284.1 |
| Median | 6160.0 | 3470.0 | 59.8 | 5790.0 | 5713.0 | 3416.4 | -2.9 | 5339.4 |
| Std. Dev. | 4043.21 | NA | NA | 3988.56 | 3637.57 | NA | NA | 3582.18 |
| Range (Min-Max) | (252, 16000) | (3470, 3470) | (60, 60) | (252, 16000) | (184, 15744) | (3416, 3416) | (-3, -3) | (184, 15744) |
| Early Withdrawal | | | | | | | | |
| N | 1 | 0 | 0 | 1 | 1 | 0 | 0 | 1 |
| Mean | 213.0 | | | 213.0 | 130.9 | | | 130.9 |
| Median | 213.0 | | | 213.0 | 130.9 | | | 130.9 |
| Std. Dev. | NA | | | NA | NA | | | NA |
| Range (Min-Max) | (213, 213) | | | (213, 213) | (131, 131) | | | (131, 131) |

Bone Formation Parameters

Mean serum BALP, P1NP, and osteocalcin values over time were also observed. Mean P1NP levels increased from 64.1±30.7 ng/mL on Day 0 to 123.0±75.1 ng/mL at the end of the study (Day 120). Numerical increases were also noted in serum osteocalcin (from 29.3±17.7 ng/mL on Day 0 to 42.3±25.7 ng/mL the end of the study, Day 120) and BALP (from 28.3±12.8 mcg/L on Day 0 to 38.1±23.3 mcg/L at the end of the study, Day 120).

For 1 subject treated with placebo in the bone substudy, mean values for serum BALP and P1NP remained essentially unchanged over time (BALP was 20.7 mcg/L on Day 0 and 20.6 mcg/L at the end of the study, Day 120; and osteocalcin was 17.1 ng/mL on Day 0 and 19.4 ng/mL at the end of the study, Day 120). Numerical decreases were noted in mean serum P1NP levels (from 91.0 ng/mL on Day 0 to 60.0 ng/mL at the end of the study, Day 120).

Bone Resorption Parameters

Mean serum CTx and NTx/creatinine ratio values over time were observed. Numerical increases were noted in serum CTx (from 752.0±389.5 pg/mL on Day 0 to 947.3±504.7 pg/mL at the end of the study, Day 120) and NTx/creatinine ratio (from 41.8±20.3 nmoL·BCE/mmoL on Day 0 to 56.9±34.0 nmoL·BCE/mmoL at the end of the study, Day 120).

For 1 subject treated with placebo in the bone substudy, CTx remained essentially unchanged over time (613.0 pg/mL on Day 0 and 570.0 pg/mL at the end of the study, Day 120). Numerical increases were noted in NTx/creatinine ratio (from 25.0 nmoL·BCE/mmoL on Day 0 to 40.0 nmoL·BCE/mmoL at the end of the study, Day 120).

Pharmacokinetic Results
Non-Compartmental Analysis

A summary of the total doses administered at each dosing interval is provided in Table 12 below.

TABLE 12

Study Drug Administration Total Dose (mg/kg) by Dosing Interval (Safety Analysis Set)

| | Open-Label | Bone Substudy | | Total |
|---|---|---|---|---|
| | KRN23 | KRN23 | Placebo | KRN23 |
| Dose 1 | | | | |
| N | 27 | 1 | 1 | 28 |
| Mean (SD) | 0.050 (0) | 0.050 (NA) | 0 | 0.050 (0) |
| Median | 0.050 | 0.050 (NA) | 0 | 0.050 |
| Range | (0.05, 0.05) | (0.05, 0.05) | (0, 0) | (0.05, 0.05) |
| Dose 2 | | | | |
| N | 26 | 1 | 1 | 27 |
| Mean (SD) | 0.10 (0.01) | 0.10 (NA) | 0 | 0.10 (0.01) |
| Median | 0.10 | 0.10 | 0 | 0.10 |
| Range | (0.05, 0.10) | (0.10, 0.10) | (0,0) | (0.05, 0.10) |
| Dose 3 | | | | |
| N | 26 | 1 | 1 | 27 |
| Mean (SD) | 0.28 (0.06) | 0.30 (NA) | 0 | 0.28 (0.06) |
| Median | 0.30 | 0.30 | 0 | 0.30 |
| Range | (0.05, 0.30) | (0.30, 0.30) | (0, 0) | (0.05, 030) |
| Dose 4 | | | | |
| N | 25 | 1 | 1 | 26 |
| Mean (SD) | 0.48 (0.16) | 0.30 (NA) | 0 | 0.48 (0.16) |
| Median | 0.60 | 0.30 | 0 | 0.60 |
| Range | (0.10, 0.60) | (0.30, 0.30) | (0,0) | (0.10, 0.60) |

SD = standard deviation.

Figure 7A:
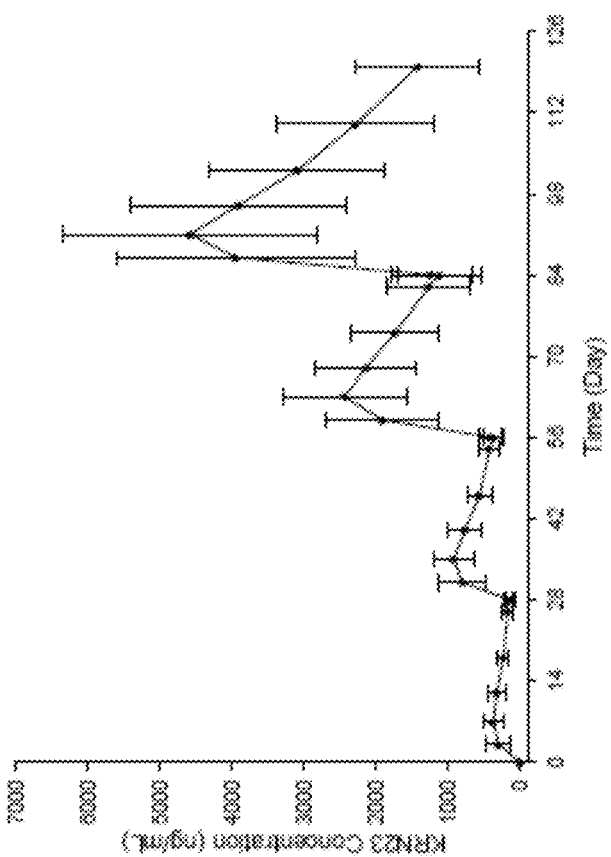
FIGS. 7A and 7B depict the mean (±SD) KRN23 concentration over time (during the 4 dosing Intervals) for the pharmacokinetic analysis during the first Phase I/II clinical trial.
Figure 7B:
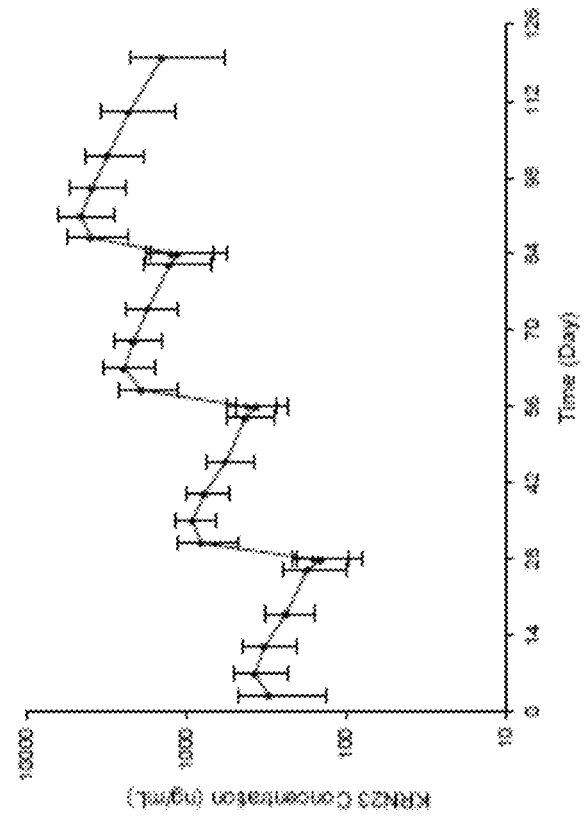

The mean serum concentrations of KRN23 are displayed graphically in FIGS. 7A and 7B. A summary of PK parameters for KRN23 are provided in Table 13 and Table 14 below.

TABLE 13

Intra-Dose-Escalation (Starting Dose 0.05 mg/kg SC) of KRN23 Every 28-days to Adult Subjects with XLH (Pharmacokinetic Analysis Set)

| Dosing Interval | Statistic | $t_{max,n}$ (day) | $C_{max,n}$ (ng/mL) | $C_{min,n}$ (ng/mL) | $AUC_n$ (ng · day/mL) |
|---|---|---|---|---|---|
| 1 | N | 27 | 27 | 27 | 27 |
| | Mean (SD) | 8.50 (2.90) | 386 (145) | 147 (53.4) | 7260 (2630) |
| | Min, Max | 2.98, 14.9 | 193, 688 | 60.7, 253 | 2980, 13200 |
| | Median | 7.94 | 374 | 139 | 6560 |
| | CV % | 34 | 38 | 36 | 36 |
| 2 | N | 27 | 27 | 27 | 27 |
| | Mean (SD) | 7.04 (1.71) | 947 (307) | 364 (130) | 17900 (5310) |
| | Min, Max | 3.95, 11.9 | 356, 1710 | 119,662 | 6500, 28600 |
| | Median | 6.96 | 870 | 373 | 16900 |
| | CV % | 24 | 32 | 36 | 30 |
| 3 | N | 27 | 27 | 27 | 27 |
| | Mean (SD) | 7.45 (3.83) | 2490 (843) | 1080 (587) | 50900 (18000) |
| | Min, Max | 1.96, 19.9 | 421, 3950 | 104, 2560 | 9500, 98000 |
| | Median | 6.95 | 2540 | 1080 | 48300 |
| | CV % | 51 | 34 | 54 | 35 |
| 4 | N | 26 | 26 | 26 | 26 |
| | Mean (SD) | 7.00 (3.22) | 4750 (1800) | 1470 (827) | 109000 (40600) |
| | Min, Max | 2.87, 15.0 | 1030, 8110 | 166, 2890 | 23800, 178000 |
| | Median | 6.89 | 5030 | 1310 | 103000 |
| | CV % | 46 | 38 | 56 | 37 |

$AUC_n$ = area under the serum concentration-time curve in n-th dosing interval;

$C_{max,n}$ = maximum serum concentration during the dosing interval;

$C_{min,n}$ = predosed observed serum concentration at the end of n-th dosing interval;

CV % = coefficient of variation, percent;

Max = maximum;

Min = minimum;

SD = standard deviation;

$t_{max,n}$ = time of maximum observed serum concentration during n-th dosing interval;

XLH = X-linked hypophosphatemia.

TABLE 14

Summary of Pharmacokinetic Parameters for KRN23 Following Intra-Dose-Escalation (Starting Dose 0.05 mg/kg) Subcutaneous Administrations of KRN23 every 28-days to Adult Subjects with XLH (Data from all 4 Dosing Intervals) (Pharmacokinetic Analysis Set)

| Statistic | $AUC_{last}$ (µg · hr/mL)$^a$ | $AUC_{inf}$ (µg · hr/mL)$^b$ | $t_{1/2}$ (day) | CL/F (mL/hr/kg)$^c$ | $V_z/F$ (mL/kg)$^d$ | $t_{last}$ |
|---|---|---|---|---|---|---|
| N | 27 | 27 | 27 | 27 | 27 | 27 |
| Mean | 4340 | 5240 | 16.4 | 0.186 | 98.3 | 122 |
| SD | 1320 | 1880 | 5.83 | 0.0780 | 34.6 | 2.79 |
| Min | 1340 | 1570 | 5.58 | 0.0835 | 51.2 | 116 |
| Median | 4520 | 5170 | 15.8 | 0.161 | 86.1 | 122 |
| Max | 6450 | 8990 | 29.5 | 0.472 | 212 | 125 |
| CV % | 30 | 36 | 35 | 42 | 35 | 2 |

$AUC_{last}$ = area under the serum concentration-time curve from time 0 to the time of last measurable concentration over all the dosing interval (Day 120 or early withdrawal) determined using the linear trapezoidal rule; $AUC_{inf}$ = area under the serum concentration-time curve from 0 to infinity over all the dosing interval determined using the linear trapezoidal rule; $t_{1/2}$ = terminal elimination half-life after 4th dosing; CL/F = apparent serum clearance; $t_{1/2}$ = terminal elimination half-life after fourth dosing interval; $V_z/F$ = apparent volume of distribution; $t_{last}$ = the time of last measurable concentration over all the dosing interval.
$^a$: $AUC_{inf}$ was calculated as $AUC_{last} + C_{last}/\lambda z_n$ where $C_{last}$ is the last measurable concentration over all the dosing interval and $\lambda z_n$ is the rate constant associated with elimination phase.
$^b$: $t_{1/2}$ was calculated as $\ln 2/\lambda z_n$.
$^c$: CL/F was calculated as Total Dose over 120 days of treatment/$AUC_{inf}$.
$^d$: $V_z/F$ was calculated as CL/F and $t_{1/2}$.

The mean tmax values were similar across the 4 dosing intervals and ranged from 7.00 to 8.50 days. The individual tmax values ranged from 1.96 to 19.9 days across all dosing intervals. The mean Cmax, n, Cmin, n, and AUCn values increased proportionally with increases in doses in Dosing Intervals 1 to 4. The inter-subject variability for AUClast was 30%. The inter-subject variability from Cmax, n and Cmin, n ranged from 32% to 38% and from 36% to 56%, respectively, across all 4 dosing intervals. The mean t½ value for KRN23 after last dose in Dosing Interval 4 was 16.4±5.8 days (individual values ranged from 5.58 to 29.5 days). The mean CL/F and Vz/F for KRN23 calculated for all 4 intervals were 0.186±0.078 mL/hr/kg and 98.3±34.6 mL/kg, respectively.

Pharmacokinetic and Pharmacodynamic Relationships

Figure 8A:
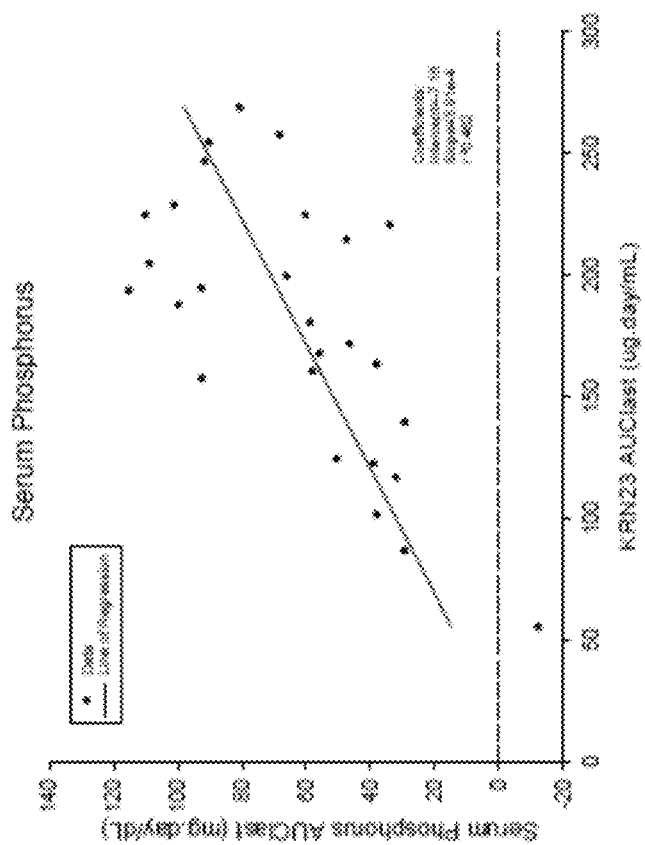
FIGS. 8A and 8B depict a scatter plot of AUC for serum phosphorus changes from baseline versus serum KRN23 AUC in the efficacy analysis during the first Phase I/II clinical trial.
Figure 8B:
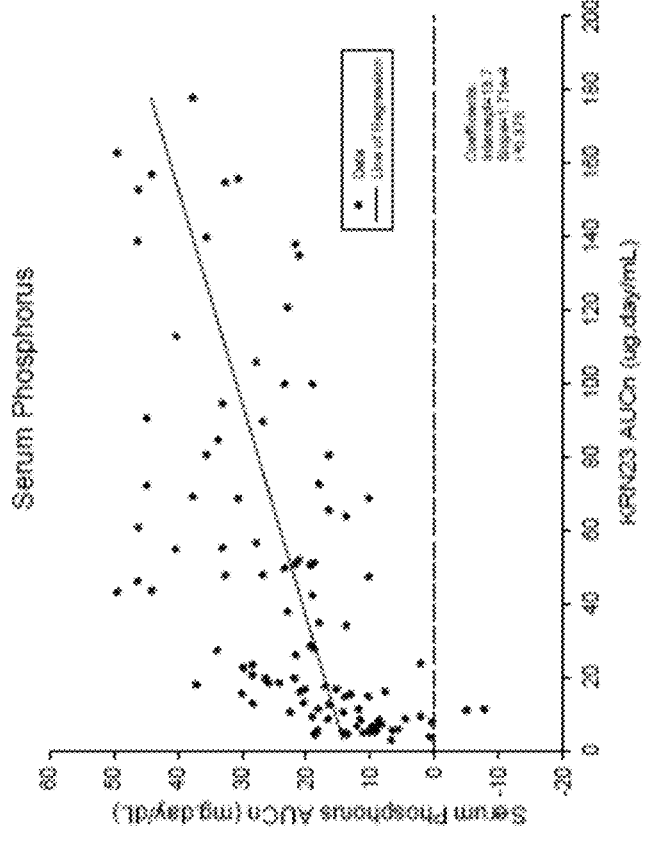

PK-PD Correlation for Serum Phosphorus: The plots of $AUC_n$ and $AUC_{last}$ of serum phosphorus change from baseline versus KRN23 $AUC_n$ and $AUC_{last}$, respectively, are shown in FIGS. 8A and 8B. The $AUC_n$ for serum phosphorus change from baseline increased linearly with increase of KRN23 AUCn (r=0.612). The AUClast for serum phosphorus change from baseline increased linearly with increase of KRN23 AUClast (r=0.680).

Figures 9A, 9B:
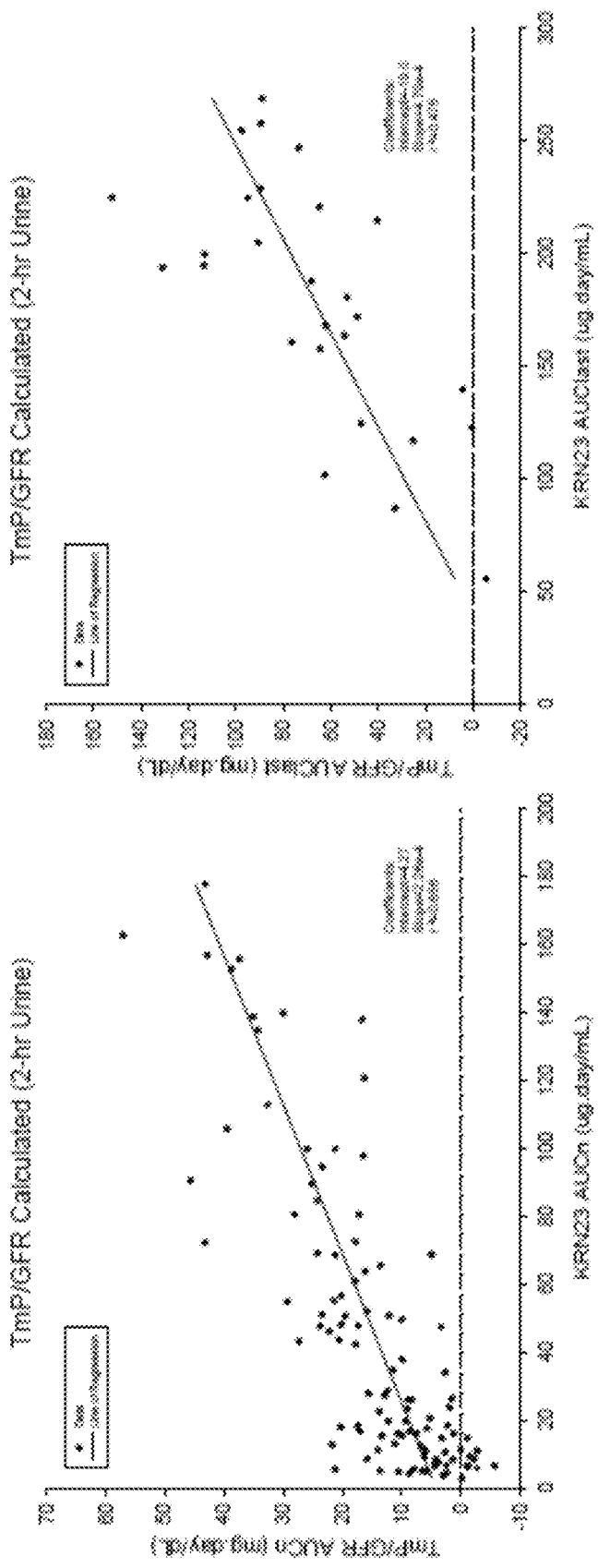
FIGS. 9A and 9B depict scatter plots of AUC for TMP/GFR change from baseline versus serum KRN23 AUC in a pharmacokinetic analysis during the first Phase I/II clinical trial.

PK-PD Correlation for TmP/GFR: The plots of AUCn and AUClast of TmP/GFR change from baseline versus KRN23 AUCn and AUClast, respectively, are shown in FIGS. 9A and 9B. The AUCn for TmP/GFR change from Baseline increased linearly with increases in KRN23 AUCn (r=0.810). The AUClast for serum phosphorus change from Baseline increased linearly with increases in KRN23 AUClast (r=0.698).

Figures 10A, 10B:
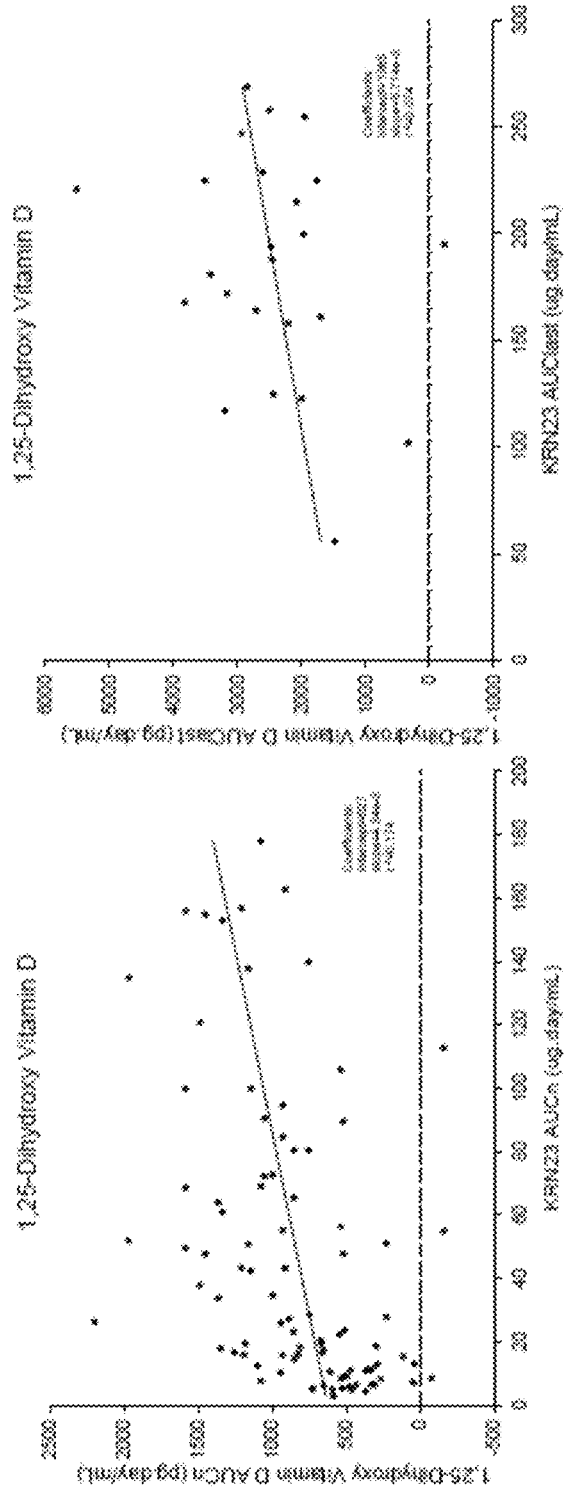
FIGS. 10A and 10B depict scatter plots of AUC for serum 1,25-Dihydroxyvitamin D change from baseline versus serum KRN23 AUC in pharmacokinetic analysis during the first Phase I/II clinical trial.

PK-PD Correlation for 1,25-dihydroxy vitamin D: The plots of AUCn and AUClast of 1,25(OH)$_2$D change from Baseline versus KRN23 AUCn and AUClast, respectively, are shown in FIGS. 10A and 10B. The AUCn for 1,25(OH)$_2$D change from baseline increased linearly with increase in KRN23 AUCn (r=0.417). The AUClast for 1,25(OH)$_2$D change from Baseline increased linearly with increases in KRN23 AUClast (r=0.272).

PK-PD Correlations for Other PD Markers: Plots of individual AUC for other PD parameters versus KRN23 AUC showed no correlation; these included serum measures of albumin, ionized calcium, corrected calcium, calcitonin, iPTH, creatinine, total calcium, 25(OH)D, NTx, estradiol, free testosterone, total testosterone, SHBG; 24-hour urine measures of calcium, calcium/creatinine ratio, creatinine, phosphate; and 2-hour urine measures of creatinine, random calcium, calcium/creatinine ratio, FECa; phosphorous, and TRP. These results suggest that multiple-dose administration of KRN23 did not affect any of these PD parameters.

PK-PD Correlations for Bone Markers: Scatter plots of AUC for bone formation markers (BALP, P1NP, and osteocalcin) and bone resorption markers (CTx and NTx/creatinine ratio) change from baseline versus KRN23 AUC showed a positive trend of increasing following KRN23 treatment. Further details are provided in the PK-PD report.

The results of the population PK-PD analysis between the change from Baseline in phosphorus concentration and KRN23 concentration are summarized in the table 15 below and in FIG. 11.

TABLE 15

Results of Population PK-PD Models for the Relationship Between Serum Phosphorus Changes From Baseline and KRN23 Concentrations in Adult Subjects with XLH Treated with KRN23 (Pharmacokinetic Analysis Set)

| Model (MOF) | Parameters | Typical Values | BSV (%) |
|---|---|---|---|
| $E_{max}$ Model | $EC_{50}$ (ng/mL) | 2742 | 61.3% |
| $(C_{KRN23} \cdot E_{max})/(EC_{50} +$ | $E_{max}$ (mg/dL) | 1.788 | 11.0% |
| $C_{KRN23})$ (MOF = 236.876) | Residual additive error (ng/mL) | 0.278 | |
| Linear Model | α | 0.138 | 106% |

TABLE 15-continued

Results of Population PK-PD Models for the Relationship Between Serum Phosphorus Changes From Baseline and KRN23 Concentrations in Adult Subjects with XLH Treated with KRN23 (Pharmacokinetic Analysis Set)

| Model (MOF) | Parameters | Typical Values | BSV (%) |
|---|---|---|---|
| $\Delta Phos = \alpha \cdot C_{KRN23} + \beta$ (MOF = 273.075) | $\beta$ Residual additive error (ng/mL) | $2.22 \times 10^{-4}$ 0.277 | 36.8% |

$\alpha$ = Slope;
$\beta$ = intercept;
BSV = between-subject variability;
$\Delta Phos$ = serum phosphorus change from Baseline;
$C_{KRN23}$ = KRN23 concentration;
$EC_{50}$ = drug concentration when 50% of $E_{max}$ is reached;
$E_{max}$ = maximum effect;
MOF = minimum value of objective function;
PK = pharmacokinetic.
PD = pharmacodynamic;

The PK-PD relationship of serum KRN23 concentration and the increase in serum phosphorus levels was described by an Emax model. The Emax model appeared to be show a better than linear model as indicated by low MOF. The maximum effect increase in serum phosphorus level was 1.788 mg/dL (Emax). KRN23 concentration reaching 50% of maximum effect (EC50) was 2742 ng/mL.

The summary of KRN23 doses in each dosing cycle and the total doses administered is provided in Table 16 below.

All 27 subjects received a starting KRN23 dose of 0.05 mg/kg during Dosing Cycle 1; 26 of the 27 subjects received 0.1 mg/kg dose in Dosing Cycle 2; and 25 of the 27 subjects received KRN23 dose of 0.3 mg/kg in Dosing Cycle 3. During the Dosing Cycle 4, 16 of the 26 subjects received 0.6 mg/kg KRN23 dose, 9 of the 26 subjects received 0.3 mg/kg dose, and 1 of 26 subjects received 0.1 mg/kg dose. The mean±SD KRN23 doses administered were: 0.05±0.00 mg/kg, 0.10±0.01 mg/kg, 0.28±0.06 mg/kg, and 0.48±0.16 mg/kg during Dosing Cycles 1, 2, 3, and 4, respectively. The mean±SD total dose over 4 Dosing Cycles was 0.89±0.22 mg/kg.

TABLE 16

Summary of Dose Data for KRN23 Following Intra-Subject Dose-Escalation of Subcutaneous Administrations of KRN23 every 28-days to Adult Subjects with X-Linked Hypophosphatemia

| Statistic | Dose 1 (mg/kg) | Dose 2 (mg/kg) | Dose 3 (mg/kg) | Dose 4 (mg/kg) | Total Dose (mg/kg) |
|---|---|---|---|---|---|
| N | 27 | 27 | 27 | 26 | 27 |
| Mean | 0.05 | 0.10 | 0.28 | 0.48 | 0.89 |
| SD | 0.00 | 0.01 | 0.06 | 0.16 | 0.22 |
| Min | 0.05 | 0.05 | 0.05 | 0.10 | 0.25 |
| Max | 0.05 | 0.10 | 0.30 | 0.60 | 1.05 |
| CV % | 0 | 10 | 21 | 34 | 25 |

The mean serum concentrations of KRN23 are illustrated in FIG. 7. The summary PK parameters for KRN23 are provided in Table 13 to Table 14. The summary PK parameters with unit conversion are provided in Table 17.

The mean tmax values were similar across four dosing cycles and ranged from 7.00 to 8.50 days. The individual tmax values ranged from 1.96 to 19.9 day in all dosing cycles. The mean Cmax, n, Cmin, n, and AUCn values increased proportionally with increase in doses in Dosing Cycles 1 to 4. The inter-subject variability for AUClast was 30%. The inter-subject variability from Cmax, n and Cmin,

TABLE 17

Summary of Pharmacokinetic Parameters (with Unit Conversion) for KRN23 Following Intra-Subject Dose-Escalation of Subcutaneous Administrations of KRN23 every 28-days to Adult Subjects with X-Linked Hypophosphatemia (Data from All 4 Dosing Cycles)

| Statistic | $AUC_{last}$ (µg · hr/mL) | $AUC_{inf}$ (µg · hr/mL) | $t_{1/2}$ (hr) | CL/F (mL/hr/kg) | $V_z/F$ (mL/kg) | $t_{last}$ (hr) |
|---|---|---|---|---|---|---|
| N | 27 | 27 | 27 | 27 | 27 | 27 |
| Mean | 4340 | 5240 | 394 | 0.186 | 98.3 | 2920 |
| SD | 1320 | 1880 | 140 | 0.0780 | 34.6 | 67.0 |
| Min | 1340 | 1570 | 134 | 0.0835 | 51.2 | 2780 |
| Median | 4520 | 5170 | 380 | 0.161 | 86.1 | 2930 |
| Max | 6450 | 8990 | 708 | 0.472 | 212 | 3000 |
| CV % | 30 | 36 | 35 | 42 | 35 | 2 |

Note: $AUC_{last}$ was calculated as AUC over 120 days; $AUC_{inf}$ was calculated as $AUC_{last} + C_{last}/\lambda z$; CL/F was calculated as Total Dose over 120 days/$AUC_{inf}$; $V_z/F$ was calculated from CL/F and $t_{1/2}$ n ranged from 32% to 38% and from 36% to 56%, respectively, across all 4 dosing cycles.

The mean±SD t½ value for KRN23 after last dose in Dosing Cycle 4 was 16.4±5.83 days (individual values ranged from 5.58 to 29.5 days). The mean±SD CL/F and Vz/F for KRN23 calculated for all 4 cycles were 4.48±1.87 mL/day/kg and 98.3±34.6 mL/kg, respectively.

Pharmacokinetic Conclusion:

PK Exposure to KRN23 (assessed by Cmax, n, Cmin, n, AUCn values) increased with increasing doses in a dose proportional manner.

Mean terminal half-life of KRN23 was 16.4 days (range: 5.58 to 29.5 days).

Mean tmax values were similar across four dosing cycles and ranged from 7.00 to 8.50 days (range: 1.96 to 19.9 days).

PK-PD Correlation Conclusion:

The AUCn or AUClast for the change from baseline in serum phosphorus increased linearly with increasing KRN23 PK exposure ($AUC_n$ or $AUC_{last}$).

The $AUC_n$ or $AUC_{last}$ for the change from baseline in TmP/GFR increased linearly with increasing KRN23 PK exposure ($AUC_n$ or $AUC_{last}$).

The $AUC_n$ or $AUC_{last}$ for the change from baseline in 1,25-dihydroxy Vitamin D increased linearly with increasing KRN23 PK exposure ($AUC_n$ or $AUC_{last}$).

No meaningful effect of KRN23 treatment was observed on $AUC_n$ or $AUC_{last}$ for change from baseline for most of the PD parameters (albumin, ionized calcium, corrected calcium, calcitonin, intact PTH, creatinine, total calcium, 25-Hydroxy Vitamin D, NTX, estradiol, free testosterone, total testosterone, SHBG in serum; calcium, calcium/creatinine ratio; creatinine, phosphate in 24-hr urine; creatinine, random calcium, calcium/creatinine ratio, FECa, phosphorous, TRP in 2-hr urine).

Increases in bone alkaline phosphatase, CTX, NTX/creatinine ratio, osteocalcin, P1NP were observed following KRN23 treatment but correlation with KRN23 exposure was weak.

Example 2: Second Phase I/II Clinical Study

Study Design and Methodology: This is an extended Phase I/II open-label, single-arm, repeat-dose, multicenter long-term extension study consisting of eligible XLH subjects from the first Phase I/11 clinical study descried above. The study design consists of 2 periods: On-Treatment and Follow-Up. At Baseline, subjects were evaluated for eligibility into this study. All eligible subjects enrolled into the KRN23 open-label portion of this study received a starting dose of KRN23 based on their serum phosphorus levels from the end-of-study visit (Visit 26, Day 120) of the first Phase I/II study, guided by a dose-escalation algorithm and safety evaluations. During the On-Treatment period, each subject receives open-label KRN23 administered SC once every 28 days (up to 12 doses). Subsequent intra-subject dose-escalation is based on serum phosphorus levels, guided by the dose-escalation algorithm for the study and safety evaluations. During the On-Treatment period, subjects undergo a total of 48 scheduled clinical evaluations, from Visits 1-48. At least 12 of these scheduled evaluations are required clinic visits, whereas the remaining 36 visits can be conducted at the clinic and/or by home health professionals. Upon completion of the On-Treatment period, subjects undergo an end-of-study clinic visit (Visit 49), and an additional home or clinic visit (Visit 50) during the Follow-Up period. Subjects participate for a total of approximately 13.5-months: approximately 11-months (48 weeks/336 days) during the On-Treatment period and approximately 2.5 months during the Follow-Up period. Eligible subjects from the first Phase I/II bone substudy may have participated in the extension portion of this substudy. Subjects were to continue the same regimen received in the first Phase I/II study. The bone substudy was closed in August 2013 due to poor accrual; the analyses originally proposed may not be possible. Safety evaluations for the study include treatment-emergent adverse event (TEAE) monitoring, safety laboratory parameters, immunogenicity, and physical examination findings.

Subjects who satisfactory completed both studies entry criteria were eligible. The study population included males and females at least 18 years of age with a documented clinical diagnosis of XLH and an intact fibroblast growth factor 23 (FGF23) level >30 pg/mL, ratio of renal tubular maximum reabsorption rate of phosphate to glomerular filtration rate (TmP/GFR)<2.0 mg/dL, estimated glomerular filtration rate (eGFR)≥60 mL/min (using Cockcroft-Gault formula), and corrected serum calcium level <10.8 mg/dL (if serum albumin was <4.0 g/dL).

Number of Subjects (planned and analyzed): Up to 35 subjects were planned; 23 subjects were screened for enrollment (21 in the open-label portion of the study; 2 in the bone substudy); all subjects satisfied eligibility criteria and were enrolled in the study.

Test Product, Dose and Mode of Administration, Batch Number: Open-label KRN23 and KRN23 treatment in the bone substudy: KRN23 for SC injection, administered by SC injection at 0.05, 0.10, 0.30, 0.60, or 1.0 mg/kg to the abdomen once every 28 days. (Batch Numbers: YU008B, YU008E, YU008F, YU009A, YU009B, YU011A, and YU011B). Subjects may be de-escalated to 0.03 mg/kg if necessary.

Comparative Agent, Dose, and Mode of Administration, Batch Number: Bone substudy: KRN23 Placebo for SC injection, administered by SC injection to the abdomen once every 28 days. (Batch number: PYU090908C and PYU120413A).

Duration of Treatment: The duration of treatment in this study was up to approximately 11 months (48 weeks/336 days) during the On-Treatment period and 2.5 months in the Follow-Up period, for a total of approximately 13.5 months.

Endpoints:

Primary: The primary endpoints were designed to evaluate the safety and efficacy of repeat-doses of KRN23 SC administration via the assessment of the:

Number and % of adverse events (AEs) by severity and relationship to investigational product Number of clinically significant changes in vital signs, laboratory tests, physical examinations, electrocardiogram (ECG), renal ultrasound and cardiac computed tomography (CT)/Coronary Calcium Scoring (CCS) and Aortic Calcium Scoring (ACS)

Number and % of subjects with post-dose serum phosphorus levels: ≤2.5 mg/dL; >2.5 mg/dL but ≤3.5 mg/dL; >3.5 mg/dL but ≤4.5 mg/dL and >4.5 mg/dL Number of subjects who develop anti-KRN23 antibodies Secondary: The secondary endpoints were designed to evaluate the following parameters by treatment group; changes are calculated from Baseline (Visit 2, Day 0 of first Phase I/II clinical trial):

Change in serum phosphorus levels

Changes in calcium homeostasis: 1,25(OH)2D (1,25-dihydroxy vitamin D), 25(OH)D (25-hydroxy vitamin D), total calcium, ionized calcium, calcitonin, and iPTH (intact parathyroid hormone)

Changes in the ratio TmP/GFR, tubular reabsorption of phosphate (TRP), urine calcium/creatinine ratio, and fractional excretion of calcium (FECa), as measured from 2-hour urine Changes in urinary phosphate, calcium, creatinine, and urine calcium/creatinine ratio, as measured from 24-hour urine Changes in bone biomarkers: serum BALP (bone alkaline phosphatase), P1NP (procollagen type 1 N-propeptide), CTx (carboxy-terminal cross-linked telopeptide of type I collagen), and osteocalcin, and urinary NTx (amino terminal cross-linked telopeptide of type I collagen)

Changes in sex hormones: estradiol, testosterone, free testosterone, and sex hormone binding globulin (SHBG)

Characterize the population PK of KRN23 from cumulative dosing across both the first and second Phase I/II clinical trial studies Changes in the QoL assessments in SF-36v2 (Outcomes Study 36-item Short Form, Volume 2) and WOMAC (Western Ontario and McMaster Osteoarthritis Index)

Summary of Results: This clinical study summary is based on preliminary data available as of the 12 Aug. 2013 data cut-off date.

Exposure: A total of 22 subjects were treated with KRN23 (21 in the open-label portion of the study and 1 in the bone substudy) and 1 subject was treated with Placebo in the bone substudy. In the initial dosing interval (Dose Interval 1), the mean KRN23 dose was 0.541±0.2039 mg/kg. In subsequent dosing intervals, mean KRN23 dose was increased and varied in a narrow range (0.733±0.2817 mg/kg to 0.865±0.2618 mg/kg). Most subjects treated with KRN23 (19/22, 86.4%) had received all 12 planned doses as of the data cut-off date; the 1 Placebo-treated subject had received 3 doses of Placebo as of the data cut-off date.

Study Population: Among the 22 subjects treated with KRN23, the median age was 42.5 years (range: 20 to 67 years), the majority (13/22, 59.1%) were women, and nearly all (21/22, 95.5%) were white/Caucasian while 1 (4.5%) was Black/African American/African Caribbean. The median height was 148.79 cm (range: 121.9 to 170.2 cm) and median weight was 75.30 kg (range: 51.3 to 124.3 kg).

Serum phosphorus and TmP/GFR levels at Baseline were below the lower limit of the normal reference range for all subjects. At Baseline, the overall mean 1,25(OH)2D level was within the normal reference range. Baseline unbound intact FGF23 levels ranged from 54 to 268 pg/mL for KRN23-treated subjects.

Efficacy Results:

At the pre-treatment baseline, all subjects had serum phosphorus levels <2.5 mg/dL. Following KRN23 administration, the time of maximum PD effect (peak) was observed on Days 7 and 14. After the first dose of KRN23, 77.1% (Day 7) and 81.8% (Day 14) of subjects had increased serum phosphorus levels within the target range of >2.5 to ≤3.5 mg/dL. This peak effect was relatively consistent throughout the study ranging from 45.5% to 81.8%. The percentage of subjects within the target range was generally similar on Day 7 and 14. No serum phosphorus level >4.5 mg/dL was reported for any subject at any time point in the study.

Pharmacodynamic Results:

During each of the 12 dosing intervals, mean serum phosphorus concentrations for KRN23-treated subjects increased substantially by Day 7 or 14 and then declined but remained above baseline at the end of the dose interval. All subjects experienced an increase from baseline at all visits. The mean serum phosphorus concentration increased from 1.85±0.282 mg/dL at the pre-treatment baseline to a maximum level of 2.87±0.392 mg/dL on Day 14 of Dose Interval 1, and the maximum level remained within the range of 2.71±0.428 mg/dL to 2.96±0.468 mg/dL throughout the study. At day 25 post-dose, 33%-57% of subjects were still within the target range (>2.5 to ≤3.5 mg/dL) and at the end of the dose interval 23.8%-38.1% of subjects remained within the target range (>2.5 to ≤3.5 mg/dL).

TmP/GFR is the proposed mechanism by which KRN23-mediated inhibition of excess FGF23 increases phosphorus levels. TmP/GFR results followed the same pattern as that observed for serum phosphorus. The mean TmP/GFR was increased from a pre-treatment baseline level of 1.564±0.3012 into a maximum range from 2.408±0.7205 mg/dL to 2.921±0.5990 mg/dL on Day 14 of each dosing interval. This magnitude of increase in TmP/GFR was clinically meaningful and correlates closely with the increases in serum phosphorus.

During each of the 12 dosing intervals, mean serum 1,25(OH)2D levels increased to a maximum level by Day 7 and then declined to a level comparable to Baseline prior to the next dosing.

No trends were noted in mean values over time for other serum and urine PD parameters after KRN23 dosing compared to Baseline. Serum parameters included 25(OH)D, total calcium, ionized calcium, calcitonin and iPTH. Urine markers included 2-hour measures of TRP, calcium/creatinine ratio, and FECa, and 24-hour measures of phosphorus, calcium, creatinine, and calcium/creatinine ratio.

Biomarkers of bone formation and resorption may provide an indication of treatment effect. P1NP increased from 69.6±29.86 ng/mL at baseline of the first Phase I/II clinical trial study to a maximum of 170.4±100.79 ng/mL, which represents a percent change increase of 148.1%. Increases were observed at all post-baseline measurements. Mean serum osteocalcin and BALP also increased but to a lesser extent throughout the study. Increases from baseline in bone resorption parameters (Ctx and NTx) were also observed.

PK and PK-PD Relationships: Population PK analyses will be included in the final study report. Any PK-PD relationship analyses will be included in the final study report.

Quality of Life: Analyses of data from QoL assessments of the subjects during the second Phase I/II clinical trial study were not available as of the date of this report and will be included in the final study report.

Safety Results:

KRN23 was well tolerated following SC administration of up to 12 doses in this subject population.

There were no deaths or life-threatening TEAEs reported in the study. SAEs were reported for 3 subjects treated with KRN23 (cervical spinal stenosis, breast cancer, and hypertensive crisis; each 1 subject). Two subjects treated with KRN23 were discontinued from the study due to TEAEs possibly related to KRN23: severe or debilitating restless legs syndrome (RLS) that was considered a DLT in 1 subject, and moderate nephrolithiasis not considered a DLT but still leading to discontinuation of the other subject.

TEAEs were reported for most of the subjects (20 subjects, 90.9%) treated with KRN23 and the 1 subject treated with Placebo during the study. In the KRN23-treated group, the most common TEAEs (reported for at least 3 subjects) were injection site reaction, sinusitis, and arthralgia (each 5 subjects, 22.7%); abdominal discomfort, back pain, pain in extremity and dizziness (each 4 subjects, 18.2%); and vertigo, fatigue, gastroenteritis viral, nasopharyngitis, headache, and RLS (each 3 subjects, 13.6%).

Treatment-related TEAEs were reported for 14 subjects (63.6%) treated with KRN23. Injection site reaction (5 subjects, 22.7%); arthralgia and RLS (each 3 subjects, 13.6%); and injection site pain (2 subjects, 9.1%) were the only TEAEs classified as treatment-related reported for more than 1 KRN23-treated subject. Severe or disabling TEAEs were reported for 5 subjects (22.7%) treated with KRN23: breast cancer unlikely study drug-related, RLS possibly study drug-related, myalgia and hypertensive crisis not study drug-related, cervical spinal stenosis not study drug-related, and post-traumatic pain and pain in extremity not study drug-related.

There was no discernible pattern of clinically significant laboratory abnormalities during the study. Four subjects had laboratory abnormalities considered by the Investigator to be TEAEs: moderate neutrophil count decreased and white blood cell count decreased possibly related to study drug; mild blood pressure decreased possibly related to study drug; mild blood triglycerides increased not related to study drug; and mild alanine aminotransferase increased and aspartate aminotransferase increased unlikely related to study drug and mild blood creatine phosphokinase increased possibly related to study drug. These events were not considered serious or clinically significant, did not require treatment, and did not result in discontinuation of the subjects from the study.

No adverse cardiac effects of relevance were noted in cardiac CT scans or ECGs. A separate independent cardiologist evaluation of the ECGs showed no evidence or changes of LVH by ESTES criteria when comparing pretreatment ECGs (in the first or the second Phase I/II clinical trial study) to post-treatment ECGs in the second Phase I/II clinical trial study.

No adverse renal effects were noted on renal ultrasound, and no treatment-related changes in iPTH, serum and 24-hour urinary calcium were noted. No clinical significant ectopic mineralization changes were observed.

No changes were observed in patterns of other safety parameters (vital signs, physical and neurological examination findings) that were suggestive of a treatment-related adverse effect.

No subject developed anti-KRN23 antibodies after dosing or developed hypersensitivity reactions.

There was no evidence of increased calcifications in any extra-osseous tissue studied, including kidney.

Conclusions:

Data from this study to date are consistent with the model that KRN23 blocks FGF23 action after SC administration, which leads to a sustained increase in serum phosphorus levels due to increased tubular reabsorption of phosphate (TmP/GFR). Increased 1,25(OH)$_2$D was also observed, as expected, based on the inhibition of the excess of FGF23. Increases in bone formation and resorption markers were also observed. Taken together, changes in these biomarkers support the hypothesis that KRN23 may provide clinical improvements in bone quality, reverse the changes associated with rickets, and eventually improve physical outcomes such as the bowing of the legs, pain, and short stature characteristic of patients with XLH.

Available data from this study demonstrated that KRN23 administered SC every 28 days, in most cases at 0.6 or 1.0 mg/kg, improves peak serum phosphorus levels to the 2.5-3.5 mg/dL range from a mean pre-treatment baseline level of 1.85 mg/dL. This improvement persists over a period of 48 weeks (336 days) and 12 KRN23 doses.

The data have also demonstrated that KRN23 treatment improves TmP/GFR; the effect persists for nearly 28 days following each treatment and is maintained for 48 weeks and 12 doses. This result is consistent with the concept that KRN23 reverses the decrease in the sodium-phosphate co-transporter in the kidney, resulting in substantial increases in the efficiency of phosphate reabsorption in the renal tubules. The magnitude of increase in TmP/GFR was clinically meaningful and correlates with serum phosphorus, indicating the likely mechanism by which KRN23-mediated inhibition of excess FGF23 achieves the desired effect.

Data from this study have also shown that KRN23 treatment increases serum 1,25(OH)$_2$D levels. This is consistent with the concept that KRN23 reverses the decreased expression of the 1-alpha hydroxylase required to convert serum 25 hydroxy Vitamin D, into the 1,25 dihydroxy form that actively stimulates phosphate absorption in the intestine. Improvements in biomarkers of bone formation and resorption suggest an increase in bone remodeling. These improvements plus the increase in serum phosphorus is expected to be the mechanism by which bone quality will improve in patients with XLH.

KRN23 was well tolerated by adult XLH subjects over a period of 48 weeks with up to 12 doses of drug administered SC at up to 1.0 mg/kg. No deaths or life threatening TEAEs occurred. Treatment-related TEAEs included injection site reaction; arthralgia and RLS; and injection site pain. SAEs (assessed as unlikely to be or not study drug related) were reported for 3 subjects. No discernible clinically significant trends of lab abnormalities suggestive of a treatment-related adverse effect were noted.

Calcifications of the kidney were a frequent finding in subjects at Baseline before KRN23 treatment, likely due to prior phosphate therapy. Clinical data on KRN23 to date, including that in this study using renal ultrasound and ultra-fast CT scans of the heart, have not identified significant, novel appearance or any increase in calcifications in these 2 most susceptible organs. In addition, no increases in serum or urinary calcium or PTH were observed, and the phosphorus levels never exceeded the upper limit of normal, therefore the major biochemical parameters usually associated with ectopic mineralization did not occur with KRN23 administration over this long-term observational study.

In conclusion, KRN23 treatment was well tolerated and increased serum phosphorus, TmP/GFR, and serum 1,25 (OH)$_2$D levels in each dosing interval throughout the 48 weeks of treatment. No off target effects were observed. These clinically meaningful increases in pharmacodynamic and biochemical markers, and the favorable safety profile in adult subjects with XLH, suggest a potential utility of KRN23 treatment for patients with XLH.

Efficacy Evaluation

Disease Characteristics at Baseline

Baseline disease characteristics, including the levels of serum phosphorus, TmP/GFR, 1,25(OH)$_2$D, and unbound intact FGF23 for subjects in the Efficacy Analysis Set, are presented in Table 18 below. Serum phosphorus and TmP/GFR levels at Baseline were below the lower limit of the normal reference range for all subjects. At Baseline, the overall mean 1,25(OH)$_2$D level was within the normal reference range (Kratz 2012). Baseline unbound intact FGF23 levels ranged from 54 to 268 pg/mL for KRN23-treated subjects.

Primary Efficacy—Serum Phosphorus Levels

At the pre-treatment baseline (Visit 2, Day 0 of the first Phase I/II clinical trial study), all 22 subjects treated with KRN23 (100%) and the 1 subject treated with Placebo had serum phosphorus levels <2.5 mg/dL. During each 28 day

TABLE 18

Table Baseline Disease Characteristics (Efficacy Analysis Set)

| | Open-label | Bone Substudy | | Total |
|---|---|---|---|---|
| | KRN23<br>N = 21 | KRN23<br>N = 1 | Placebo<br>N = 1 | KRN23<br>N = 22 |
| Unbound intact FGF23 (pg/mL) | | | | |
| n | 20 | 1 | 1 | 21 |
| Mean (SD) | 106.0 (63.32) | 53.6 (NA) | 62.7 (NA) | 103.5 (62.77) |
| Min, Max | (56, 268) | (54, 54) | (63, 63) | (54, 268) |
| Serum phosphorus (mg/dL)[b] | | | | |
| n | 21 | 1 | 1 | 22 |
| Mean (SD) | 1.85 (0.287) | 2.00 (NA) | 1.60 (NA) | 1.85 (0.282) |
| Min, Max | (1.2, 2.3) | (2.0, 2.0) | (1.6, 1.6) | (1.2, 2.3) |
| TmP/GFR (mg/dL)[b] | | | | |
| n | 21 | 1 | 1 | 22 |
| Mean (SD) | 1.570 (0.3076) | 1.450 (NA) | 1.250 (NA) | 1.564 (0.3012) |
| Min, Max | (0.85, 2.03) | (1.45, 1.45) | (1.25, 1.25) | (0.85, 2.03) |
| Serum 1,25 (OH)$_2$D (pg/mL) | | | | |
| n | 18 | 1 | 1 | 19 |
| Mean (SD) | 36.1 (12.93) | 42.0 (NA) | 67.0 (NA) | 36.4 (12.64) |
| Min, Max | (10, 61) | (42, 42) | (67, 67) | (10, 61) |
| Serum total calcium (mg/dL) | | | | |
| n | 21 | 1 | 1 | 22 |
| Mean (SD) | 9.11 (0.407) | 9.30 (NA) | 9.30 (NA) | 9.12 (0.399) |
| Min, Max | (8.5, 10.2) | (9.3, 9.3) | (9.3, 9.3) | (8.5, 10.2) |
| Serum iPTH (pg/mL) | | | | |
| n | 21 | 1 | 1 | 22 |
| Mean (SD) | 84.2 (35.07) | 74.0 (NA) | 77.0 (NA) | 83.7 (34.29) |
| Min, Max | (40, 143) | (74, 74) | (77, 77) | (40, 143) |
| BALP (µg/L) | | | | |
| n | 21 | 1 | 1 | 22 |
| Mean (SD) | 30.94 (12.583) | 34.40 (NA) | 20.70 (NA) | 31.10 (12.302) |
| Min, Max | (13.2, 52.4) | (34.4, 34.4) | (20.7, 20.7) | (13.2, 52.4) |
| 24-hr urine calcium (mg/24 hr) | | | | |
| n | 21 | 1 | 1 | 22 |
| Mean (SD) | 100.5 (69.27) | 30.0 (NA) | 54.0 (NA) | 97.3 (69.25) |
| Min, Max | (11, 253) | (30, 30) | (54, 54) | (11, 253) |
| 24-hr urine creatinine (g/24 hr) | | | | |
| n | 21 | 1 | 1 | 22 |
| Mean (SD) | 1.383 (0.6689) | 1.230 (NA) | 1.040 (NA) | 1.376 (0.6536) |
| Min, Max | (0.54, 3.01) | (1.23, 1.23) | (1.04, 1.04) | (0.54, 3.01) |
| 2-hr calcium/creatinine ratio, (mg/g creatinine) | | | | |
| n | 21 | 1 | 1 | 22 |
| Mean (SD) | 53.1 (39.83) | 7.0 (NA) | 36.0 (NA) | 51.0 (40.09) |
| Min, Max | (11, 192) | (7,7) | (36,36) | (7, 192) |

1,25(OH)$_2$D = 1,25-dihydroxy vitamin D;
BALP = bone alkaline phosphatase;
FGF23 = fibroblast growth factor 23;
hr = hour;
iPTH = intact parathyroid hormone;
Max = maximum;
Min = minimum;
NA = not applicable;
SD = standard deviation;
TmP/GFR = ratio of renal tubular maximum reabsorption rate of phosphate to glomerular filtration rate.
a: Baseline value is from Visit 2, Day 0 of the first Phase I/II clinical trial.
b: Normal ranges: 2.5 to 4.3 mg/dL (Kratz 2012) for serum phosphorus and 2.5-4.3 mg/dL for TmP/GFR (Walton et al. 1975).

dosing interval, the maximum serum phosphorus levels (peak) were achieved on Day 7 or 14 (Table 19). On Day 7 and 14 after the first KRN23 treatment (dosing interval 1), the serum phosphorus levels of a large majority of subjects (17-18 subjects, 77.3%-81.8%) had increased from <2.5 mg/dL into the target range of >2.5 to ≤3.5 mg/dL. This peak effect was relatively consistent throughout the study ranging from 45.5% to 81.8%. The percentage of subjects within the target range was generally similar on both Day 7 and 14 throughout the study period. Peak serum phosphorus levels on Day 7 or 14 were increased into the >3.5 to ≤4.5 mg/dL range for 0 to 3 KRN23-treated subjects (0-13.6%) throughout the study, but no serum phosphorus level >4.5 mg/dL was reported for any subject at any time point.

TABLE 19

Proportion of Subject Treated with KRN23 with Serum Phosphorus Levels by Categories (Efficacy Analysis Population)

| | Number (%) of Subjects Treated with KRN23, N = 22 Serum Phosphorus Levels (mg/dL) | | | |
|---|---|---|---|---|
| | ≤2.5 | >2.5 to ≤3.5 | >3.5 to ≤4.5 | >4.5 |
| Baseline | 22 (100.0) | 0 (0.0) | 0 (0.0) | 0 (0.0) |
| Dosing Interval 1 | | | | |
| Visit 1/0 | 21 (95.5) | 0 (0.0) | 0 (0.0) | 0 (0.0) |
| Visit 2/7 | 4 (18.2) | 17 (77.3) | 1 (4.5) | 0 (0.0) |
| Visit 3/14 | 4 (18.2) | 18 (81.8) | 0 (0.0) | 0 (0.0) |
| Visit 4/25 | 15 (68.2) | 7 (31.8) | 0 (0.0) | 0 (0.0) |
| Dosing Interval 2 | | | | |
| Visit 5/0 | 15 (68.2) | 6 (27.3) | 0 (0.0) | 0 (0.0) |
| Visit 6/7 | 6 (27.3) | 13 (59.1) | 2 (9.1) | 0 (0.0) |
| Visit 7/14 | 4 (18.2) | 15 (68.2) | 2 (9.1) | 0 (0.0) |
| Visit 8/25 | 7 (31.8) | 13 (59.1) | 0 (0.0) | 0 (0.0) |
| Dosing Interval 3 | | | | |
| Visit 9/0 | 12 (54.5) | 9 (40.9) | 0 (0.0) | 0 (0.0) |
| Visit 10/7 | 5 (22.7) | 15 (68.2) | 1 (4.5) | 0 (0.0) |
| Visit 11/14 | 6 (27.3) | 15 (68.2) | 0 (0.0) | 0 (0.0) |
| Visit 12/25 | 10 (45.5) | 11 (50.0) | 0 (0.0) | 0 (0.0) |
| Dosing Interval 4 | | | | |
| Visit 13/0 | 13 (59.1) | 8 (36.4) | 0 (0.0) | 0 (0.0) |
| Visit 14/7 | 7 (31.8) | 11 (50.0) | 3 (13.6) | 0 (0.0) |
| Visit 15/14 | 3 (13.6) | 17 (77.3) | 1 (4.5) | 0 (0.0) |
| Visit 16/25 | 10 (45.5) | 11 (50.0) | 0 (0.0) | 0 (0.0) |
| Dosing Interval 5 | | | | |
| Visit 17/0 | 13 (59.1) | 7 (31.8) | 0 (0.0) | 0 (0.0) |
| Visit 18/7 | 5 (22.7) | 15 (68.2) | 0 (0.0) | 0 (0.0) |
| Visit 19/14 | 8 (36.4) | 13 (59.1) | 0 (0.0) | 0 (0.0) |
| Visit 20/25 | 9 (40.9) | 12 (54.5) | 0 (0.0) | 0 (0.0) |
| Dosing Interval 6 | | | | |
| Visit 21/0 | 15 (68.2) | 5 (22.7) | 0 (0.0) | 0 (0.0) |
| Visit 22/7 | 3 (13.6) | 15 (68.2) | 2 (9.1) | 0 (0.0) |
| Visit 23/14 | 3 (13.6) | 15 (68.2) | 1 (4.5) | 0 (0.0) |
| Visit 24/25 | 12 (54.5) | 8 (36.4) | 0 (0.0) | 0 (0.0) |
| Dosing Interval 7 | | | | |
| Visit 25/0 | 13 (59.1) | 7 (31.8) | 0 (0.0) | 0 (0.0) |
| Visit 26/7 | 4 (18.2) | 16 (72.7) | 0 (0.0) | 0 (0.0) |
| Visit 27/14 | 5 (22.7) | 14 (63.6) | 0 (0.0) | 0 (0.0) |
| Visit 28/25 | 10 (45.5) | 10 (45.5) | 0 (0.0) | 0 (0.0) |
| Dosing Interval 8 | | | | |
| Visit 29/0 | 13 (59.1) | 6 (27.3) | 0 (0.0) | 0 (0.0) |
| Visit 30/7 | 7 (31.8) | 8 (36.4) | 3 (13.6) | 0 (0.0) |
| Visit 31/14 | 7 (31.8) | 11 (50.0) | 0 (0.0) | 0 (0.0) |
| Visit 32/25 | 13 (59.1) | 6 (27.3) | 0 (0.0) | 0 (0.0) |
| Dosing Interval 9 | | | | |
| Visit 33/0 | 11 (50.0) | 7 (31.8) | 0 (0.0) | 0 (0.0) |
| Visit 34/7 | 5 (22.7) | 12 (54.5) | 1 (4.5) | 0 (0.0) |
| Visit 35/14 | 5 (22.7) | 12 (54.5) | 0 (0.0) | 0 (0.0) |
| Visit 36/25 | 11 (50.0) | 7 (31.8) | 1 (4.5) | 0 (0.0) |
| Dosing Interval 10 | | | | |
| Visit 37/0 | 12 (54.5) | 7 (31.8) | 0 (0.0) | 0 (0.0) |
| Visit 38/7 | 7 (31.8) | 10 (45.5) | 2 (9.1) | 0 (0.0) |
| Visit 39/14 | 8 (36.4) | 9 (40.9) | 2 (9.1) | 0 (0.0) |
| Visit 40/25 | 10 (45.5) | 9 (40.9) | 0 (0.0) | 0 (0.0) |

TABLE 19-continued

Proportion of Subject Treated with KRN23 with
Serum Phosphorus Levels by Categories (Efficacy Analysis Population)

| | Number (%) of Subjects Treated with KRN23, N = 22 Serum Phosphorus Levels (mg/dL) | | | |
|---|---|---|---|---|
| | ≤2.5 | >2.5 to ≤3.5 | >3.5 to ≤4.5 | >4.5 |
| Dosing Interval 11 | | | | |
| Visit 41/0 | 14 (63.6) | 5 (22.7) | 0 (0.0) | 0 (0.0) |
| Visit 42/7 | 5 (22.7) | 13 (59.1) | 1 (4.5) | 0 (0.0) |
| Visit 43/14 | 8 (36.4) | 10 (45.5) | 1 (4.5) | 0 (0.0) |
| Visit 44/25 | 9 (40.9) | 10 (45.5) | 0 (0.0) | 0 (0.0) |
| Dosing Interval 12 | | | | |
| Visit 45/0 | 14 (63.6) | 5 (22.7) | 0 (0.0) | 0 (0.0) |
| Visit 46/7 | 8 (36.4) | 9 (40.9) | 2 (9.1) | 0 (0.0) |
| Visit 47/14 | 9 (40.9) | 10 (45.5) | 0 (0.0) | 0 (0.0) |
| Visit 48/25 | 12 (54.5) | 7 (31.8) | 0 (0.0) | 0 (0.0) |

Note that each row of data presents available data for that visit/time point, and the total number of subjects (and associated percentages) at each visit may not add up to 22 (or 100%), where there is missing data. The percentage of subjects whose serum phosphorus remained within the target range (>2.5 to ≤3.5 mg/dL) at each time point was calculated with a denominator based on the total of 22 subjects who had received any number of KRN23 doses, whether or not serum phosphorus data were obtained for all of these subjects at that time point. As of the data cut-off date, 3 subjects had not received all of their planned KRN23 doses (1 subject received 1 dose and was discontinued; 1 subject had received 5 doses and 1 subject had received 7 doses and remained on study), and at some time points serum phosphorus data were not available for all subjects who had been treated and remained on study. Therefore, in some instances, the calculated percentage may underestimate the responder rate of subjects achieving a serum phosphorus > than 2.5 mg/dL.

For the 1 subject treated with Placebo in the bone substudy, serum phosphorus levels remained essentially unchanged from Baseline (1.60 mg/dL), with post-dose levels ranging from 1.70 to 2.00 mg/dL.

In summary, KRN23 increased serum phosphorus levels from baseline in all subjects at almost all data points either at the peak or through, and most treated subjects achieved the target therapy goal (>2.5 to ≤3.5 mg/dL). This effect was maintained for up to 48 weeks.

Pharmacodynamic Results

Serum Phosphorus: Mean serum phosphorus levels are displayed graphically in FIG. 12.

Since the dose was adjusted based on the peak and trough phosphorus levels and on the pre-defined adjustment regimen, the KRN23 dose varies from subject to subject and throughout the course of the study. The mean KRN23 dose ranged from 0.541±0.2039 mg/kg to 0.865±0.2618 mg/kg in the study. During each of the 12 dosing intervals, mean serum phosphorus concentrations increased to clinically meaningful maximum levels by Day 7 or 14 and then declined but did not return to the pre-dose level prior to the next dosing. All subjects experienced an increase from baseline at all visits. The mean serum phosphorus concentration of these subjects increased from 1.85±0.282 mg/dL at pre-treatment Baseline (the first Phase I/11 clinical trial study Day 0) to a maximum level of 2.87±0.392 mg/dL on Day 14 of Dose Interval 1, and the maximum level remained within the range of 2.71±0.428 mg/dL to 2.96±0.468 mg/dL throughout the study. The maximum mean change from Baseline in serum phosphorus remained within the range from 0.87±0.444 mg/dL to 1.10±0.412 mg/dL throughout the study (Table 20). The mean serum phosphorus concentration at the end of the dose interval (Day 0) remained above baseline and the range was from 2.25±0.353 mg/dL to 2.52±0.436 mg/dL.

TABLE 20

Maximum Mean (±SD) Serum Phosphorus Levels and
Maximum Mean Change from Baseline for Subjects
Treated with KRN23 (Efficacy Analysis Set)

| | Serum Phosphorus Levels | | | |
|---|---|---|---|---|
| Dosing Interval | Day 0 Mean (SD), mg/dL | Time to Reach Maximum Level[a] | Maximum Level Mean (SD), mg/dL | Maximum Change from Baseline[b] Mean (SD), mg/dL |
| 1 | 1.88 (0.303), n = 21 | Day 14, n = 22 | 2.87 (0.392) | 1.01 (0.375) |
| 2 | 2.25 (0.353), n = 21 | Day 14, n = 21 | 2.95 (0.441) | 1.09 (0.467) |
| 3 | 2.43 (0.349), n = 21 | Day 7, n = 21 | 2.96 (0.468) | 1.10 (0.412) |
| 4 | 2.42 (0.396), n = 21 | Day 7, n = 21 | 2.92 (0.560) | 1.06 (0.516) |
| 5 | 2.35 (0.376), n = 20 | Day 7, n = 20 | 2.82 (0.396) | 0.95 (0.435) |
| 6 | 2.35 (0.330), n = 20 | Day 7, n = 20 | 2.94 (0.387) | 1.09 (0.436) |
| 7 | 2.37 (0.385), n = 20 | Day 7, n = 20 | 2.83 (0.315) | 0.99 (0.427) |
| 8 | 2.40 (0.422), n = 19 | Day 7, n = 18 | 2.87 (0.542) | 1.03 (0.532) |
| 9 | 2.42 (0.403), n = 18 | Day 7, n = 18 | 2.79 (0.456) | 0.94 (0.402) |
| 10 | 2.52 (0.436), n = 19 | Day 7, n = 19 | 2.85 (0.550) | 1.01 (0.549) |
| 11 | 2.29 (0.397), n = 19 | Day 7, n = 19 | 2.71 (0.428) | 0.87 (0.444) |
| 12 | 2.25 (0.301), n = 19 | Day 7, n = 19 | 2.73 (0.427) | 0.88 (0.468) |

$AUC_n$ = area under the concentration-time curve for the change from Baseline in serum phosphorus concentration during the nth dosing interval (n = 1, 2, 3, etc.);
NA = not applicable;
SD = standard deviation.
[a]Time to reach maximum mean serum phosphorus level relative to Day 0 of each dosing interval.
[b]Mean Baseline serum phosphorus level: 1.85 ± 0.282 mg/dL (n = 22). Maximum change from Baseline was achieved on the same relative dosing day as the maximum mean serum phosphorus level for all dosing intervals.

Peak and trough fluctuations from the maximum mean serum phosphorus value on Day 7 or 14 of a dosing interval to the minimum value on Day 0 of the following dosing interval were low throughout the study. For example, the maximum mean peak value of 2.96±0.468 mg/dL (Visit 10, Dose Interval 3, Day 7) was followed by a trough value of 2.42±0.396 mg/dL (Visit 13, Dose Interval 4, Day 0), for a 0.54 mg/dL difference (22.3%). The minimum mean trough values of 2.25±0.353 mg/dL (Visit 5, Dose Interval 2, Day 0) and 2.25±0.301 (Visit 45, Dose Interval 12, Day 0) followed peak values in the previous dosing intervals of 2.87±0.392 mg/dL (Visit 3, Dose Interval 1, Day 14) and 2.71±0.428 mg/dL (Visit 42, Dose Interval 11, Day 7), for differences of 0.62 mg/dL (27.6%) and 0.46 mg/dL (20.4%), respectively. The differences for 10 of the 11 of the available peak-trough pairs fell within the range of 17.9% to 27.6%; displaying a consistent PD effect over time. Inter-subject variability was also relatively low for serum phosphorus concentration. For example, between-subject variation of post-dose serum phosphorus levels (SD/mean×100%) was in the range of 13.4% to 15.8% for both paired trough and peak concentrations at the beginning of the study (Dose Interval 1-2) and the end of the study (Dose Interval 11-12). These results highlight the minimal variability and consistent PD effect.

Renal Tubular Maximum Reabsorption Rate of Phosphate/Glomerular Filtration Rate

Two hour urine samples collected on Days 14 and 25 after each KRN23 dose in each dosing interval were used to calculate TmP/GFR. Mean TmP/GFR values are displayed graphically in FIG. 13.

TmP/GFR is the proposed mechanism by which KRN23-mediated inhibition of excess FGF23 increases phosphorus levels. TmP/GFR followed the same pattern as serum phosphorus, suggesting that the increased serum phosphorus level following KRN23 treatment is mainly due to increased phosphorus reabsorption from renal proximal tubules. In all dosing intervals and all subjects, mean TmP/GFR was increased by a clinically significant amount on Day 14 compared to Baseline (Visit 2, Day 0 of this study), and then declined toward the pre-dose level prior to the next dosing (Table 23). Mean TmP/GFR was increased from a Baseline level of 1.564±0.3012 to a level within the range from 2.408±0.7205 mg/dL to 2.921±0.5990 mg/dL on Day 14 of each dosing interval; the Day 14 change from Baseline ranged from 0.849±0.7665 to 1.352±0.5892. Day 25 TmP/GFR levels ranged from 2.195±0.3819 mg/dL to 2.551±0.6538 mg/dL, and the change from Baseline ranged from 0.636±0.3085 to 1.004±0.6777.

For the 1 subject treated with Placebo in the bone sub-study, TmP/GFR levels remained little changed from Baseline (1.250 mg/dL) to the last evaluation completed as of the data cut-off date (Visit 8, Dose Interval 2, Day 25) (1.650 mg/dL) with post-dose levels ranging from 1.550 to 2.000 mg/dL.

1,25-Dihydroxy Vitamin D

Mean serum 1,25(OH)$_2$D levels for subjects treated with KRN23 are displayed graphically in FIG. 14.

During each of the 12 dosing intervals, mean serum 1,25(OH)$_2$D levels increased to a maximum level by Day 7 and then declined to a level comparable to Baseline prior to the next dosing. There is a trend toward decreased peak levels for 1,25(OH)$_2$D over time from the first to the last dosing interval (Table 24). The mean serum 1,25(OH)$_2$D level at Baseline (Visit 2, Day 0 of the first Phase I/II clinical trial study) was 36.4±12.64 and was increased on Day 7 of each dosing interval to a maximum within the range from 53.1±20.28 pg/mL to 92.0±43.21 pg/mL. The Day 7 maximum change from Baseline in serum 1,25(OH)$_2$D level remained within the range from 19.6±15.91 pg/mL to 63.4±35.52 pg/mL throughout the study.

For the 1 subject treated with Placebo in the bone sub-study, 1,25(OH)$_2$D levels remained little changed from Baseline (67.0 pg/mL) to the last evaluation completed as of the data cut-off date (Visit 10, Dose Interval 3, Day 7) (50.0 pg/mL) with post-dose levels ranging from 34.0 to 72.0 pg/mL.

TABLE 23

Mean (±SD) TmP/GFR Levels and Change from Baseline in Subjects Treated with KRN23 (Efficacy Analysis Set)

| Dosing Interval | TmP/GFR Levels | | | |
|---|---|---|---|---|
| | Day 14 Value Mean (SD), mg/dL | Change from Baseline$^a$ to Day 14 Mean (SD), mg/dL | Day 25 Value Mean (SD), mg/dL | Change from Baseline$^a$ to Day 25 Mean (SD), mg/dL |
| 1 | 2.655 (0.5660), n = 22 | 1.090 (0.4996) | 2.401 (0.5543), n = 19 | 0.823 (0.5708) |
| 2 | 2.907 (0.7448), n = 21 | 1.336 (0.7208) | 2.551 (0.6538), n = 20 | 1.004 (0.6777) |
| 3 | 2.602 (0.4876), n = 21 | 1.031 (0.5076) | 2.282 (0.4864), n = 21 | 0.711 (0.4812) |
| 4 | 2.921 (0.5990), n = 20 | 1.352 (0.5892) | 2.295 (0.4892), n = 21 | 0.724 (0.5208) |
| 5 | 2.600 (0.6415), n = 21 | 1.030 (0.5816) | 2.314 (0.4427), n = 20 | 0.754 (0.4601) |
| 6 | 2.735 (0.5993), n = 19 | 1.206 (0.6388) | 2.401 (0.4807), n = 20 | 0.847 (0.5337) |
| 7 | 2.754 (0.5730), n = 18 | 1.238 (0.5875) | 2.422 (0.5060), n = 19 | 0.862 (0.6200) |
| 8 | 2.677 (0.6045), n = 18 | 1.144 (0.6069) | 2.392 (0.5948), n = 19 | 0.832 (0.5492) |
| 9 | 2.636 (0.5144), n = 17 | 1.116 (0.4958) | 2.272 (0.4700), n = 18 | 0.739 (0.4822) |
| 10 | 2.408 (0.7205), n = 19 | 0.849 (0.7665) | 2.234 (0.6327), n = 19 | 0.674 (0.7502) |
| 11 | 2.595 (0.6046), n = 19 | 1.036 (0.5812) | 2.292 (0.5204), n = 19 | 0.733 (0.5231) |
| 12 | 2.572 (0.5380), n = 19 | 1.013 (0.5514) | 2.195 (0.3819), n = 19 | 0.636 (0.3085) |

NA = not applicable;
SD = standard deviation;
Tmp/GFR = ratio of the renal tubular maximum reabsorption rate of phosphate to glomerular filtration rate.
$^a$Baseline mean TmP/GFR: 1.564 ± 0.3012 mg/dL (n = 22).

TABLE 24

Maximum Mean (±SD) 1,25(OH)$_2$D Levels and Maximum Mean Change from Baseline in Subjects Treated with KRN23 (Efficacy Analysis Set)

| | | 1,25(OH)$_2$D Levels | | |
|---|---|---|---|---|
| Dosing Interval | Day 0 (Pre-dose) Mean (SD), pg/mL | Time to reach Maximum Level[a] | Maximum Level Mean (SD), pg/mL | Maximum Change from Baseline |
| 1 | 30.0 (12.79), n = 21 | Day 7 | 92.0 (43.21), n = 21 | 63.4 (35.52), n = 18 |
| 2 | 39.4 (15.85), n = 21 | Day 7 | 86.3 (31.49), n = 21 | 55.3 (25.16), n = 18 |
| 3 | 43.1 (16.39), n = 21 | Day 7 | 77.9 (25.89), n = 21 | 45.2 (20.72), n = 18 |
| 4 | 43.0 (17.06), n = 21 | Day 7 | 72.2 (20.67), n = 20 | 39.5 (19.02), n = 17 |
| 5 | 40.8 (13.61), n = 20 | Day 7 | 69.4 (24.50), n = 20 | 37.1 (20.90), n = 17 |
| 6 | 41.7 (20.43), n = 20 | Day 7 | 66.2 (21.96) n = 20 | 31.7 (17.05), n = 17 |
| 7 | 35.5 (15.50), n = 20 | Day 7 | 61.5 (19.03), n = 20 | 27.9 (15.60), n = 17 |
| 8 | 35.9 (13.73), n = 19 | Day 7 | 56.5 (21.74), n = 18 | 23.4 (15.36), n = 15 |
| 9 | 31.4 (10.41), n = 18 | Day 7 | 59.2 (24.12), n = 18 | 27.0 (22.29), n = 15 |
| 10 | 33.6 (11.49), n = 19 | Day 7 | 57.9 (27.05), n = 19 | 24.3 (24.30), n = 16 |
| 11 | 29.7 (10.54), n = 19 | Day 7 | 53.1 (20.28), n = 19 | 19.6 (15.91), n = 16 |
| 12 | 33.6 (10.85), n = 19 | Day 7 | 57.3 (20.18), n = 19 | 23.5 (15.43), n = 16 |

1,25(OH)$_2$D = 1,25-dihydroxy vitamin D;
NA = not applicable;
SD = standard deviation.
[a]Time to reach maximum mean 1,25(OH)$_2$D level relative to Day 0 of each dosing interval.

Other Pharmacodynamic Results

The mean values of serum total intact FGF23 levels at Baseline were recorded. The total FGF23 ECLA assay measures endogenous FGF23 in the presence of KRN23, whether complexed or unbound in serum. Standards (recombinant human FGF23 [rhFGF23]) and samples are incubated with excess amounts of KRN23 in a buffer matrix then detected by the assay. The assay measures the KRN23/FGF23 complex, which represents all endogenous FGF23 in the sample. The assay is limited since the endogenous FGF23/KRN23 complex in serum does not yield a parallel linear response to the rhFGF23/KRN23 complex standard curve, hence all results for total FGF23 using the ECLA are relative to the standard curve and can only be used to describe trends of increases or decreases in endogenous FGF23 concentration.

For the subjects who were to be treated with KRN23 in the first Phase I/II clinical trial, the mean serum total intact FGF23 level was 94.7±105.19 pg/mL at Baseline (Visit 2, Day 0 in first Phase I/II clinical trial) prior to any treatment with KRN23. After completing KRN23 treatments that study, this value had been increased to 42100.0±31524.88 pg/mL at the time of the first visit in second Phase I/II clinical trial (Visit 1, Dosing Interval 1, Day 0). Mean serum total intact FGF23 generally increased further with an increasing number of KRN23 doses in second Phase I/II clinical trial and reached a maximum of 510818.8±354649.07 pg/mL at Visit 45 (Dose Interval 12, Day 0) (FIG. 15).

The assay for unbound FGF23 is difficult to conduct in the presence of large amounts of bound FGF23, and it is difficult to be confident that the levels of free FGF23 are actually free in the circulation or are merely dissociating in the assay. Using the assay as developed, the mean levels of unbound intact FGF23 followed a pattern similar to that of total intact FGF23 through Visit 33 in subjects treated with KRN23; the mean values of the unbound form then decreased at Visits 37, 41 and 45 before rising again at Visit 49 (FIG. 16). The mean unbound intact FGF23 level was 103.5±62.77 pg/mL at Baseline and increased to 25283.3±33810.42 pg/mL at Visit 33 and 25657.9±13461.86 pg/mL at Visit 49. Although unbound intact FGF23 increased after KRN23 dosing, it represented only a small fraction of the total intact FGF23; the mean peak value of the unbound form is 5% that of total intact FGF23. It is therefore difficult to determine if this is accurate in this context.

KRN23 treatment led to increased serum phosphorus levels despite the apparent increases in total and unbound intact FGF23, which would suggest that whether free or not, the apparent free FGF23 was not active in vivo in this context.

In contrast to the effect of KRN23 treatment on serum phosphorus and TmP/GFR, no trends were noted in mean values over time for subjects treated with KRN23 for the following PD parameters: 25(OH)D, total calcium, ionized calcium, calcitonin, and iPTH in serum; or for the other PD parameters in urine, including 2-hour urine TRP, 2-hour urine calcium/creatinine ratio, 2-hour urine FECa, 24-hour urine phosphorus, 24-hour urine calcium, 24-hour urine creatinine, and 24-hour urine calcium/creatinine ratio.

Mean estradiol, testosterone, free testosterone, and SHBG over time for subjects treated with KRN23 were measured as well. No trends were noted for mean values over time in these parameters.

Bone Biomarkers

Bone Formation Parameters: Biomarkers of bone formation and resorption may provide an indication of treatment effect. Mean serum BALP, P1NP, and osteocalcin values over time were measured. P1NP increased from 69.6±29.86 ng/mL at baseline of the first Phase I/II clinical trial study, to a maximum of 170.4±100.79 ng/mL at Visit 17, which represents a percent change increase of 148.1%. The value remained elevated at 155.2±75.95 ng/mL on Visit 33/Dose Interval 9/Day 0. Serum osteocalcin and BALP also increased but to a lesser extent throughout the study. These data suggest that KRN23 increases bone formation and this can be the mechanism by which the bone quality may improve, the rickets changes reversed and the bone shape restored.

Bone Resorption Parameters: Mean serum CTx and NTx values over time were measured. For subjects treated with KRN23, numerical increases were noted in serum CTx (from 845.1±345.77 pg/mL on Visit 1/Dose Interval 1/Day 0 to 1090.5±570.55 pg/mL on Visit 17/Dose Interval 5/Day 0 and 1157.2±542.25 pg/mL on Visit 33/Dose Interval 9/Day 0) These changes in CTX are in the order of approximately 73% change from baseline. NTx also increased (from 246.2±578.65 nm bone collagen equivalents [BCE]/mL on Visit 1/Dose Interval 1/Day 0 to 346.5±611.50 nm BCE on Visit 17/Dose Interval 5/Day 0 and 344.6±566.55 nm BCE on Visit 33/Dose Interval 9/Day 0). These data demonstrate that KRN23 increases bone resorption as well as bone formation, and this increase in bone remodeling and turnover plus the normalization of the serum phosphorus levels is likely the key physiologic mechanism by which KRN23 will improve bone quality.

Efficacy Conclusions

In this study serum phosphorus is considered the efficacy end point and a key PD parameter. At the pre-treatment baseline, all subjects had serum phosphorus levels <2.5 mg/dL. Following KRN23 administration, the time of maximum PD effect (peak) was observed on Days 7 and 14. After the first dose of KRN23, 77.1% (Day 7) and 81.8% (Day 14) of subjects had increased serum phosphorus levels within the target range of >2.5 to ≤3.5 mg/dL. This peak effect was relatively consistent throughout the study ranging from 45.5% to 81.8%. The percentage of subjects within the target range was generally similar on Day 7 and 14. No serum phosphorus level >4.5 mg/dL was reported for any subject at any time point in the study.

Pharmacodynamic

TmP/GFR is the proposed mechanism by which KRN23-mediated inhibition of excess FGF23 increases phosphorus levels. KRN23 increased TmP/GFR; the magnitude of increase in TmP/GFR was clinically meaningful and correlates closely with the increases in serum phosphorus. The observed PD effect highlights the likely mechanism of KRN23 action by increasing phosphorus reabsorption and the distal tubular level serum phosphorus, thereby achieving the desired clinical effect.

During each of the 12 dosing intervals, mean serum 1,25(OH)2D levels increased to a maximum level by Day 7 and then declined to a level comparable to Baseline prior to the next dosing. 1,25 vitamin D is another PD parameter intimately linked to the mechanism of action of KRN23, and also increased following the same temporal profile: rapid increase post-dose, peaking at day 7, and returning towards baseline levels at the end of the dose interval.

All other metabolic parameters: 25(OH)D, total calcium, ionized calcium, calcitonin and iPTH; urine measures of TRP, calcium/creatinine ratio, and FECa, and 24-hour urine measures of phosphorus, calcium, creatinine, and calcium/creatinine ratio, did not change significantly. Therefore no off target effects were observed; changes in on-target PD parameters, essentially serum phosphorus and 1,25(OH)2D, did not appear to alter calcium and PTH metabolism.

The markers of bone formation increased significantly, particularly P1NP, and the markers of bone resorption, CTx and NTx, also increased albeit to a lesser degree. These results demonstrate that KRN23 increased bone remodeling which may lead to an improvement in bone quality in patients with XLH.

The maximum net production of bone mineralization requires the adequate levels of phosphate consistently over the cycle of dosing in the treatment of XLH. The present invention is partially based on the observation that changes in total bound FGF23 levels can occur during therapy with KRN23, leading to a complex PK/PD relationship with a typical pattern of waning of the treatment effect during the latter half of each monthly cycle despite adequate KRN23 drug PK and still remaining PD effect.

The FGF23 production increases during therapy with an anti-FGF23 agent that can benefit from the management of PK/PD in a manner unexpected by prior data. Although KRN23 monoclonal antibody drug PK data shows that a monthly injection may an adequate therapy, the increased levels of plasma bound FGF23 levels may provide a decline in the serum phosphate promoting activity. The serum phosphate pool comprises only 1% of total body phosphate, and would likely begin to fall during the latter half of the 1 month cycle leading to the potential reduction in net bone forming activity during the latter half of the dosing cycle. The phosphate level might not be declining enough to appreciate the impact of net phosphate balance in the body because of changing patterns of phosphate recovery from bone induced by the body to support the declining phosphate level. Despite the expected PK predicted plan to dose monthly and to teach away from the use of twice monthly dosing, the PD data showing increasing decline in phosphate over repeated dosing and the higher bound FGF23 production leads to the potential optimize dosing of the anti-FGF23 agent to dosing q2 week. This may be particularly advantageous in children.

The second change that is occurring is that during the dosing cycle is the likely decline in phosphate reabsorption which is likely due to less phosphate transporter expression during the latter half of the monthly dosing cycle. The cyclical pattern of increasing and decreasing transporter expression would likely lead to a the less efficient cyclical production and then destruction of the Na Pi cotransporter as the cycle drives up the transporter expression and has the transporter gets degraded again during the falling effect of KRN23. During a twice monthly, more frequent dosing, it is expected that the more efficient consistent capture of the FGF23 would result in an accumulative net effect on phosphate reabsorption from increased stable transporter expression that will be out of proportion to the monthly dose effect on FGF23. By not causing the destruction of the transporter every two weeks, the transporter protein's own PK might result in the accumulation effect of the transporter and an out of proportional benefit in phosphate reabsorption. Therefore instead of a proportional PD effect on serum phosphate, the more frequent dosing will result in a cumulative effect on NaPi transporter accumulation without decline, and now a higher achievable phosphate level.

The existing solution of treating FGF23 related disorders is the monthly dosing of a FGF23 antibody (e.g., KRN23) that is based on solid PK data in Phase 1 that would suggest clearly a once per month dose as sufficient and it may be an effective dose, especially patients with less phosphate needs like adults. In pediatrics or patients with higher phosphate needs, the increased levels of bound FGF23, and the associated PD curve of phosphate would be optimally served by a twice monthly dosing interval.

The invention is the novel insight into the unexpected dosing effect at twice monthly rather than monthly. This will be manifested through increased and more stable phosphate levels for the same total monthly dose that is out or proportion to the monthly dose effect as determined by the AUC for serum phosphate and potentially in bone treatment benefit.

Example 3: Inhibition of FGF23 with KRN23 Leads to Increased Bone Remodeling

Inventors of the present invention observed a specific effect of the inhibition of FGF23 with an antibody against FGF23 (e.g., KRN23) in treating and reversing the pathologic changes of osteomalacia caused by XLH in adults and children. Treatment with KRN23 corrects the phosphate homeostasis as was known previously. What is novel and unexpected is that the inhibition of FGF23 is activating a profound increase in bone remodeling with observed increases in markers of bone formation such as P1NP (serum type 1 pro-collagen/N-terminal) and osteocalcin, also increases marker of bone reabsorption CTX (carboxy-terminal collagen crosslink), see tables 18 to 21 below. Low bone remodeling reflects the histopathologic changes characteristics of osteomalacia, specifically the long "mineralization lag time and the increase on osteoid and osteoid wall thickness which explain the lack of osteoclast activity due to the absence of mineralized bone. While the blocking of FGF23 would be expected to change renal phosphate reabsorption, 1,25 VitD production and increased bone mineralization, the clinical data also suggest that the increases in bone remodeling (formation and reabsorption) will reverse osteomalacia and restore bone structure, density and improve bone quality preventing the bowing and allow for the normal shaping of the skeleton.

Increase in bone formation and reabsorption is the novel additional mechanism by which the underlying bone pathology in XLH, and in particular osteomalacia might be healed. This invention also postulates that the measurement of markers of bone formation and reabsorption can also be a way to monitor the regeneration of bone and the replacement of the poorly mineralize bone for normal lamellar mineralize bone. Since this can be managed actively, the dosing of KRN23 or similar FGF23 agent might be modulated based on bone resorption and synthesis markers as a score relevant to bone healing.

Previous treatment of XLH consist of supplementation therapy with oral phosphate and calcitriol or other vitamin D analogs, this treatment may improve some aspects of XLH disease, but it does not increase bone remodeling and therefore it is unclear whether it can improve osteomalacia in this patients. Osteomalacia is the reason why adult patients with XLH have bone pain, micro and stress fracture, delay in fracture healing. Biopsy data in our previous research of administrating FGF23 antibody in XLH model mice shows the change from osteomalacia to normal bone and the change in histomorphometry bone remodeling. See Aono et al. (Therapeutic Effects of Anti-FGF23 Antibodies in Hypophosphatemic Rickets/Osteomalacia. J Bone Miner Res. 2009).

Figure 17:
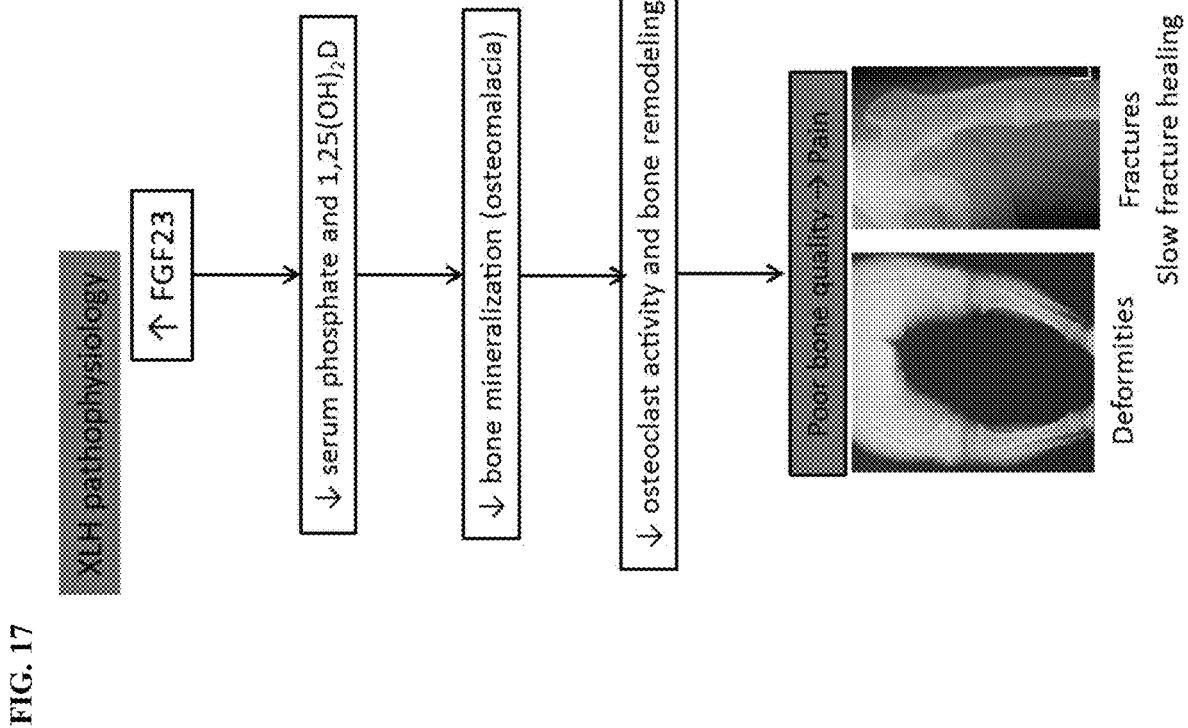
FIG. 17 depicts proposed model of X-linked hypophosphatemia pathophysiology, and treatment by the anti-FGF23 antibody KRN23.

The present invention indicates that in order to improve these clinical complications it is necessary to activate bone remodeling. This effect has never been observed with the current standard of care. Therefore, the present invention provides new methods of treating disorders due to abnormal FGF23 signaling, such as XLH, by activating bone remodeling. For example, according to FIG. 17, In XLH patients, increased FGF23 polypeptides lead to decreased serum phosphate and 1,25(OH)$_2$D, which results in decreased bone mineralization (osteomalacia). Osteomalacia in turn leads to decreased osteoclast activity and bone remodeling. As a result, the patients experience poor bone quality and pain, such as bone deformities, fractures, and slow fracture healing. Administration of anti-FGF23 ligand, such as KRN23 will inhibit the FGF23 signaling, normalize serum phosphate and 1,25(OH)$_2$D, therefore lead to increased bone mineralization and correction of osteomalacia. As a result, osteoclast and osteoblast activity and bone remodeling are up-regulated, and poor quality bone is replaced with normal lamellar bone, which ultimately leads to restored skeletal health and fracture healing.

TABLE 18

Summary of Bone Biomarkers by Visit/Day: P1NP Efficacy Analysis

| | P1NP (ng/mL) | | | | Change (ng/mL) from Baseline | | | |
|---|---|---|---|---|---|---|---|---|
| | Bone Substudy | | | | Bone Substudy | | | |
| Visit (Day)/ Relative Day | Open Label Treatment KRN23 | KRN23 | Placebo | Total KRN23 | Open Label Treatment KRN23 | KRN23 | Placebo | Total KRN23 |
| Visit 2 (D0)/0 | | | | | | | | |
| N | 26 | 1 | 1 | 27 | | | | |
| Mean | 62.7 | 100.0 | 91.0 | 64.1 | | | | |
| Median | 65.0 | 100.0 | 91.0 | 69.0 | | | | |
| Std. Dev. | 30.42 | NA | NA | 30.67 | | | | |
| Range (Min-Max) | (11, 123) | (100, 100) | (91, ) 91 | (11, 123) | | | | |
| Visit 8 (D28)/0 | | | | | | | | |
| N | 26 | 1 | 1 | 27 | 26 | 1 | 1 | 27 |
| Mean | 79.2 | 93.0 | 73.0 | 79.7 | 16.5 | −7.0 | −18.0 | 15.6 |
| Median | 83.0 | 93.0 | 73.0 | 88.0 | 16.0 | −7.0 | −18.0 | 16.0 |
| Std. Dev. | 33.18 | NA | NA | 32.65 | 15.94 | NA | NA | 16.27 |
| Range (Min-Max) | (23, 157) | (93, 93) | (73, 73) | (23, 157) | (−13, 54) | (−7, −7) | (−18, −18) | (−13, 54) |
| Visit 14 (D56)/0 | | | | | | | | |
| N | 23 | 1 | 1 | 24 | 23 | 1 | 1 | 24 |
| Mean | 93.5 | 186.0 | 66.0 | 97.4 | 29.6 | 86.0 | −25.0 | 32.0 |
| Median | 80.0 | 186.0 | 66.0 | 80.5 | 21.0 | 86.0 | −25.0 | 21.5 |
| Std. Dev. | 50.71 | NA | NA | 53.06 | 27.80 | NA | NA | 29.53 |
| Range (Min-Max) | (32, 191) | (186, 186) | (66, 66) | (32, 191) | (−2, 96) | (86, 86) | (−25, −25) | (−2, 96) |

TABLE 18-continued

Summary of Bone Biomarkers by Visit/Day: P1NP Efficacy Analysis

| | P1NP (ng/mL) | | | | Change (ng/mL) from Baseline | | | |
|---|---|---|---|---|---|---|---|---|
| | | Bone Substudy | | | | Bone Substudy | | |
| Visit (Day)/ Relative Day | Open Label Treatment KRN23 | KRN23 | Placebo | Total KRN23 | Open Label Treatment KRN23 | KRN23 | Placebo | Total KRN23 |
| Visit 20 (D84)/0 | | | | | | | | |
| N | 22 | 1 | 1 | 23 | 22 | 1 | 1 | 23 |
| Mean | 113.9 | 178.0 | 67.0 | 116.7 | 47.3 | 78.0 | −24.0 | 48.6 |
| Median | 112.0 | 178.0 | 67.0 | 115.0 | 39.0 | 78.0 | −24.0 | 40.0 |
| Std. Dev. | 62.17 | NA | NA | 62.19 | 39.07 | NA | NA | 38.70 |
| Range (Min-Max) | (28, 261) | (178, 178) | (67, 67) | (28, 261) | (−10, 140) | (78, 78) | (−24, −24) | (−10, 140) |
| End of Study - Visit 26 (D120) | | | | | | | | |
| N | 25 | 1 | 1 | 26 | 25 | 1 | 1 | 26 |
| Mean | 119.3 | 216.0 | 60.0 | 123.0 | 55.6 | 116.0 | −31.0 | 57.9 |
| Median | 114.0 | 216.0 | 60.0 | 114.5 | 41.0 | 116.0 | −31.0 | 43.5 |
| Std. Dev. | 74.11 | NA | NA | 75.05 | 58.86 | NA | NA | 58.88 |
| Range (Min-Max) | (24, 307) | (216, 216) | (60, 60) | (24, 307) | (−11, 204) | (116, 116) | (−31, −31) | (−11, 204) |
| Early Withdrawal | | | | | | | | |
| N | 1 | 0 | 0 | 1 | 1 | 0 | 0 | 1 |
| Mean | 69.0 | | | 69.0 | 32.0 | | | 32.0 |
| Median | 69.0 | | | 69.0 | 32.0 | | | 32.0 |
| Std. Dev. | NA | | | NA | NA | | | NA |
| Range (Min-Max) | (69, 69) | | | (69, 69) | (32, 32) | | | (32, 32) |

TABLE 19

Summary of $AUEC_{last}$ of P1NP Change from Baseline Overall Dosing Intervals Efficacy Analysis Set

| | $AUEC_{last}$ | | | |
|---|---|---|---|---|
| | Open Label Treatment | Bone Substudy | | Total |
| | KRN23 | KRN23 | Placebo | KRN23 |
| Visit 1 through Visit 49 | | | | |
| N | 20 | 1 | 0 | 21 |
| Mean | 25373.33 | 8904.00 | | 24589.07 |
| Median | 23998.00 | 8904.00 | | 23494.00 |
| Std. Dev. | 19160.505 | NA | | 19018.013 |
| Range (Min-Max) | (2854.5, 73669.0) | (8904.0, 8904.0) | | (2854.5, 73669.0) |

TABLE 20

Summary of Bone Biomarkers by Visit/Day: CTx Efficacy Analysis

| | CTx (ng/mL) | | | | Change (ng/mL) from Baseline | | | |
|---|---|---|---|---|---|---|---|---|
| | | Bone Substudy | | | | Bone Substudy | | |
| Visit (Day)/ Relative Day | Open Label Treatment KRN23 | KRN23 | Placebo | Total KRN23 | Open Label Treatment KRN23 | KRN23 | Placebo | Total KRN23 |
| Visit 2 (D0)/0 | | | | | | | | |
| N | 25 | 1 | 1 | 26 | | | | |
| Mean | 750.1 | 799.0 | 613.0 | 752.0 | | | | |

TABLE 20-continued

Summary of Bone Biomarkers by Visit/Day: CTx Efficacy Analysis

| | CTx (ng/mL) | | | | Change (ng/mL) from Baseline | | | |
|---|---|---|---|---|---|---|---|---|
| | | Bone Substudy | | | | Bone Substudy | | |
| Visit (Day)/<br>Relative Day | Open Label<br>Treatment<br>KRN23 | KRN23 | Placebo | Total<br>KRN23 | Open Label<br>Treatment<br>KRN23 | KRN23 | Placebo | Total<br>KRN23 |
| Median | 742.0 | 799.0 | 613.0 | 744.0 | | | | |
| Std. Dev. | 397.36 | NA | NA | 389.45 | | | | |
| Range (Min-Max) | (214, 1899) | (799, 799) | (613, 613) | (214, 1899) | | | | |
| Visit 8 (D28)/0 | | | | | | | | |
| N | 26 | 1 | 1 | 27 | 25 | 1 | 1 | 26 |
| Mean | 803.8 | 623.0 | 806.0 | 797.1 | 24.0 | −176.0 | 193.0 | 16.3 |
| Median | 701.0 | 623.0 | 806.0 | 690.0 | −5.0 | −176.0 | 193.0 | −6.5 |
| Std. Dev. | 509.79 | NA | NA | 501.10 | 160.30 | NA | NA | 161.89 |
| Range (Min-Max) | (171, 2240) | (623, 623) | (806, 806) | (171, 2240) | (−208, 471) | (−176, −176) | (193, 193) | (−208, 471) |
| Visit 14 (D56)/0 | | | | | | | | |
| N | 26 | 1 | 1 | 27 | 25 | 1 | 1 | 26 |
| Mean | 828.9 | 653.0 | 913.0 | 822.4 | 76.9 | −146.0 | 300.0 | 68.3 |
| Median | 764.0 | 653.0 | 913.0 | 758.0 | 61.0 | −146.0 | 300.0 | 58.0 |
| Std. Dev. | 444.32 | NA | NA | 437.01 | 168.29 | NA | NA | 170.59 |
| Range (Min-Max) | (146, 1926) | (653, 653) | (913, 913) | (146, 1926) | (−170, 481) | (−146, −146) | (300, 300) | (−170, 481) |
| Visit 20 (D84)/0 | | | | | | | | |
| N | 23 | 1 | 1 | 24 | 22 | 1 | 1 | 23 |
| Mean | 991.6 | 1030.0 | 678.0 | 993.2 | 227.2 | 231.0 | 65.0 | 227.3 |
| Median | 900.0 | 1030.0 | 678.0 | 927.0 | 162.5 | 231.0 | 65.0 | 184.0 |
| Std. Dev. | 611.08 | NA | NA | 597.70 | 280.16 | NA | NA | 273.72 |
| Range (Min-Max) | (176, 2397) | (1030, 1030) | (678, 678) | (176, 2397) | (−133, 927) | (231, 231) | (65, 65) | (−133, 927) |
| End of Study - Visit 26 (D120) | | | | | | | | |
| N | 25 | 1 | 1 | 26 | 24 | 1 | 1 | 25 |
| Mean | 954.3 | 774.0 | 570.0 | 947.3 | 187.4 | −25.0 | −43.0 | 178.9 |
| Median | 859.0 | 774.0 | 570.0 | 816.5 | 108.5 | −25.0 | −43.0 | 102.0 |
| Std. Dev. | 513.87 | NA | NA | 504.73 | 261.57 | NA | NA | 259.56 |
| Range (Min-Max) | (213, 2170) | (774, 774) | (570, 570) | (213, 2170) | (−162, 888) | (−25, −25) | (−43, −43) | (−162, 888) |
| Early Withdrawal | | | | | | | | |
| N | 1 | 0 | 0 | 1 | 1 | 0 | 0 | 1 |
| Mean | 384.0 | | | 384.0 | −79.0 | | | −79.0 |
| Median | 384.0 | | | 384.0 | −79.0 | | | −79.0 |
| Std. Dev. | NA | | | NA | NA | | | NA |
| Range (Min-Max) | (384, 384) | | | (384, 384) | (−79, −79) | | | (−79, −79) |

TABLE 21

Summary of AUEC$_{last}$ of CTx Change from Baseline Overall Dosing Intervals
Efficacy Analysis Set

| | AUEC$_{last}$ | | | |
|---|---|---|---|---|
| | Open Label<br>Treatment | Bone Substudy | | Total |
| | KRN23 | KRN23 | Placebo | KRN23 |
| Visit 1 through Visit 49 | | | | |
| N | 19 | 1 | 0 | 20 |
| Mean | 48870.26 | −3024.00 | | 46275.55 |
| Median | 40327.00 | −3024.00 | | 39745.00 |
| Std. Dev. | 76325.295 | NA | | 75190.381 |
| Range (Min-Max) | (−58443.0, 222166.0) | (−3024.0, −3024.0) | | (−58443.0, 222166.0) |

Example 4: A Randomized, Open-Label, Dose Finding, Phase 2 Study to Assess the Pharmacodynamics and Safety of the Anti-FGF23 Antibody, KRN23, in Pediatric Patients with X-Linked Hypophosphatemia (XLH)

Rationale:

X-linked hypophosphatemia (XLH) is a disorder of renal phosphate wasting, and the most common heritable form of rickets. In XLH patients, high circulating levels of fibroblast growth factor 23 (FGF23) impair normal phosphate reabsorption in the kidney. Hypophosphatemia and low-normal circulating 1,25-dihydroxyvitamin D (1,25(OH)$_2$D) levels are typical biochemical findings. Low serum phosphorus levels result in hypomineralization of bone and associated abnormalities including rickets, bowing of the legs, and short stature. The current standard of care (SOC) therapy consists of multiple daily doses of oral phosphate combined with appropriate doses of active vitamin D metabolites. SOC therapy, when taken with a high degree of compliance and monitoring, can improve the skeletal disease but often does not fully address the bone and growth abnormalities nor does it target the pathophysiological cause of the disease: renal phosphate wasting induced by high FGF23 levels. SOC therapy also requires careful monitoring to avoid potential risks such as nephrocalcinosis, hypercalciuria, and hyperparathyroidism. More efficacious, safer, and convenient therapies clearly are needed.

KRN23 is a recombinant fully human monoclonal IgG1 antibody being developed to treat XLH by binding and inhibiting FGF23 activity, thereby restoring normal phosphate homeostasis. Three clinical trials have been conducted in adults with XLH. A Phase 1 study established the pharmacokinetic (PK) profile of KRN23. A Phase 1/2 study and associated extension study evaluated the pharmacodynamics (PD) of KRN23 on phosphate metabolism and related measures of the phosphate-calcium mineral control system. The safety data from these studies has shown that KRN23 in single and repeated monthly doses up to 1.0 mg/kg was well tolerated by adult XLH subjects. KRN23 sufficiently increased serum phosphorus levels, such that improvements in bone physiology, structure and function would be expected. These data support the initiation of further studies to evaluate the therapeutic benefit of KRN23 in children who experience the most severe physical and health manifestations associated with XLH. Currently, there are no approved treatments and a high unmet medical need in pediatric XLH patients.

Adults and children with XLH have the same underlying defect but are at a different stage of the disease. In childhood, normal phosphorus levels are higher to promote bone formation, whereas in adults, the normal range is lower coincident with reduced demand for bone formation. Therefore, smaller, more frequent dosing may be preferred for pediatric hypophosphatemic patients to maximize treatment effect without a plateau, drive serum phosphorus levels closer to the normal range and minimize the troughs. This Phase 2 study will examine the PD and safety of KRN23 administered at multiple doses and dose regimens in pediatric XLH patients.

The study will consist of two periods: a 16-week individual dose Titration Period and a 48-week Treatment Period. The dose response of KRN23 will be evaluated at 3 starting dose levels. Monthly (Q4) and biweekly (i.e. every other week; Q2) dosing regimens will also be compared. KRN23 dosing will be individually adjusted every 4 weeks as needed, according to serum phosphorus levels. The goal is to achieve stable serum phosphorus levels in the target range, while minimizing changes in the calcium control system. Data collected in this study will establish the dosing strategy, and provide information for the design and endpoint selection for a Phase 3 clinical trial in children with XLH.

Objectives

The objectives of the study are to:
- Identify a dose and dosing regimen of KRN23, based on safety and PD effect, in pediatric XLH patients
- Establish the safety profile of KRN23 for the treatment of children with XLH including ectopic mineralization risk, cardiovascular effects, and immunogenicity profile
- Characterize the PK/PD of the KRN23 doses tested in the monthly (Q4) and biweekly (Q2) dose regimens in pediatric XLH patients
- Determine the PD effects of KRN23 treatment on markers of bone health in pediatric XLH patients
- Obtain a preliminary assessment of the clinical effects of KRN23 on bone health and deformity, muscle strength, and motor function
- Obtain a preliminary assessment of the effects of KRN23 on patient-reported outcomes, including pain, disability, and quality of life in pediatric XLH patients Study Design and Methodology:

This study is a randomized, multicenter, open-label, dose finding, Phase 2 study. The study will be conducted in prepubescent children aged 5-12 years with XLH to assess the PD and safety of KRN23 administered via subcutaneous (SC) injections monthly (Q4, 28 days±3 days) or biweekly (Q2, 14 days±2 days) for a total of 64 weeks. The study consists of a 16-week individual dose Titration Period, followed by a 48-week Treatment Period. The study will enroll approximately 30 pediatric patients with XLH and radiographic evidence of bone disease. Subjects will need to discontinue oral phosphate and vitamin D metabolite therapy prior to randomization and throughout the duration of the study.

There will be 3 cohorts in this study (n=10 per cohort); each with a Q4 (n=5) and Q2 (n=5) dosing group. Subjects will be randomized 1:1 to the Q4 or Q2 dosing regimens within each cohort; randomization will be stratified on subject gender. In order to maintain a level of gender balance, no more than 20 patients of either sex can be enrolled in the study. The cohorts will be enrolled sequentially. The first cohort will examine the lowest doses (0.2 mg/kg Q4 and 0.1 mg/kg Q2) and will be enrolled first. As an added precautionary measure in this pediatric population, the second cohort (0.4 mg/kg Q4 and 0.2 mg/kg Q2) cannot begin dosing until the fourth subject in the first cohort completes the Week 4 visit. The third cohort will be administered the highest starting doses (0.6 mg/kg Q4 and 0.3 mg/kg Q2).

The initial 16-week Titration Period is intended to identify the KRN23 dose required to achieve the target peak PD effect. The goal is to identify an individualized KRN23 dose which maintains serum phosphorus levels in the target range, however the dose level should not exceed 2.0 mg/kg for the Q4 regimen and 1.0 mg/kg for the Q2 regimen. The target fasting serum phosphorus range for this study is 3.5-4.5 mg/dL (1.13-1.45 mmol/L), based on the peak PD effect of KRN23.

The dose will be adjusted every 4 weeks, as needed, based on 2-week post-dose (peak) fasting serum phosphorus levels. The KRN23 dose titration scheme (Table 22) will be used as a guideline should the peak fasting serum phosphorus level fall outside of the target range. If the serum phosphorus level is rising but has not yet reached the acceptable target range by the end of the Titration Period, the titration can continue into the Treatment Period until the target range is reached provided there are no safety concerns.

TABLE 22

KRN23 Dose Titration Scheme

| Serum Phosphorus (2 weeks Post-Dose) | Dose Adjustment [1] |
|---|---|
| <3.5 mg/dL [2] <1.13 mmol/L | In 2 weeks, increase dose by 0.1 mg/kg for Q2 OR 0.2 mg/kg for Q4 |
| 3.5-4.5 mg/dL 1.13-1.45 mmol/L | Repeat previous dose |
| >4.5 mg/dL (1.45 mmol/L) and ≤ age adjusted ULN | In 2 weeks, decrease dose by 0.1 mg/kg for Q2 OR 0.2 mg/kg for Q4 |
| > age adjusted ULN | Skip next 2 doses for Q2 OR skip next dose for Q4, then re-initiate dosing at last dose level |

[1] Dose adjustments for subjects assigned to the Q2 regimen will only be made after 2 consecutive peak measurements.
[2] If a subject's serum phosphorus level has not increased, as defined by a change no greater than 0.1 mg/dL, after 2 consecutive dose escalations, even if the target range has not been achieved, then the previous dose will be considered that subject's optimized dose and not escalated further.

Figure 18:
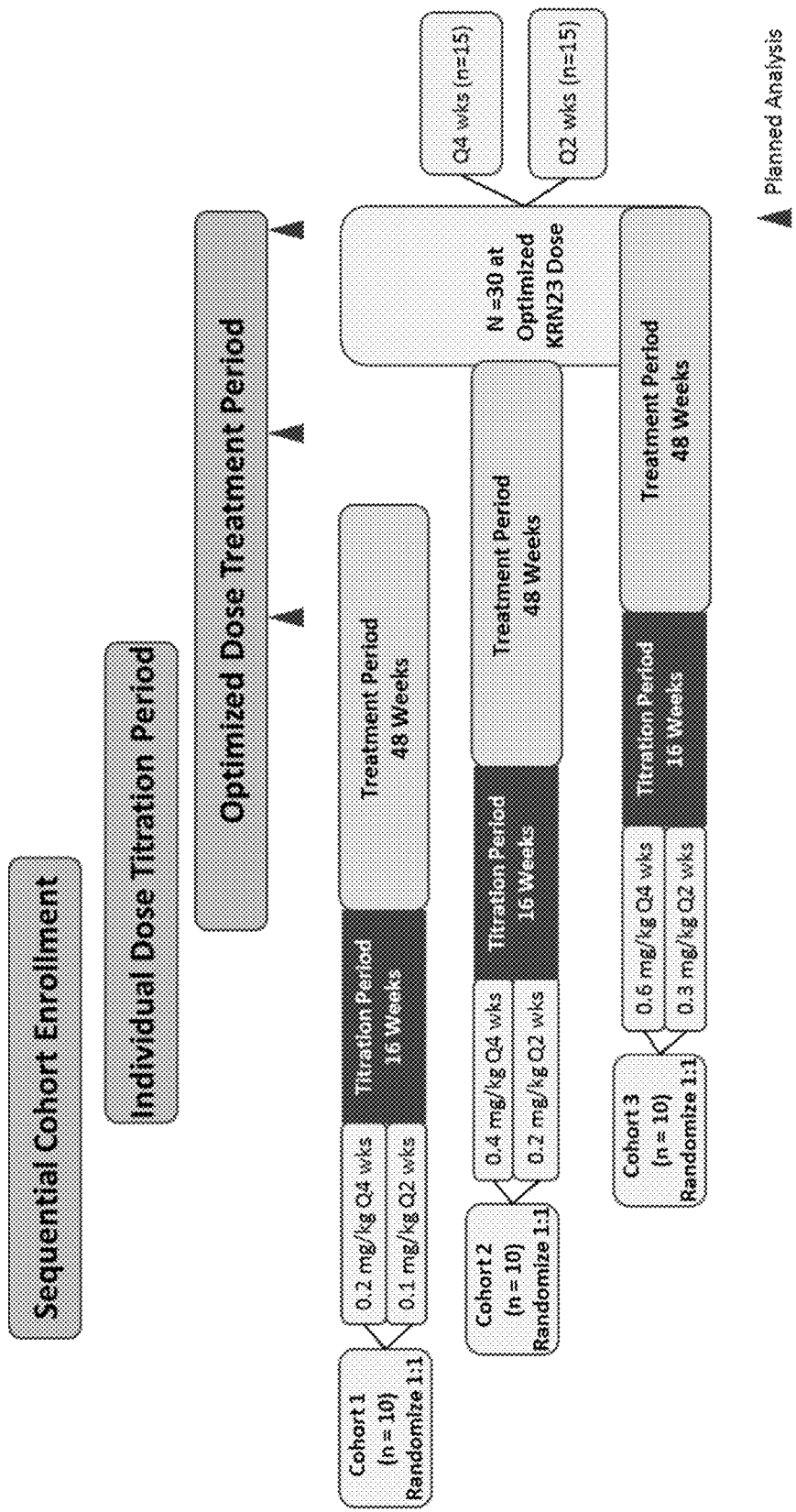
FIG. 18 depicts a schematic of the proposed Phase 2 study design.

At the end of the Titration Period, the population of 30 subjects will consist of essentially two groups of 15 subjects, each with individually optimized dosing of KRN23 at either a Q4 week or Q2 week frequency. An analysis of safety and select PD data is planned at the end of the Titration Period (Week 16). A second analysis is planned following the first 24-weeks of the Treatment Period (Week 40) to compare treatment outcomes to baseline (pre-dose). FIG. 18 provides a schematic of the overall study design.

Number of Subjects:

Approximately 30 pediatric subjects will be enrolled in the study. Subjects who withdraw or are removed from the study may be replaced on a case-by-case basis.

Diagnosis and Criteria for Inclusion and Exclusion:

Individuals eligible to participate in this study must meet all of the following criteria:

1) Male or female, aged 5-12 years, inclusive, with open growth plates
2) Tanner stage of 2 or less based on breast and testicular development (assessed only in children ≥8 years of age)
3) Diagnosis of XLH supported by ONE of the following:
   Confirmed PHEX mutation in the patient or a directly related family member with appropriate X-linked inheritance
   Serum iFGF23 level ≥30 pg/mL by Kainos assay
4) Biochemical findings associated with XLH including:
   Serum phosphorus ≤2.8 mg/dL (0.904 mmol/L)*
   Serum creatinine within age-adjusted normal range*
5) Short stature as defined by standing height <25% percentile for age and gender (per CDC 2000)
6) Radiographic evidence of active bone disease including rickets in the wrists and/or knees, AND/OR femoral/tibial bowing
7) Willing to provide access to prior medical records for the collection of historical growth, biochemical and radiographic data, and disease history.
8) Provide written or verbal assent (if possible) and written informed consent by a legally authorized representative after the nature of the study has been explained, and prior to any research-related procedures
9) Must, in the opinion of the investigator, be willing and able to complete all aspects of the study, adhere to the study visit schedule and comply with the assessments.

Individuals who meet any of the following exclusion criteria will not be eligible to participate in the study:

1) Use of a pharmacologic vitamin D metabolite or analog (e.g. calcitriol, doxercalciferol, and paricalcitol) within 14 days prior to Screening Visit 2; washout will take place during the Screening Period
2) Use of oral phosphate within 7 days prior to Screening Visit 2; washout will take place during the Screening Period
3) Use of aluminum hydroxide antacids (e.g. Maalox® and Mylanta®), systemic corticosteroids, and thiazides within 7 days prior to Screening Visit 1
4) Use of growth hormone within 1 year prior to Screening Visit 1
5) Use of bisphosphonates for 6 months or more in the 2 years prior to Screening Visit 1
6) Presence of nephrocalcinosis on renal ultrasound graded ≥3 based on the following scale:
   0=Normal
   1=Faint hyperechogenic rim around the medullary pyramids
   2=More intense echogenic rim with echoes faintly filling the entire pyramid
   3=Uniformly intense echoes throughout the pyramid
   4=Stone formation: solitary focus of echoes at the tip of the pyramid
7) Planned or recommended orthopedic surgery, including staples, 8-plates or osteotomy, within the clinical trial period
8) Hypocalcemia or hypercalcemia, defined as serum calcium levels outside the age-adjusted normal limits*
9) Evidence of tertiary hyperparathyroidism as determined by the Investigator
10) Use of medication to suppress PTH (e.g. Sensipar®, cinacalcet) within 2 months prior to Screening Visit 1
11) Presence or history of any condition that, in the view of the investigator, places the subject at high risk of poor treatment compliance or of not completing the study.
12) Presence of a concurrent disease or condition that would interfere with study participation or affect safety
13) Positive for human immunodeficiency virus antibody, hepatitis B surface antigen, and/or hepatitis C antibody
14) History of recurrent infection or predisposition to infection, or of known immunodeficiency
15) Use of a therapeutic monoclonal antibody within 90 days prior to Screening Visit 1 or history of allergic or anaphylactic reactions to any monoclonal antibody
16) Presence or history of any hypersensitivity to KRN23 excipients that, in the judgment of the investigator, places the subject at increased risk for adverse effects.
17) Use of any investigational product or investigational medical device within 30 days prior to screening, or requirement for any investigational agent prior to completion of all scheduled study assessments.

* Criteria to be determined based on overnight fasting (min. 8 hours) values collected at Screening Visit 2

Investigational Product, Dose and Mode of Administration: KRN23 is a sterile, clear, colorless, and preservative-free solution in single-use 5-mL vials containing 1 mL of KRN23 at a concentration of 10 mg/mL or 30 mg/mL. Subjects will receive study drug via SC injection to the abdomen, upper arms and thighs; the injection site will be rotated with each injection. Subjects will be sequentially enrolled into the cohorts, starting with the lowest dose group, and randomized to a dosing regimen (Q2 or Q4) (FIG. 2.1) then individually titrated to achieve a target overnight fasting serum phosphorus range of 3.5-4.5 mg/dL (1.13-1.45 mmol/L). The maximum dose allowed in this protocol is 2.0 mg/kg for the Q4 regimen, and 1.0 mg/kg for the Q2 regimen.

Reference Therapy, Dose and Mode of Administration: The study design is open-label; all subjects will receive investigational product. No placebo or reference therapy will be administered in this study.

Duration of Treatment: The study consists of two periods: a 16-week individual dose Titration Period, followed by a 48-week Treatment Period. The planned duration of treatment in this study is 64 weeks.

Criteria for Evaluation:
Pharmacodynamic*:
Serum phosphorus
Serum 1,25(OH)2D
Urinary phosphorus
Phosphate reabsorption: ratio of renal tubular maximum reabsorption rate of phosphate to glomerular filtration rate (TmP/GFR), and tubular reabsorption of phosphate (TRP)
Bone biomarkers: procollagen type 1 N-propeptide (P1NP), carboxy-terminal cross-linked telopeptide of type I collagen (CTx), and alkaline phosphatase (ALP)
Blood and urine to be collected after a minimum overnight fasting time of 8 hours and prior to drug administration (if applicable) per dosing regimen.
Efficacy—Bone Health:
Growth: standing height, sitting height, arm length and leg length will be measured. Growth percentiles based on standing height will be derived prior to and following treatment if historical data are available
Severity of rickets and epiphyseal (growth plate) abnormalities: central readings of bilateral posteroanterior (PA) hand/wrist and anteroposterior (AP) knee radiographs using a disease-specific qualitative Radiograph Global Impression of Change (RGI-C) scoring system and a modified version of a scale developed for nutritional rickets
Lower extremity deformity assessed by intercondylar distance and intermalleolar distance. Specific abnormalities related to lower extremity deformity and bowing observed on standing long leg films will also be evaluated using the qualitative RGI-C scoring system
Bone Mineral Density or Content at the cortical and trabecular compartment as assessed by XtremeCT of the forearm and tibia (performed at select sites depending on availability of equipment)
Efficacy—Clinical Outcomes:
Walking ability: Six Minute Walk Test (6MWT) total distance and percent of predicted normal
Gross motor function: Bruininks-Oseretsky Test of Motor Proficiency—Second Edition (BOT-2) subtests to assess running speed, agility and strength
Muscle strength: bilateral hand-held dynamometry (HHD) in the following muscle groups: gross grip, knee flexors, knee extensors, hip flexors, hip extensors and hip abductors
Functional disability and pain: Pediatric Orthopedic Society of North America Pediatric Outcomes Data Collection Instrument (POSNA PODCI)
Health-Related Quality of Life: SF-10 for Children Health Survey (SF-10)
Pharmacokinetic:
Serum KRN23 (pre-dose level)
Safety Assessments: Safety will be evaluated by the incidence, frequency and severity of adverse events (AEs) and serious adverse events (SAEs), including clinically significant changes from baseline to scheduled time points. General safety variables include:
Vital signs and weight
Interval history and physical examinations
GFR
Chemistry, hematology, and urinalysis, including additional KRN23/XLH biochemical parameters of interest (serum 25(OH)D, amylase, creatinine, and iFGF23 [total, bound and unbound])
Anti-KRN23 antibody testing and dose-limiting toxicities
Concomitant medications
Ectopic mineralization safety assessments include:
Renal ultrasound
ECHO and ECG
Serum calcium, phosphorus and iPTH; urinary calcium and creatinine Data Monitoring Committee (DMC): An independent DMC that includes members with expertise in metabolic bone disease and the conduct of clinical trials in children will act in an advisory capacity to monitor subject safety on a routine basis throughout the trial. The DMC will also meet for quarterly data reviews.

Statistical Methods: A full description of the statistical evaluations will be provided in the Statistical Analysis Plan.

Sample Size: A sample size of 10 per cohort will provide at least 90% power to detect a serum phosphorus increase from baseline of at least 0.8 mg/dL, assuming a standard deviation of 0.7 mg/dL or smaller, at the 2-sided level of significance of 0.05. In addition, a total sample size of 30 subjects (15 subjects per Q4 or Q2 regimen) will provide at least 90% power to detect a 0.5 mg/dL difference between the two dosing regimens assuming a standard deviation of 0.4 and 2-sided level of significance of 0.05. Phosphate and mineral control are adequately powered based on the clinical experience to date with KRN23. The degree of powering for bone health will depend on the degree of effect expected which is not known. However, powering for adequate phosphate control should provide the potential for improved bone health based on prior experience with oral phosphate replacement therapy.

Pharmacodynamics and Efficacy Analysis: Analyses of PD and efficacy comparing the two dosing regimens will be performed at Week 40 and Week 64 with Week 0 as the baseline. In addition, PD and safety data will be summarized for each cohort and each dose regimen within a cohort after each cohort has completed the Titration Period (Week 16). Descriptive statistics will be used to summarize the data. For continuous variables, the mean, standard error, median, minimum, and maximum will be provided. For discrete data, the frequency and percent distributions will be provided. Changes over time and the association of the efficacy with the PD variables will be summarized and evaluated.

Safety Analysis: All subjects who receive any amount of study drug will be included in the safety analysis. Safety of each cohort and each dose regimen within a cohort will be assessed.

The multiple-dose, dose escalation Phase 1/2 study of Example 1 was conducted in adult XLH subjects. KRN23 was well tolerated following SC administration of 4 intra-subject escalating doses (0.05 mg/kg→0.1 mg/kg→0.3 mg/kg→0.6 mg/kg) administered once per 28 days. The proportion of KRN23-treated subjects with serum phosphorus levels in the target range (>2.5 to ≤3.5 mg/dL) increased with KRN23 dose level but did not exceed the upper limit of normal (4.5 mg/dL) in any subject at any time point. A direct PK-PD relationship between serum KRN23 concentrations and serum phosphorus levels was noted in the study. In an associated extension study of Example 2, doses up to 1.0 mg/kg KRN23 administered monthly were well tolerated by adult XLH subjects over a period of 48 weeks.

Adults and children with XLH have the same underlying defect but are at a different stage of the disease. In childhood, normal phosphorus levels are higher to promote bone formation, whereas in adults, the normal range is lower coincident with reduced demand for bone formation. Successful treatment of XLH requires sustained increases in serum phosphorus levels (Carpenter et al. 2011). Smaller, more frequent dosing may be preferred for pediatric hypophosphatemic patients to maximize treatment effect by maintaining serum phosphorus levels closer to the normal range and minimize the troughs. Therefore, the key objectives of this study are to determine both the optimal KRN23 dosing regimen for pediatric XLH patients and identify an acceptable dose that will allow for the improvement in rickets and associated clinical consequences, while avoiding hypercalciuria, hypercalcemia and hyperparathyroidism.

The dose-finding goal of this study is to identify an individualized KRN23 dose which maintains serum phosphorus levels in the target range. Dose finding will be conducted progressively in three distinct dosing cohorts, each evaluating a different starting dose level and dose regimen (Q4 or Q2). Starting doses for all three cohorts are below the highest doses studied in adult XLH (1 mg/kg administered monthly). Dose escalation will be individually titrated based on PD effects on serum phosphorus, safety and tolerability. Dosing will be initiated and titrated in a stepwise, controlled fashion over a 16-week period to achieve serum phosphorus levels in a target range below the age-adjusted upper limit of normal.

Since phosphorus requirements in growing children are greater than in adults, the design provides the provision to increase the dose level as high as 2.0 mg/kg for the Q4 regimen and 1.0 mg/kg for the Q2 regimen. Previous studies with KRN23 in adult XLH patients did not show any "off target" effects, therefore the safety profile is expected to be related solely to the PD effect, essentially increased serum phosphorus. Since the serum phosphorus target range is defined well below the upper limit of normal, the likelihood of a dose-related safety issue is low. The efficacy data on phosphate control from these previous studies also suggest there is a plateau in effect between 0.6-1.0 mg/kg which may or may not be the case in pediatric patients in whom phosphate metabolism is clearly different. Therefore, the protocol allows limited flexibility to adapt to incrementally higher doses, if the expected doses based on adult data are inadequate to achieve an acceptable increase in serum phosphorus within the accepted safe range.

The target fasting serum phosphorus range for this study is 3.5-4.5 mg/dL (1.13-1.45 mmol/L), based on the peak PD effect of KRN23, which is approximately 14 days post-dose. The target range represents the low to mid-range of normal values in children. This level is sufficient to improve rickets and other bone defects, while minimizing the risk of ectopic mineralization. The dose will be adjusted every 4 weeks, as needed, based on 2-week post-dose (peak) fasting serum phosphorus levels according to the titration scheme detailed below. The titration scheme (Table 23) will be used as a guideline for dose adjustments should the peak fasting serum phosphorus level fall outside of the target range. If the serum phosphorus level is rising but has not yet reached the acceptable target range by the end of the Titration Period, the titration can continue into the Treatment Period until the target range is reached provided there are no safety concerns.

TABLE 23

KRN23 Dose Titration Scheme

| Serum Phosphorus (2 weeks Post-Dose) | Dose Adjustment [1] |
|---|---|
| <3.5 mg/dL [2]<br>  <1.13 mmol/L | In 2 weeks, increase dose by 0.1 mg/kg for Q2 OR 0.2 mg/kg for Q4 |
| 3.5-4.5 mg/dL<br>  1.13-1.45 mmol/L | Repeat previous dose |
| >4.5 mg/dL (1.45 mmol/L) and ≤ age adjusted ULN | In 2 weeks, decrease dose by 0.1 mg/kg for Q2 OR 0.2 mg/kg for Q4 |
| > age adjusted ULN | Skip next 2 doses for Q2 OR skip next dose for Q4, then re-initiate dosing at last dose level |

[1] Dose adjustments for subjects assigned to the Q2 regimen will only be made after 2 consecutive peak measurements.
[2] If a subject's serum phosphorus level has not increased, as defined by a change no greater than 0.1 mg/dL, after 2 consecutive dose escalations, even if the target range has not been achieved, then the previous dose will be considered that subject's optimized dose and not escalated further.

The planned duration of treatment in this study is 64 weeks. The study consists of two periods: a 16-week individual dose Titration Period, followed by a 48-week Treatment Period.

Example 5: Preliminary Results from Pediatric Phase 2 Study

This example illustrates that Q2W dosing of KRN23 provides stable and steady increases in serum phosphorus levels, while a Q4W dosing regimen produces larger serum phosphorus peaks and troughs.

In this example, there were 18 XLH patients in the Q2W treatment group, with 3 cohorts: (1) with a starting dose of 0.1 mg/kg, (2) with a starting dose of 0.2 mg/kg, and (3) with a starting dose of 0.3 mg/kg. There were also 18 patients in the Q4W treatment group, with 3 cohorts: (1) with a starting dose of 0.2 mg/kg, (2) with a starting dose of 0.4 mg/kg, and (3) with a starting dose of 0.6 mg/kg. Patients ranged in age from 5-12 years, with a mean age of 8.2 years.

Figure 19:
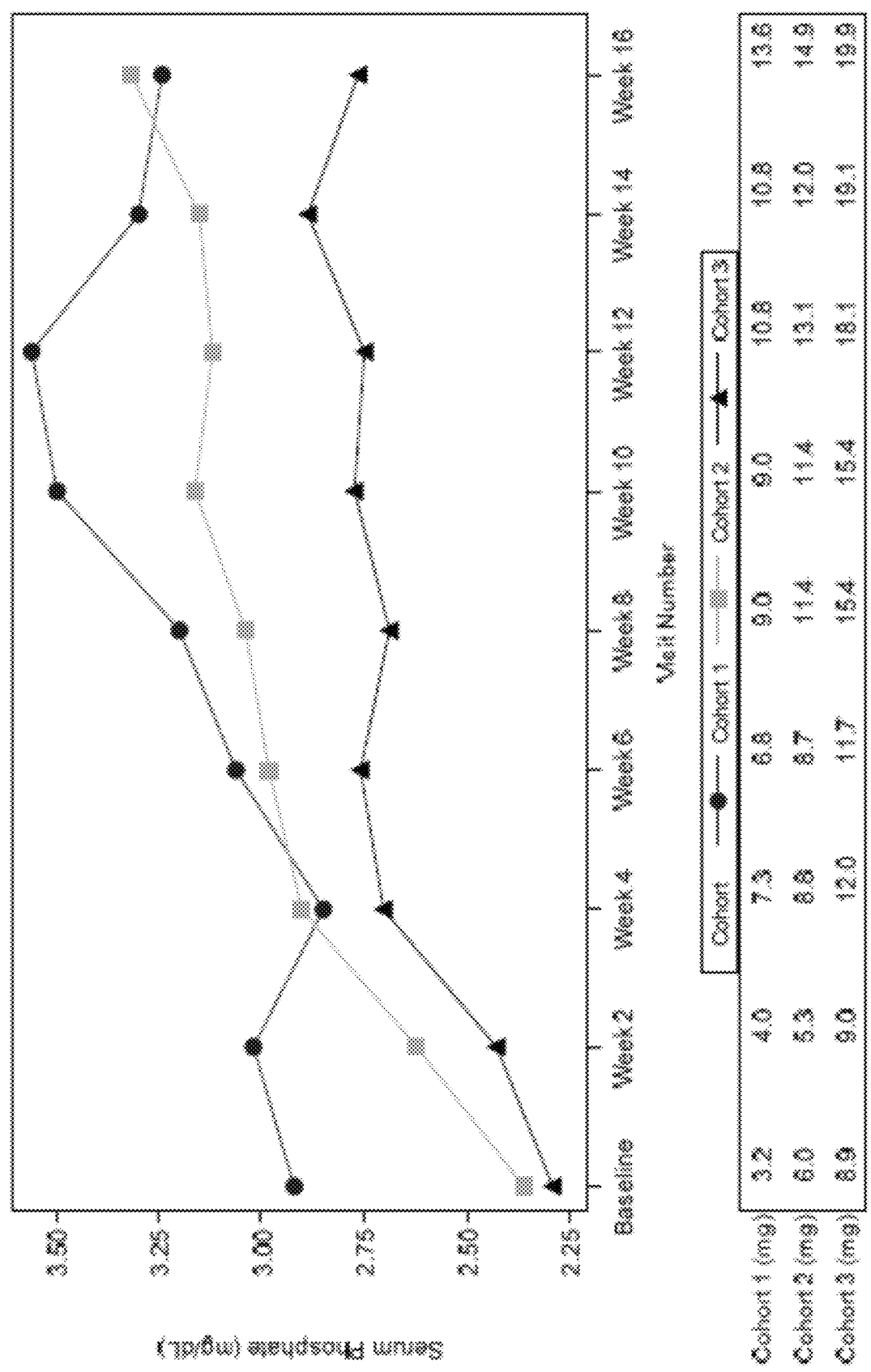
FIG. 19 depicts serum phosphorus levels in pediatric patients treated with a Q2W dosing regimen of the anti-FGF23 antibody KRN23.
Figure 20:
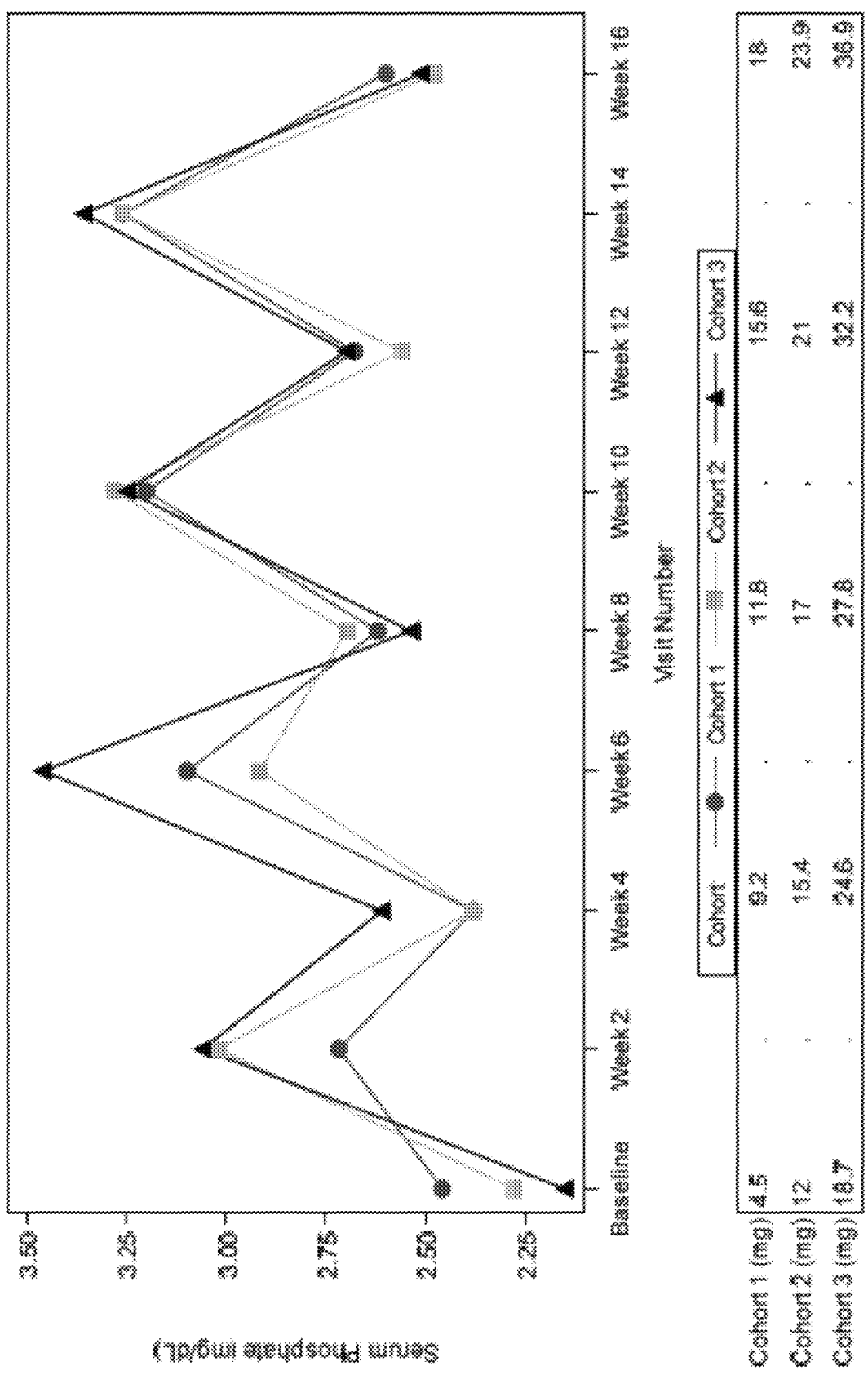
FIG. 20 depicts serum phosphorus levels in pediatric patients treated with a Q4W dosing regimen of the anti-FGF23 antibody KRN23.
Figure 21:
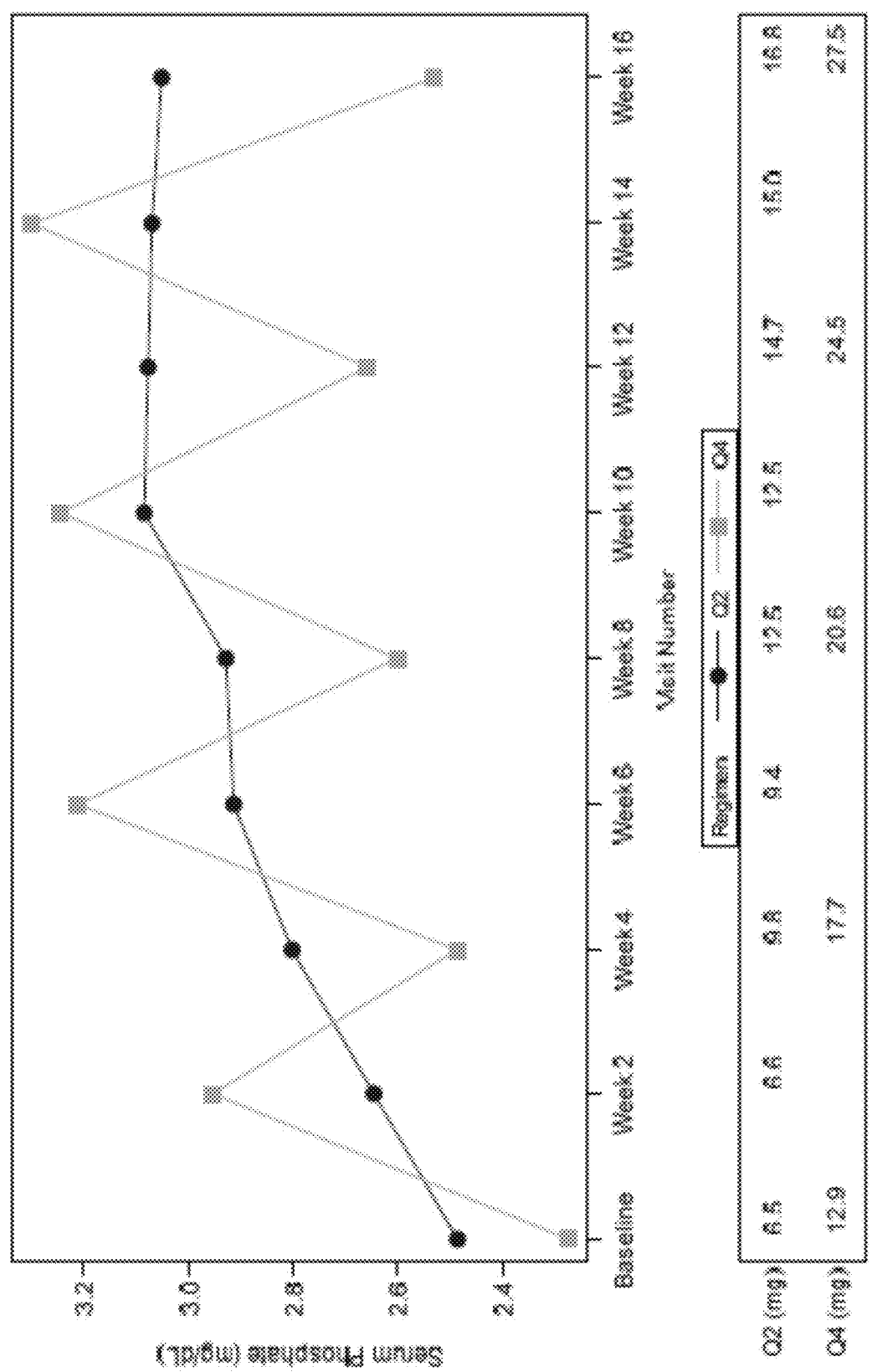
FIG. 21 depicts a side-by-side comparison of serum phosphorus levels in pediatric patients treated with the anti-FGF23 antibody KRN23 in a Q2W dosing regimen or a Q4W dosing regimen.

As noted in example 4, the planned duration of the study is 64 weeks and consists of two periods: a 16-week individual dose Titration Period, followed by a 48-week Treatment Period. Serum phosphorus levels in the Q2W treatment group through 16 weeks of treatment is shown in FIG. 19, which illustrates a relatively steady and stable increase in serum phosphorus levels during 16 weeks of treatment with KRN23. By contrast, serum phosphorus levels in the Q4W treatment group showed larger peaks and troughs, as illustrated in FIG. 20. A side-by-side comparison of serum phosphorus levels in the Q2W treatment group versus the Q4W treatment group across all cohorts is illustrated in FIG. 21. A numerical illustration of serum phosphorus levels in the Q2W and Q4W treatment groups through 24 weeks is shown in Table 24 below.

TABLE 24

Serum Phosphorus Levels by Regimen - Overall

| | Regimen | W0 | W14 | W16 | W22 | W24 |
|---|---|---|---|---|---|---|
| N | Q2 | 18 | 17 | 18 | 11 | 9 |
| | Q4 | 18 | 17 | 17 | 12 | 10 |
| Mean serum P; mg/dL | Q2 | 2.486 | 3.071 | 3.050 | 3.218 | 3.400 |
| | Q4 | 2.272 | 3.300 | 2.529 | 3.325 | 2.830 |
| Mean serum P; Δ vs. BL | Q2 | — | 0.571 | 0.567 | 0.673 | 0.700 |
| | Q4 | — | 1.012 | 0.229 | 1.033 | 0.460 |
| In target range; N (%) | Q2 | — | 5 (29.4%) | 9 (50%) | 6 (54.5%) | 7 (77.8%) |
| | Q4 | — | 12 (70.6%) | 0 (0%) | 9 (75.0%) | 2 (20.0%) |

Figure 22:
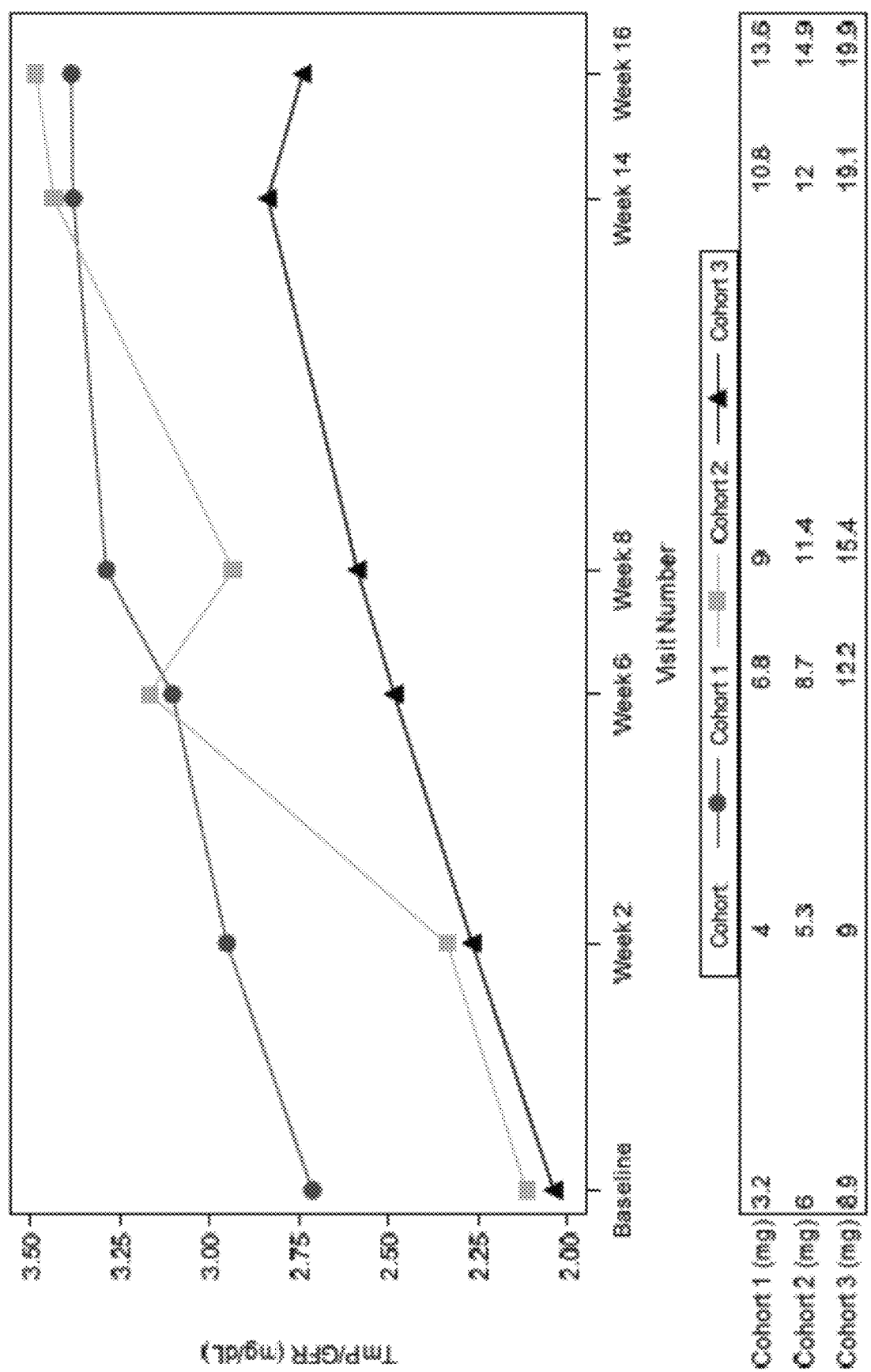
FIG. 22 depicts TmP/GRF levels in pediatric patients treated with a Q2W dosing regimen of the anti-FGF23 antibody KRN23.
Figure 23:
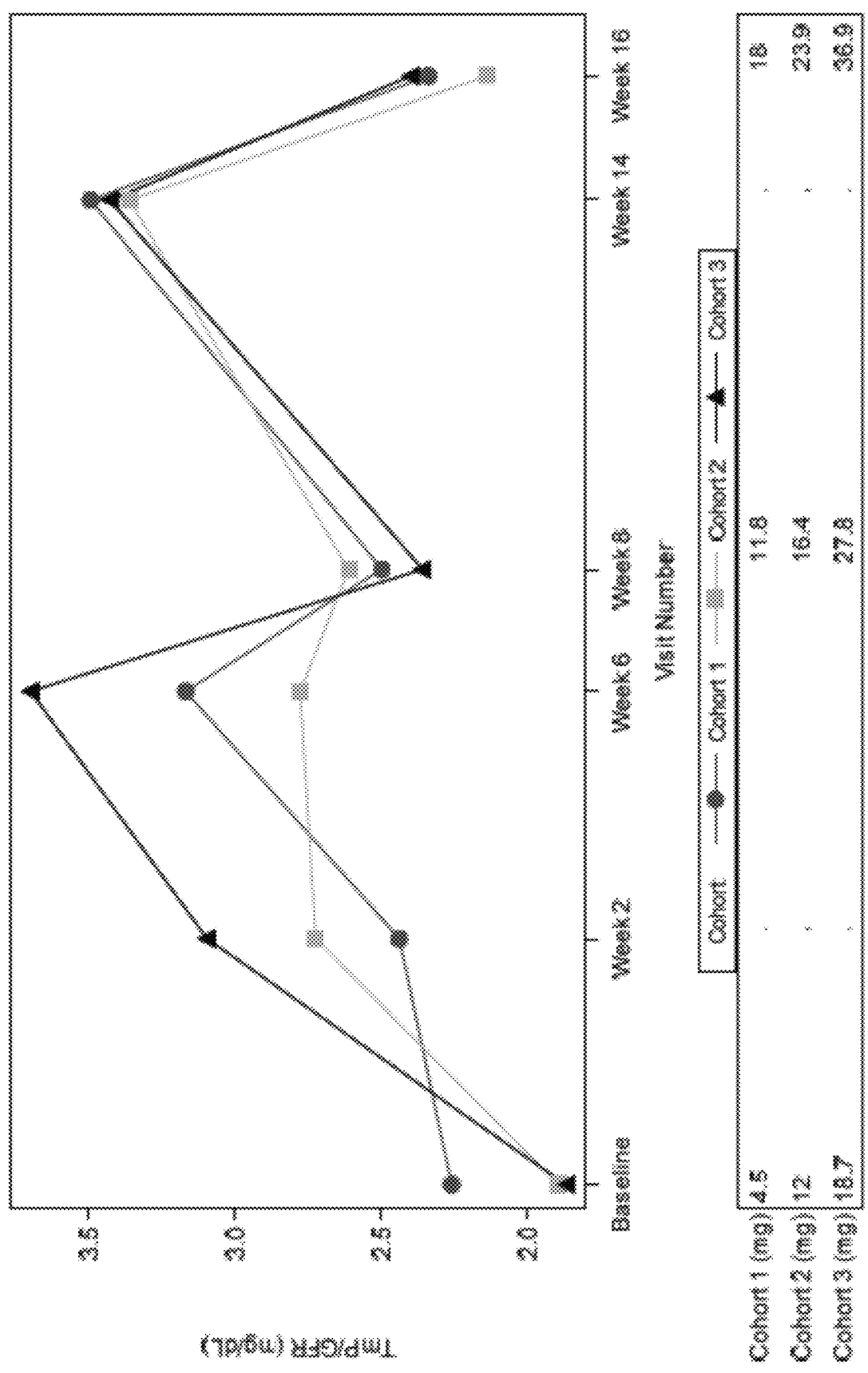
FIG. 23 depicts TmP/GRF levels in pediatric patients treated with a Q4W dosing regimen of the anti-FGF23 antibody KRN23.
Figure 24:
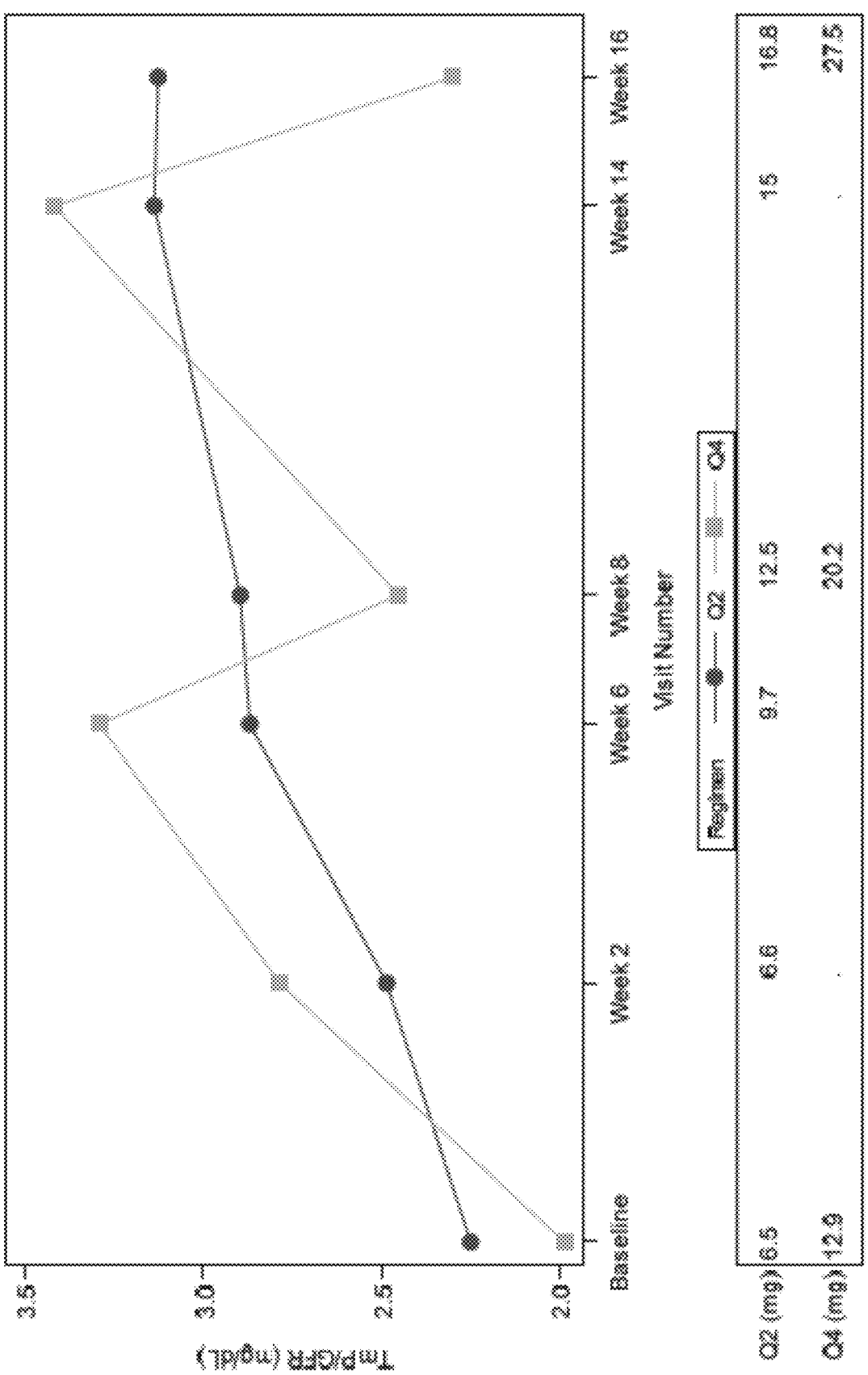
FIG. 24 depicts a side-by-side comparison of TmP/GRF levels in pediatric patients treated with the anti-FGF23 antibody KRN23 in a Q2W dosing regimen or a Q4W dosing regimen.

Similar to the observations with serum phosphorus levels, TmP/GFR levels in the Q2W treatment group also increased at a steadier and more stable pace in comparison to the Q4W treatment group. TmP/GFR levels in the Q2W treatment group through 16 weeks of treatment is shown in FIG. 22, while TmP/GFR levels in the Q4W treatment group are shown in FIG. 23. A side-by-side comparison of TmP/GFR levels in the Q2W treatment group versus the Q4W treatment group across all cohorts is illustrated in FIG. 24. A numerical illustration of serum phosphorus levels in the Q2W and Q4W treatment groups through 24 weeks is shown in Table 25 below.

TABLE 25

TmP/GFR Levels by Regimen-Overall

| | Regimen | W0 | W14 | W16 | W24 |
|---|---|---|---|---|---|
| N | Q2 | 18 | 17 | 18 | 7 |
| | Q4 | 17 | 16 | 16 | 8 |
| Mean Tmp/GFR; mg/dL | Q2 | 2.249 | 3.136 | 3.126 | 3.479 |
| | Q4 | 1.987 | 3.418 | 2.298 | 2.644 |
| Mean Tmp/GFR; Δ vs. BL | Q2 | — | 0.864 | 0.876 | 1.054 |
| | Q4 | — | 1.327 | 0.249 | 0.503 |

Levels of 1,25(OH)$_2$D followed a similar profile as serum phosphorus. A numerical illustration of 1,25(OH)$_2$D levels in the Q2W and Q4W treatment groups through 28 weeks is shown in Table 26 below.

TABLE 26

1,25(OH)$_2$D Levels by Regimen-Overall

| | Regimen | W0 | W14 | W16 | W28 |
|---|---|---|---|---|---|
| N | Q2 | 18 | 17 | 18 | 7 |
| | Q4 | 17 | 16 | 16 | 8 |
| Mean 1,25(OH)$_2$D; pg/mL | Q2 | 40.083 | 65.607 | 59.776 | 86.460 |
| | Q4 | 40.578 | 77.775 | 50.639 | 47.933 |

Figure 25:
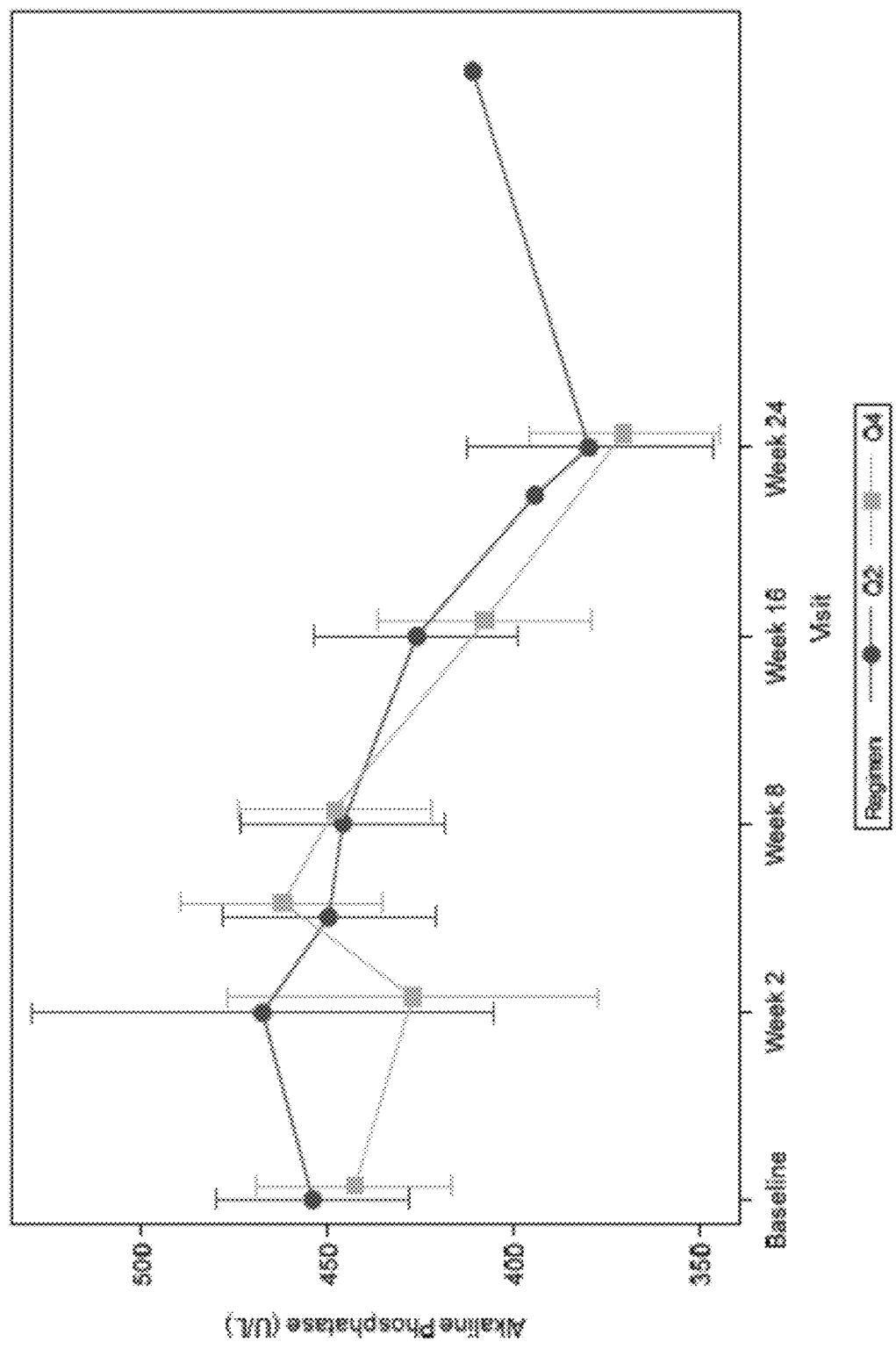
FIG. 25 depicts a side-by-side comparison of serum alkaline phosphatase (ALP) levels in pediatric patients treated with the anti-FGF23 antibody KRN23 in a Q2W dosing regimen or a Q4W dosing regimen.

Levels of the bone biomarker serum alkaline phosphatase (ALP) were also measured and showed a decrease over time for both treating regimens, as illustrated in FIG. 25.

In terms of safety, no severe adverse events were observed through 16 weeks of treatment and there were no adverse events leading to discontinuation. This suggests KRN23 is safe and well-tolerated through the first 16 weeks of the Q2W and Q4W dosing regimens. There were also no observable changes in serum and urinary calcium levels, and minimal changes in mean iPTH, similar to those observed in adults. Lastly, FGF23 levels were seen to increase over the course of KRN23 treatment, as illustrated in Table 27 below.

TABLE 27 iFGF23 Levels by Regimen-Overall

| | Regimen | Baseline | W8 | W16 | W28 |
|---|---|---|---|---|---|
| N | Q2 | 18 | 18 | 18 | 4 |
| | Q4 | 18 | 18 | 18 | 5 |
| Mean iFGF23; pg/mL | Q2 | 163.6 | 144655.6 | 231368.9 | 314650.0 |
| | Q4 | 165.7 | 101815.6 | 149015.0 | 131994.0 |

In conclusion, the dose response in serum phosphorus levels appears to be similar in adult and pediatric patients, with noticeable peaks and troughs observed in the Q4W regimen in comparison to a much steadier and more stable increase in the Q2W regimen. The results in this example further indicate an increase of approximately 1 mg/dL in serum phosphorus levels in response to 1 mg/kg of the KRN23 therapeutic. Additionally, TmP/GFR and 1,25(OH)$_2$D levels generally followed the same profile as serum phosphorus levels in response to Q2W and Q4W dosing, with more stable and steady increases over time in the Q2W dosing treatment group.

The disclosures, including the claims, figures and/or drawings, of each and every patent, patent application, and publication cited herein are hereby incorporated herein by reference in their entireties.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A method of treating X-linked hypophosphatemia (XLH), comprising administering to a subject in need of such treatment an effective amount of an anti-FGF23 antibody, wherein the anti-FGF23 antibody is administered subcutaneously about every two weeks, and wherein the anti-FGF23 antibody comprises the CDR sequences of SEQ ID NO: 1, SEQ ID NO: 2, SEQ ID NO: 3, SEQ ID NO: 4, SEQ ID NO: 5, and SEQ ID NO: 6.

2. The method of claim 1, wherein the heavy chain of the anti-FGF23 antibody comprises a sequence of SEQ ID NO: 7.

3. The method of claim 1, wherein the light chain of the anti-FGF23 antibody comprises a sequence of SEQ ID NO: 8.

4. The method of claim 1, wherein the heavy chain of the anti-FGF23 antibody comprises a sequence of SEQ ID NO: 7 and the light chain of the anti-FGF23 antibody comprises a sequence of SEQ ID NO: 8.

5. The method of claim 1, wherein the anti-FGF23 antibody is administered with a pharmaceutically-acceptable carrier.

6. The method of claim 1, wherein the subject is a pediatric subject.

7. The method of claim 1, wherein the anti-FGF23 antibody is administered at a dose from about 0.05 mg/kg to about 1.0 mg/kg.

8. The method of claim 1, wherein the anti-FGF23 antibody is administered at a dose of about 0.8 mg/kg.

9. The method of claim 1, wherein the anti-FGF23 antibody is administered at a dose of about 1.0 mg/kg.

* * * * *

SEQUENCE LISTING

<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: anti-FGF23 antibody heavy chain variable region
      CDR1

<400> SEQUENCE: 1

Asn His Tyr Met His
1               5

<210> SEQ ID NO 2
<211> LENGTH: 17
<212> TYPE: PRT
<213> ORGANISM: Artificial Sequence
<220> FEATURE:
<223> OTHER INFORMATION: anti-FGF23 antibody heavy chain variable region
      CDR2

<400> SEQUENCE: 2

Ile Ile Asn Pro Ile Ser Gly Ser Thr Ser Asn Ala Gln Lys Phe Gln
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: anti-FGF23 antibody heavy chain variable region
      CDR3

<400> SEQUENCE: 3

Asp Ile Val Asp Ala Phe Asp Phe
1               5

<210> SEQ ID NO 4
<211> LENGTH: 11
<212> TYPE: PRT
<213> ORGANISM: Artificial Sequence
<220> FEATURE:
<223> OTHER INFORMATION: anti-FGF23 antibody light chain variable region
      CDR1

<400> SEQUENCE: 4

Arg Ala Ser Gln Gly Ile Ser Ser Ala Leu Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: anti-FGF23 antibody light chain variable region
      CDR2

<400> SEQUENCE: 5

Asp Ala Ser Ser Leu Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: anti-FGF23 antibody light chain variable region
      CDR3

<400> SEQUENCE: 6

Gln Gln Phe Asn Asp Tyr Phe Thr
1               5

<210> SEQ ID NO 7
<211> LENGTH: 447
<212> TYPE: PRT
<213> ORGANISM: Artificial Sequence
<220> FEATURE:
<223> OTHER INFORMATION: KRN23 antibody heavy chain

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
        35                  40                  45

Gly Ile Ile Asn Pro Ile Ser Gly Ser Thr Ser Asn Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ile Val Asp Ala Phe Asp Phe Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 8
<211> LENGTH: 213
<212> TYPE: PRT
<213> ORGANISM: Artificial Sequence
<220> FEATURE:
<223> OTHER INFORMATION: KRN23 antibody light chain

<400> SEQUENCE: 8

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Val Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asp Tyr Phe Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 9
<211> LENGTH: 447
```

```
<212> TYPE: PRT
<213> ORGANISM: Artificial Sequence
<220> FEATURE:
<223> OTHER INFORMATION: C10 antibody heavy chain

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
        35                  40                  45

Gly Ile Ile Asn Pro Ile Ser Gly Ser Thr Ser Asn Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ile Val Asp Ala Phe Asp Phe Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 10
<211> LENGTH: 213
<212> TYPE: PRT
<213> ORGANISM: Artificial Sequence
<220> FEATURE:
<223> OTHER INFORMATION: C10 antibody light chain

<400> SEQUENCE: 10

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asp Tyr Phe Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 4
<212> TYPE: PRT
<213> ORGANISM: Artificial Sequence
<220> FEATURE:
<223> OTHER INFORMATION: proteolytic cleavage site
<220> FEATURE:
<221> NAME/KEY: MISC_FEATURE
<222> LOCATION: (2)..(2)
<223> OTHER INFORMATION: May be His
<220> FEATURE:
<221> NAME/KEY: MISC_FEATURE
<222> LOCATION: (3)..(3)
<223> OTHER INFORMATION: May be Thr
```

<400> SEQUENCE: 11

Arg Xaa Xaa Arg
1

<210> SEQ ID NO 12
<211> LENGTH: 251
<212> TYPE: PRT
<213> ORGANISM: Homo sapiens

<400> SEQUENCE: 12

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 13
<211> LENGTH: 251
<212> TYPE: PRT
<213> ORGANISM: Mus sp.

<400> SEQUENCE: 13

Met Leu Gly Thr Cys Leu Arg Leu Leu Val Gly Val Leu Cys Thr Val
1               5                   10                  15

Cys Ser Leu Gly Thr Ala Arg Ala Tyr Pro Asp Thr Ser Pro Leu Leu
            20                  25                  30

Gly Ser Asn Trp Gly Ser Leu His Leu Tyr Thr Ala Thr Ala Arg
        35                  40                  45

```
Thr Ser Tyr His Leu Gln Ile His Arg Asp Gly His Tyr Asp Gly Thr
     50                  55                  60

Pro His Gln Thr Ile Tyr Ser Ala Leu Met Ile Thr Ser Glu Asp Ala
 65                  70                  75                  80

Gly Ser Val Val Ile Thr Gly Ala Met Thr Arg Arg Phe Leu Cys Met
                     85                  90                  95

Asp Leu His Gly Asn Ile Phe Gly Ser Leu His Phe Ser Pro Glu Asn
                100                 105                 110

Cys Lys Phe Arg Gln Trp Thr Leu Glu Asn Gly Tyr Asp Val Tyr Leu
                115                 120                 125

Ser Gln Lys His His Tyr Leu Val Ser Leu Gly Arg Ala Lys Arg Ile
            130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Pro Glu Arg Asp Pro Ile Asn Tyr
            180                 185                 190

Leu Lys Pro Arg Pro Arg Ala Thr Pro Val Pro Val Ser Cys Ser Arg
                195                 200                 205

Glu Leu Pro Ser Ala Glu Glu Gly Gly Pro Ala Ala Ser Asp Pro Leu
210                 215                 220

Gly Tyr Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250

<210> SEQ ID NO 14
<211> LENGTH: 5
<212> TYPE: PRT
<213> ORGANISM: Artificial Sequence
<220> FEATURE:
<223> OTHER INFORMATION: subtilisin-like proprotein convertase (SPC)
      site

<400> SEQUENCE: 14

Arg His Thr Arg Ser
1               5

<210> SEQ ID NO 15
<211> LENGTH: 910
<212> TYPE: PRT
<213> ORGANISM: Homo sapiens

<400> SEQUENCE: 15

Asp Ser Arg Asn Ala Ser Leu Pro Leu Gly Ala Pro Ser Pro Leu Gln
1               5                   10                  15

Pro Ala Thr Gly Asp Val Ala Ser Asp Ser Tyr Asn Asn Val Phe Arg
                20                  25                  30

Asp Thr Glu Ala Leu Arg Glu Leu Gly Val Thr His Tyr Arg Phe Ser
                35                  40                  45

Ile Ser Trp Ala Arg Val Leu Pro Asn Gly Ser Ala Gly Val Pro Asn
            50                  55                  60

Arg Glu Gly Leu Arg Tyr Tyr Arg Arg Leu Leu Glu Arg Leu Arg Glu
65                  70                  75                  80

Leu Gly Val Gln Pro Val Val Thr Leu Tyr His Trp Asp Leu Pro Gln
                85                  90                  95
```

-continued

```
Arg Leu Gln Asp Ala Tyr Gly Gly Trp Ala Asn Arg Ala Leu Ala Asp
                100                 105                 110
His Phe Arg Asp Tyr Ala Glu Leu Cys Phe Arg His Phe Gly Gly Gln
            115                 120                 125
Val Lys Tyr Trp Ile Thr Ile Asp Asn Pro Tyr Val Val Ala Trp His
    130                 135                 140
Gly Tyr Ala Thr Gly Arg Leu Ala Pro Gly Ile Arg Gly Ser Pro Arg
145                 150                 155                 160
Leu Gly Tyr Leu Val Ala His Asn Leu Leu Ala His Ala Lys Val
                165                 170                 175
Trp His Leu Tyr Asn Thr Ser Phe Arg Pro Thr Gln Gly Gly Gln Val
            180                 185                 190
Ser Ile Ala Leu Ser Ser His Trp Ile Asn Pro Arg Arg Met Thr Asp
    195                 200                 205
His Ser Ile Lys Glu Cys Gln Lys Ser Leu Asp Phe Val Leu Gly Trp
210                 215                 220
Phe Ala Lys Pro Val Phe Ile Asp Gly Asp Tyr Pro Glu Ser Met Lys
225                 230                 235                 240
Asn Asn Leu Ser Ser Ile Leu Pro Asp Phe Thr Glu Ser Glu Lys Lys
                245                 250                 255
Phe Ile Lys Gly Thr Ala Asp Phe Phe Ala Leu Cys Phe Gly Pro Thr
            260                 265                 270
Leu Ser Phe Gln Leu Leu Asp Pro His Met Lys Phe Arg Gln Leu Glu
    275                 280                 285
Ser Pro Asn Leu Arg Gln Leu Leu Ser Trp Ile Asp Leu Glu Phe Asn
290                 295                 300
His Pro Gln Ile Phe Ile Val Glu Asn Gly Trp Phe Val Ser Gly Thr
305                 310                 315                 320
Thr Lys Arg Asp Asp Ala Lys Tyr Met Tyr Tyr Leu Lys Lys Phe Ile
                325                 330                 335
Met Glu Thr Leu Lys Ala Ile Lys Leu Asp Gly Val Asp Val Ile Gly
            340                 345                 350
Tyr Thr Ala Trp Ser Leu Met Asp Gly Phe Glu Trp His Arg Gly Tyr
    355                 360                 365
Ser Ile Arg Arg Gly Leu Phe Tyr Val Asp Phe Leu Ser Gln Asp Lys
370                 375                 380
Met Leu Leu Pro Lys Ser Ser Ala Leu Phe Tyr Gln Lys Leu Ile Glu
385                 390                 395                 400
Lys Asn Gly Phe Pro Pro Leu Pro Glu Asn Gln Pro Leu Glu Gly Thr
                405                 410                 415
Phe Pro Cys Asp Phe Ala Trp Gly Val Val Asp Asn Tyr Ile Gln Val
            420                 425                 430
Asp Thr Thr Leu Ser Gln Phe Thr Asp Leu Asn Val Tyr Leu Trp Asp
    435                 440                 445
Val His His Ser Lys Arg Leu Ile Lys Val Asp Gly Val Val Thr Lys
450                 455                 460
Lys Arg Lys Ser Tyr Cys Val Asp Phe Ala Ala Ile Gln Pro Gln Ile
465                 470                 475                 480
Ala Leu Leu Gln Glu Met His Val Thr His Phe Arg Phe Ser Leu Asp
                485                 490                 495
Trp Ala Leu Ile Leu Pro Leu Gly Asn Gln Ser Gln Val Asn His Thr
            500                 505                 510
Ile Leu Gln Tyr Tyr Arg Cys Met Ala Ser Glu Leu Val Arg Val Asn
```

```
                515                 520                 525
Ile Thr Pro Val Val Ala Leu Trp Gln Pro Met Ala Pro Asn Gln Gly
            530                 535                 540

Leu Pro Arg Leu Leu Ala Arg Gln Gly Ala Trp Glu Asn Pro Tyr Thr
545                 550                 555                 560

Ala Leu Ala Phe Ala Glu Tyr Ala Arg Leu Cys Phe Gly Glu Leu Gly
                565                 570                 575

His His Val Lys Leu Trp Ile Thr Met Asn Glu Pro Tyr Thr Arg Asn
            580                 585                 590

Met Thr Tyr Ser Ala Gly His Asn Leu Leu Lys Ala His Ala Leu Ala
        595                 600                 605

Trp His Val Tyr Asn Glu Lys Phe Arg His Ala Gln Asn Gly Lys Ile
    610                 615                 620

Ser Ile Ala Leu Gln Ala Asp Trp Ile Glu Pro Ala Cys Pro Phe Ser
625                 630                 635                 640

Gln Lys Asp Lys Glu Val Ala Glu Arg Val Leu Glu Phe Asp Ile Gly
                645                 650                 655

Trp Leu Ala Glu Pro Ile Phe Gly Ser Gly Asp Tyr Pro Trp Val Met
            660                 665                 670

Arg Asp Trp Leu Asn Gln Arg Asn Asn Phe Leu Leu Pro Tyr Phe Thr
        675                 680                 685

Glu Asp Glu Lys Lys Leu Ile Gln Gly Thr Phe Asp Phe Leu Ala Leu
    690                 695                 700

Ser His Tyr Thr Thr Ile Leu Val Asp Ser Glu Lys Glu Asp Pro Ile
705                 710                 715                 720

Lys Tyr Asn Asp Tyr Leu Glu Val Gln Glu Met Thr Asp Ile Thr Trp
                725                 730                 735

Leu Asn Ser Pro Ser Gln Val Ala Val Pro Trp Gly Leu Arg Lys
            740                 745                 750

Val Leu Asn Trp Leu Lys Phe Lys Tyr Gly Asp Leu Pro Met Tyr Ile
        755                 760                 765

Ile Ser Asn Gly Ile Asp Asp Gly Leu His Ala Glu Asp Asp Gln Leu
    770                 775                 780

Arg Val Tyr Tyr Met Gln Asn Tyr Ile Asn Glu Ala Leu Lys Ala His
785                 790                 795                 800

Ile Leu Asp Gly Ile Asn Leu Cys Gly Tyr Phe Ala Tyr Ser Phe Asn
                805                 810                 815

Asp Arg Thr Ala Pro Arg Phe Gly Leu Tyr Arg Tyr Ala Ala Asp Gln
            820                 825                 830

Phe Glu Pro Lys Ala Ser Met Lys His Tyr Arg Lys Ile Ile Asp Ser
        835                 840                 845

Asn Gly Phe Pro Gly Pro Glu Thr Leu Glu Arg Phe Cys Pro Glu Glu
    850                 855                 860

Phe Thr Val Cys Thr Glu Cys Ser Phe Phe His Thr Arg Lys Ser Leu
865                 870                 875                 880

Leu Ala Phe Ile Ala Phe Leu Phe Phe Ala Ser Ile Ile Ser Leu Ser
                885                 890                 895

Leu Ile Phe Tyr Tyr Ser Lys Lys Gly Arg Arg Ser Tyr Lys
            900                 905                 910

<210> SEQ ID NO 16
<211> LENGTH: 117
<212> TYPE: PRT
<213> ORGANISM: Artificial Sequence
```

```
<220> FEATURE:
<223> OTHER INFORMATION: anti-FGF23 antibody heavy chain variable region

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
        35                  40                  45

Gly Ile Ile Asn Pro Ile Ser Gly Ser Thr Ser Asn Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ile Val Asp Ala Phe Asp Phe Trp Gly Gln Gly Thr Met
            100                 105                 110

Val Thr Val Ser Ser
        115

<210> SEQ ID NO 17
<211> LENGTH: 106
<212> TYPE: PRT
<213> ORGANISM: Artificial Sequence
<220> FEATURE:
<223> OTHER INFORMATION: anti-FGF23 antibody light chain variable region

<400> SEQUENCE: 17

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asp Tyr Phe Thr
                85                  90                  95

Phe Gly Pro Gly Thr Lys Val Asp Ile Lys
            100                 105
```